(12) United States Patent
Poree et al.

(10) Patent No.: US 10,400,249 B2
(45) Date of Patent: Sep. 3, 2019

(54) HPPD VARIANTS AND METHODS OF USE

(71) Applicants: BAYER CROPSCIENCE AKTIENGESELLSCHAFT, Monheim am Rhein (DE); BAYER CROPSCIENCE LP, Research Triangle Park, NC (US)

(72) Inventors: Fabien Poree, Frankfurt (DE); Bernd Laber, Idstein (DE); Gudrun Lange, Kelkheim (DE); Manuel Dubald, Raleigh, NC (US); Roxanne Armstrong, Cary, NC (US)

(73) Assignee: BASF AGRICULTURAL SOLUTIONS SEED, US LLC, Research Triangle Park, NC (US)

( * ) Notice: Subject to any disclaimer, the term of this patent is extended or adjusted under 35 U.S.C. 154(b) by 0 days.

(21) Appl. No.: 15/124,861

(22) PCT Filed: Mar. 9, 2015

(86) PCT No.: PCT/EP2015/054858
§ 371 (c)(1),
(2) Date: Sep. 9, 2016

(87) PCT Pub. No.: WO2015/135881
PCT Pub. Date: Sep. 17, 2015

(65) Prior Publication Data
US 2017/0016018 A1 Jan. 19, 2017

Related U.S. Application Data

(60) Provisional application No. 61/951,039, filed on Mar. 11, 2014.

(30) Foreign Application Priority Data

Mar. 13, 2014 (EP) ..................................... 14159634

(51) Int. Cl.
C12N 15/82 (2006.01)
A01N 43/713 (2006.01)
C12N 9/02 (2006.01)

(52) U.S. Cl.
CPC ....... C12N 15/8274 (2013.01); A01N 43/713 (2013.01); C12N 9/0069 (2013.01); C12Y 113/11001 (2013.01)

(58) Field of Classification Search
None
See application file for complete search history.

(56) References Cited

U.S. PATENT DOCUMENTS 6,245,968 B1 * 6/2001 Boudec ................ C12N 9/0069
435/320.1

2011/0039706 A1 * 2/2011 Busch .................. C12N 9/0069
504/348
2011/0185444 A1 7/2011 Li et al.
2012/0042413 A1 2/2012 Albert et al.
2014/0223597 A1 8/2014 Busch et al.

FOREIGN PATENT DOCUMENTS

| EP | 2453012 A1 | 5/2012 |
|---|---|---|
| WO | 9638567 A2 | 6/1996 |
| WO | 0246387 A2 | 6/2002 |
| WO | 2009144079 A1 | 12/2009 |
| WO | 2010085705 A2 | 7/2010 |
| WO | WO 2010/085705 A2 * | 7/2010 |
| WO | 2011068567 A1 | 6/2011 |
| WO | 2011094199 A1 | 8/2011 |

OTHER PUBLICATIONS

Keskin et al., 2004, Protein Science 13: 1043-1055.*
Guo et al., 2004, Proceedings of the National Academy of Sciences USA 101: 9205-9210.*
Thornton et al., 2000, Nature Structural Biology, structural genomic supplement, Nov. 2000: 991-994.*
Pseudomonas fluorescens 4-hydroxyphenylpyruvate dioxygenase sequence, GenBank accession No. WP_021493116, published Sep. 22, 2013.*
International Search Report dated May 13, 2015, issued in PCT/EP2015/054858.
Dufourmantel et al., "Generation and characterization of soybean and marker free tobacco plastid transformants over-expressing . . . " Plant Biotechnol J. (2007), 5(1):118-33.
Kakidani Hitoshi et al., "Three-Dimensional Modeling of Plant 4-Hydroxyphenylpyruvate Dioxygenase, a Molecular Target of Triketone-Type Herbicides" Journal of Pesticide Science. (2003), vol. 28, No. 4, 409-415.
Morrison, John F., "The slow-binding and slow, tight binding inhibition of enzyme-catalysed reactions" Trends Biochem. Sci. (1982) 7:102-105.
Rüetschi et al., "Characterization of 4-hydroxyphenylpyruvate dioxygenase" Eur. J. Biochem. (1992) 205, 459-466.

* cited by examiner

Primary Examiner — Bratislav Stankovic
(74) Attorney, Agent, or Firm — McBee Moore Woodward & Vanik IP, LLC

(57) ABSTRACT

In the present invention, HPPD enzymes and plants containing them showing a full tolerance against several classes of HPPD-inhibitors are described.
A set of HPPD enzymes have been designed which have either no or only a significantly reduced affinity to HPPD inhibitors and, at the same time, the rate of dissociation of the HPPD inhibitors of the enzyme is increased to such an extent that the HPPD inhibitors no longer act as slow-binding or slow, tight-binding inhibitors but, instead of this, have become fully reversible inhibitors.
In particular, isolated polynucleotides encoding HPPD inhibitor tolerance polypeptides are provided. Additionally, amino acid sequences corresponding to the polynucleotides are encompassed.

20 Claims, 4 Drawing Sheets
Specification includes a Sequence Listing.

```
PfHPPD                    MADLYENPMGLMG--------------------------------------FEF 16
Avena_sativa              MPPTPAT-ATGAAAAAVTPEHAARS----FPRVVRVNPRSDRFPVLSFHH 45
Avena_sativa_del_         MPPTPAT-ATGAAAAAVTPEHAARS----FPRVVRVNPRSDRFPVLSFHH 45
Zea_mays                  MGPTPTAAAAGAAVAAASAAEQAAFRLVGHRNFVRFNPRSDRFHTLAFHH 50
Arabidopsis_thaliana      MGHQNAAVSENQNHDDGAASSPGFKLVG-FSKFVRKNPKSDKFRVKRFHH 49
Hordeum_vulgare           MPPTPTTPAATGAAAAVTPEHARP------HRMVRFNPRSDRFHTLSFHH 44
Daucus_carota             MGKK-QSEAEILSSNSSNTSPATFKLVG-FNNFVRANPKSDHFAVKRFHH 48
Streptomyces_avermitilis  MTQTTHHTPDTARQADPFP-----------------------VKGMDA 25
Mycosphaerella_graminicola MAPGALLVTSQNGRTSPLYDSDGYVPAP------AALVVGGEVNYRGYHH 44
Coccicoides_immitis       MAPAADSPTLQPAQFSDLN---------------------QYRGYDH 26
                          *                                            .

PfHPPD                    IEFASPTPGTLEPIFEIMGFTKVATHRSKN-------VHLYRQGEINLIL 59
Avena_sativa              VELWCADAASAAGRFSFALGAPLAARSDLSTGNSAHASLLLRSGALAFLF 95
Avena_sativa_del_         VELWCADAASAAGRFSFALGAPLAARSDLSTGNSAHASLLLRSGALAFLF 95
Zea_mays                  VELWCADAASAAGRFSFGLGAPLAARSDLSTGNSAHASLLLRSGSLSFLF 100
Arabidopsis_thaliana      IEFWCGDATNVARRFSWGLGMRFSAKSDLSTGNMVHASYLLTSGDLRFLF 99
Hordeum_vulgare           VEFWCADAASAAGRFAFALGAPLAARSDLSTGNSAHASQLLRSGSLAFLF 94
Daucus_carota             IEFWCGDATNTSRRFSWGLGMPLVAKSDLSTGNSVHASYLVRSANLSFVF 98
Streptomyces_avermitilis  VVFAVGNAKQAA-HYSTAFGMQLVAYSGPENGSRETASYVLTNGSARFVL 74
Mycosphaerella_graminicola AEWWVGNAKQVAQFYITRMGFEFVAHKGLETGSRFFASHVVQNNGVRFVF 94
Coccicoides_immitis       VHWYVGNAKQAATYYVTRMGFERVAYRGLETGSKAVASHVVRNGNITFIL 76
                           .    :      :  ..     :  .    :::

PfHPPD                    NNEPNS-----------------------IASYFAAEHGPSVCGMAFRVKDS 88
Avena_sativa              TAPYAPPPQEA-ATAAATASIPSFSADAARTFAAAHGLAVRSVGVRVADA 144
Avena_sativa_del_         TAPYAPPPQEA-AT-AATASIPSFSADAARTFAAAHGLAVRSVGVRVADA 143
Zea_mays                  TAPYAH------GADAATAALPSFSAAAARRFAADHGLAVRAVALRVADA 144
Arabidopsis_thaliana      TAPYSPSLSAGEIKPTTTASIPSFDHGSCRSFFSSHGLGVRAVAIEVEDA 149
Hordeum_vulgare           TAPYAN------GCDAATASLPSFSADAARRFSSDHGIAVRSVALRVADA 138
Daucus_carota             TAPYSPSTTT----SSGSAAIPSFSASGFHSFAAKHGLAVRAIALEVADV 144
Streptomyces_avermitilis  TSVIKFATPWG----HFLA-------------DHVAEHGDGVVDLAIEVPDA 109
Mycosphaerella_graminicola TSPVRSSARQT----LKAAPLADQARLDEMYDHLDKHGDGVKDVAFEVDDV 141
Coccicoides_immitis       TSPLRSVEQAS----RFPE----DEALLKEIHAHLERHGDGVKDVAFEVDCV 120
                          .                          .  ** .*  :...*

PfHPPD                    QKAYNRALELGAQP----IHIDTGPMELNLPAIKGIGGAPLYLIDRFGEG 134
Avena_sativa              AEAFRVSVAGGARPAFAPADLG---HGFGLAEVELYGDVVLRFVSYPDET 191
Avena_sativa_del_         AEAFRVSVAGGARPAFAPADLG----HGFGLAEVELYGDVVLRFVSYPDET 190
Zea_mays                  EDAFRASVAGGARPAFGPVDLG---RGFRLAEVELYGDVVLRYVSYPDGA 191
Arabidopsis_thaliana      ESAFSISVANGAIPSSPPIVLN---EAVTIAEVKLYGDVVLRYVSYKAED 196
Hordeum_vulgare           AEAFRASRRGARPAFAPVDLG---RGFAFAEVELYGDVVLRFVSHPDGT 185
Daucus_carota             AAAFEASVARGARPASAPVELD---DQAWLAEVELYGDVVLRFVSFGREE 191
Streptomyces_avermitilis  RAAHAYAIEHGAPSVAEPYELKDEHGTVVLAAIATYGKTRHTLVDRTGYD 159
Mycosphaerella_graminicola LAVYENAVANGAESVSSPHTDSCDEGDVISAAIKTYGDTTHTFIQRTTYT 191
Coccicoides_immitis       ESVFSAAVRNGAEVVSDVRTVEDEDGQIKMATIRTYGETTHTLIERSGYR 170
                          ..  :   **          *   .

PfHPPD                    S--SIYDIDFVYLEG---VERNPVGAGLKVIDHLTHNVYRGRMVYWANFY 179
Avena_sativa              D--LPFLPGFERVS-----SPGAVDYGLTRFDHVVGN--VPEMAPVIDYM 232
Avena_sativa_del_         D--LPFLPGFERVS-----SPGAVDYGLTRFDHVVGN--VPEMAPVIDYM 231
Zea_mays                  AG-EPFLPGFEGVA------SPGAADYGLSRFDHIVGN--VPELAPAAAYF 233
Arabidopsis_thaliana      TEKSEFLPGFERVEDA---SSFP-LDYGIRRLDHAVGN--VPELGPALTYV 241
Hordeum_vulgare           D--VPFLPGFEGVT------NPDAVDYGLTRFDHVVGN--VPELAPAAAYI 226
Daucus_carota             ----GLFLPGFEAVEGT---ASFPDLDYGIRPLDHAVGN--VTELGPVVEYI 234
Streptomyces_avermitilis  G----PYLPGYVAAAPIVEPPAHR----TFQAIDHCVGNVELGRMNEWVGFY 203
Mycosphaerella_graminicola G----PFLPGYRSCTTVDSANKFLPVNLEAIDHCVGNQDWDEMSDACDFY 238
Coccicoides_immitis       G----GFMPGYPMESNADATSKFLPKVVLERIDHCVGNQDWDEMERVCDYY 217
                              .:          :  :** .  *  .:   :
```

FIG. 1A

```
PfHPPD                     EKLFNFREARYF---DIKGEYTGLTSKAMSAPDGMIRIPLNE--ESSKGA 224
Avena_sativa               KGFLGFHEFAEFTAEDVGTTESGLNSVVLANNSEAVLLPLNEPVHGTKRR 282
Avena_sativa_del_          KGFLGFHEFAEFTAEDVGTTESGLNSVVLANNSEAVLLPLNEPVHGTKRR 281
Zea_mays                   AGFTGFHEFAEFTTEDVGTAESGLNSMVLANNSENVLLPLNEPVHGTKRR 283
Arabidopsis_thaliana       AGFTGFHQFAEFTADDVGTAESGLNSAVLASNDEMVLLPINEPVHGTKRK 291
Hordeum_vulgare            AGFTGFHEFAEFTAEDVGTTESGLNSVVLANNSEGVLLPLNEPVHGTKRR 276
Daucus_carota              KGFTGFHEFAEFTAEDVGTLESGLNSVVLANNEEMVLLPLNEPVYGTKRK 284
Streptomyces_avermitilis   NKVMGFTNMKEFVGDDIATEYSALMSKVVADGTLKVRFPINEPALAKK-K 252
Mycosphaerella_graminicola ERCLGFHRFWSVDDKDICTEFSALKSIVMSSPNQVVKMPINEPAHGKK-K 287
Coccicoides_immitis        EKILGFHRFWSVDDKDICTEFSALKSIVMASPNDIVKMPINEPAKGKK-Q 266
                             .*  .   . *:     :.* * .::      :  :*:**    ..*

PfHPPD                     GQIEEFLMQFNGEGIQHVAFLTDDLVKTWDALKKIG-----MRFMTAPPDT 270
Avena_sativa               SQIQTYLEYHGGPGVQHIALASNDVLRTLREMRARTPMGGFEFMAPPQAK 332
Avena_sativa_del_          SQIQTYLEYHGGPGVQHIALASNDVLRTLREMRARTPMGGFEFMAPPQAK 331
Zea_mays                   SQIQTFLDHHGGPGVQHMALASDDVLRTLREMQARSAMGGFEFMAPPTSD 333
Arabidopsis_thaliana       SQIQTYLEHNEGAGLQHLALMSEDIFRTLREMRKSSIGGFDFMPSPPPT 341
Hordeum_vulgare            SQIQTFLEHHGGPGVQHIAVASSDVLRTLRKMRARSAMGGFDFLPPPLPK 326
Daucus_carota              SQIQTYLEHNEGAGVQHLALVSEDIFRTLREMPKRSCLGGFEFMPSPPPT 334
Streptomyces_avermitilis   SQIDEYLEFYGGAGVQHIALNTGDIVETVRTMRAA----GVQFLDTP-DS 297
Mycosphaerella_graminicola SQIEEYVDFYNGPGVQHIALRTPNIIEAVSNLRSR----GVEFISVP-DT 332
Coccicoides_immitis        SQIEEYVDFYNGAGVQHIALRTNNIIDAITNLKAR----GTEFIKVP-ET 311
                            .**:  ::    * *;**:*.  : ::.  :    ::     *:   *

PfHPPD                     YYEMLEGRLPDHG-----EPVDQLQARGILLDGSSVEGDKRLLLQIFSETL 316
Avena_sativa               YYEGVRRIAGDVLS--EEQIKECQELGVLVD----RDDQGVLLQIFTKPV 376
Avena_sativa_del_          YYEGVRRIAGDVLS--EEQIKECQELGVLVD----RDDQGVLLQIFTKPV 375
Zea_mays                   YYDGVRRRAGDVLT--EAQIKECQELGVLVD----RDDQGVLLQIFTKPV 377
Arabidopsis_thaliana       YYQNLKKRVGDVLS--DDQIKECEELGILVD----RDDQGTLLQIFTKPL 385
Hordeum_vulgare            YYEGVRRLAGDVLS--EAQIKECQELGVLVD----RDDQGVLLQIFTKPV 370
Daucus_carota              YYKNLKNRVGDVLS--DEQIKECEDLGILVD-----RDDQGTLLQIFTKPV 378
Streptomyces_avermitilis   YYDTLGEWVGDT----RVPVDTLRELKILAD----RDEDGYLLQFTKPV 339
Mycosphaerella_graminicola YYENMRLRLKAAGMKLEESFDIIQKLNILID-----FDEGGYLLQLFTKPL 378
Coccicoides_immitis        YYEDMKIRLRKQGLVLDEDFETLKSLDILID-----FDENGYLLQLFTKHL 357
                           **. :         ..  :* *   .:   ***:*:: :

PfHPPD                     MG--PVFFEFIQRK--------------GDDGFGEGNFKALFESIERDQ 349
Avena_sativa               GDRPTFFLEMIQRIGCMEKDEVGQEYQKGGCGGFGKGNFSELFKSIEDYE 426
Avena_sativa_del_          GDRPTFFLEMIQRIGCMEKDEVGQEYQKGGCGGFGKGNFSELFKSIEDYE 425
Zea_mays                   GDRPTLFLEIIQRIGCMEKDEKGQEYQKGGCGGFGKGNFSQLFKSIEDYE 427
Arabidopsis_thaliana       GDRPTIFIEIIQRVGCMMKDEEGKAYQSGGCGGFGKGNFSELFKSIEEYE 435
Hordeum_vulgare            GDRPTLFLEMIQRIGCMEKDERGEEYQKGGCGGFGKGNFSELFKSIEDYE 420
Daucus_carota              GDRPTLFIEIIQRVGCMLKDDAGQMYQKGGCGGFGKGNFSELFKSIEEYE 428
Streptomyces_avermitilis   QDRPTFEIIERH------------GSMGFGKGNFKALFEAIEREQ 374
Mycosphaerella_graminicola MDRPTVFIEIIQRN---------------NFDGFGAGNFKSLFEAIEREQ 413
Coccicoides_immitis        MDRPTVFIEIIQRN---------------NFSGFGAGNFRALFEAIEREQ 392
                             . ..*:*:*:*                    . *** *** **:** :

PfHPPD                     VRRGVLTAD-------- 358
Avena_sativa               KSLEVKQSVVAQKS---- 440
Avena_sativa_del_          KSLEVKQSVVAQKS---- 439
Zea_mays                   KSLEAKQAAAAAAQGS 444
Arabidopsis_thaliana       KTLEAKQLVG------- 445
Hordeum_vulgare            KSLEAKQSAAVQGS--- 434
Daucus_carota              KTLEAKQITGSAAA--- 442
Streptomyces_avermitilis   EKRGNL----------- 380
Mycosphaerella_graminicola DLRGNL----------- 419
Coccicoides_immitis        ALRGTLI---------- 399
```

FIG. 1B

HPPD VARIANTS AND METHODS OF USE

CROSS REFERENCE TO RELATED APPLICATIONS

This application is a § 371 National Stage Application of PCT/EP2015/054858, filed Mar. 9, 2015, which claims priority to U.S. Provisional Application No. 62/951,039, filed Mar. 11, 2014 and EP 14159634.6, filed Mar. 13, 2014.

BACKGROUND

Field of the Invention

This invention relates to plant molecular biology, particularly novel HPPD polypeptides that confer improved tolerance to HPPD inhibitor herbicides.

Background of the Invention

The 4-hydroxyphenylpyruvate dioxygenases (HPPDs) are enzymes which catalyze the reaction in which para-hydroxyphenylpyruvate (abbreviated herein as HPP), a tyrosine degradation product, is transformed into homogentisate (abbreviated herein as HG), the precursor in plants of tocopherol and plastoquinone (Crouch N. P. et al. (1997), Tetrahedron, 53, 20, 6993-7010, Fritze et al. (2004), Plant Physiology 134:1388-1400). Tocopherol acts as a membrane-associated antioxidant. Plastoquinone, firstly acts as an electron carrier between PSII and the cytochrome b6/f complex and secondly, is a redox cofactor for phytoene desaturase, which is involved in the biosynthesis of carotenoids.

Up to now, more than 1000 nucleic acid sequences from various organisms present in the NCBI database were annotated as coding for a putative protein having an HPPD domain. But for most of those, it has not been proven that the protein would have an HPPD enzymatic activity either in an in vitro assay or in an in planta approach, nor that such HPPD protein can confer herbicide tolerance to HPPD inhibitor herbicides when expressed in a plant. Several HPPD proteins and their primary sequences have been described in the state of the art, in particular the HPPD proteins of bacteria such as *Pseudomonas* (Rüetschi et al., Eur. J. Biochem., 205, 459-466, 1992, WO96/38567), *Kordia* (WO2011/076889) *Synechococcus* (WO2011/076877), and *Rhodococcus* (WO2011/076892), of protists such as *Blepharisma* (WO2011/076882), of euryarchaeota such as *Picrophilus* (WO2011/076885) of plants such as *Arabidopsis* (WO96/38567, GENBANK® AF047834), carrot (WO 96/38567, GENBANK® 87257), *Avena sativa* (WO2002/046387, WO2011/068567), wheat (WO2002/046387), *Brachiaria platyphylla* (WO2002/046387), *Cenchrus echinatus* (WO2002/046387), *Lolium rigidum* (WO2002/046387), *Festuca arundinacea* (WO2002/046387), *Setaria faberi* (WO 2002/046387), *Eleusine indica* (WO2002/046387), *Sorghum* (WO2002/046387, WO2012/021785), corn (WO2012/021785), *Coccicoides* (GENBANK® COITRP), of *Coptis japonica* (WO2006/132270), *Chlamydomonas reinhardtii* (ES 2275365; WO2011/145015), or of mammals such as mouse or pig.

Inhibition of HPPD leads to uncoupling of photosynthesis, deficiency in accessory light-harvesting pigments and, most importantly, to destruction of chlorophyll by UV-radiation and reactive oxygen species (bleaching) due to the lack of photo protection normally provided by carotenoids (Norris et al. (1995), Plant Cell 7: 2139-2149). Bleaching of photosynthetically active tissues leads to growth inhibition and plant death.

Some molecules which inhibit HPPD, and which inhibit transformation of the HPP into homogentisate while binding specifically to the enzyme, have proven to be very effective herbicides.

At present, most commercially available HPPD inhibitor herbicides belong to one of these chemical families:
1) the triketones, e.g. sulcotrione [i.e. 2-[2-chloro-4-(methylsulfonyl)benzoyl]-1,3-cyclohexanedione], mesotrione [i.e. 2-[4-(methylsulfonyl)-2-nitrobenzoyl]-1,3-cyclohexanedione]; tembotrione [i.e. 2-[2-chloro-4-(methylsulfonyl)-3-[(2,2,2,-trifluoroethoxy)methyl]benzoyl]-1,3-cyclo-hexanedione]; tefuryltrione [i.e. 2-[2-chloro-4-(methylsulfonyl)-3-[[(tetrahydro-2-furanyl)methoxy]methyl]benzoyl]-1,3-cyclohexanedione]]; bicyclopyrone [i.e. 4-hydroxy-3-[[2-[(2-methoxyethoxy)methyl]-6-(trifluoromethyl)-3-pyridinyl]carbonyl]bicyclo[3.2.1]oct-3-en-2-one]; Benzobicyclon [i.e. 3-(2-chloro-4-mesylbenzoyl)-2-phenyl-thiobicyclo[3.2.1]oct-2-en-4-one];
2) the diketonitriles, e.g. 2-cyano-3-cyclopropyl-1-(2-methylsulphonyl-4-trifluoromethylphenyl)-propane-1,3-dione and 2-cyano-1-[4-(methylsulphonyl)-2-trifluoromethylphenyl]-3-(1-methylcyclopropyl)propane-1,3-dione;
3) the isoxazoles, e.g. isoxaflutole [i.e. (5-cyclopropyl-4-isoxazolyl)[2-(methylsulfonyl)-4-(trifluoromethyl)phenyl] methanone]. In plants, isoxaflutole is rapidly metabolized in DKN, a diketonitrile compound which exhibits the HPPD inhibitor property;
4) the pyrazolinates, e.g. topramezone [i.e. [3-(4,5-dihydro-3-isoxazolyl)-2-methyl-4-(methylsulfonyl) phenyl](5-hydroxy-1-methyl-1H-pyrazol-4-yl)methanone], and pyrasulfotole [i.e. (5-hydroxy-1,3-dimethylpyrazol-4-yl(2-mesyl-4-trifluaromethylphenyl)methanone]; pyrazofen [i.e. 2-[4-(2,4-dichlorobenzoyl)-1,3-dimethylpyrazol-5-yloxy] acetophenone];
5) N (1,2,5-oxadiazol-3-yl)benzamides (WO2011/035874) and N-(1,3,4-oxadiazol-2-yl)benzamides (WO2012/126932), eg. 2-methyl-N-(5-methyl-1,3,4-oxadiazol-2-yl)-3-(methylsulfonyl)-4-(trifluoromethyl)benzamide (hereinafter also named "Cmpd. 1");
6) N-(tetrazol-5-yl)- or N-(triazol-3-yl)arylcarboxamides (WO2012/028579), eg. 2-chloro-3-ethoxy-4-(methylsulfonyl)-N-(1-methyl-1H-tetrazol-5-yl)benzamide (hereinafter also named "Cmpd. 2"); 4-(difluoromethyl)-2-methoxy-3-(methylsulfonyl)-N-(1-methyl-1H-tetrazol-5-yl)benzamide (hereinafter also named "Cmpd. 3"); 2-chloro-3-(methylsulfanyl)-N-(1-methyl-1H-tetrazol-5-yl)-4-(trifluoromethyl) benzamide (hereinafter also named "Cmpd. 4"); 2-(methoxymethyl)-3-(methylsulfinyl)-N-(1-methyl-1H-tetrazol-5-yl)-4-(trifluoromethyl)benzamide (hereinafter also named "Cmpd. 5");
7) Pyridazinone derivatives as described in WO2013/050421 and WO2013/083774;
8) Substituted 1,2,5-oxadiazoles as described in WO2013/072300 and WO2013/072402; and
9) Oxoprazin derivatives as described in WO2013/054495.

These HPPD inhibitor herbicides can be used against grass and/or broad leaf weeds in field of crop plants that display metabolic tolerance, such as maize (*Zea mays*), rice (*Oryza Sativa*) and wheat (*Triticum aestivum*) in which they are rapidly degraded (Schulz et al. (1993), FEBS letters, 318, 162-166; Mitchell et al. (2001), Pest Management Science, Vol 57, 120-128; Garcia et al. (2000), Biochem., 39, 7501-7507; Pallett et al. (2001), Pest Management Science, Vol 57, 133-142). In order to extend the scope of use of these HPPD inhibitor herbicides, several efforts have been developed in order to confer to plants, particularly plants without or with an underperforming metabolic tolerance, a tolerance level acceptable under agronomic field conditions.

Besides the attempt of by-passing HPPD-mediated production of homogentisate (U.S. Pat. No. 6,812,010), overexpressing the sensitive enzyme so as to produce quantities of the target enzyme in the plant which are sufficient in relation to the herbicide has been performed (WO96/38567). Overexpression of HPPD resulted in better pre-emergence tolerance to the diketonitrile derivative (DKN) of isoxaflutole (IFT), but the tolerance level was not sufficient for tolerance to post-emergence treatment (Matringe et al. (2005), Pest Management Science 61: 269-276).

A third strategy was to mutate the HPPD in order to obtain a target enzyme which, while retaining its properties of catalyzing the transformation of HPP into homogentisate, is less sensitive to HPPD inhibitors than is the native HPPD before mutation.

This strategy has been successfully applied for the production of plants tolerant to 2-cyano-3-cyclopropyl-1-(2-methylsulphonyl-4-trifluoromethylphenyl)-propane-1,3-dione and to 2-cyano-1-[4-(methylsulphonyl)-2-trifluoromethylphenyl]-3-(1-methylcyclopropyl)propane-1,3-dione (EP496630), two HPPD inhibitor herbicides belonging to the diketonitriles family (WO99/24585). Pro215Leu, Gly336Glu, Gly336Ile, and more particularly Gly336Trp (positions of the mutated amino acid are indicated with reference to the *Pseudomonas fluorescens* HPPD) were identified as mutations which are responsible for an increased tolerance to treatment with these diketonitrile herbicides.

More recently, introduction of a *Pseudomonas fluorescens* HPPD gene into the plastid genome of tobacco and soybean has shown to be more effective than nuclear transformation, conferring tolerance to post-emergence application of isoxaflutole (Dufourmantel et al. (2007), Plant Biotechnol J. 5(1):118-33).

In WO2004/024928, the inventors sought to increase the prenylquinone biosynthesis (e.g., synthesis of plastoquinones, tocopherols) in the cells of plants by increasing the flux of the HPP precursor into the cells of these plants. This has been done by connecting the synthesis of said precursor to the "shikimate" pathway by overexpression of a prephenate dehydrogenase (PDH) enzyme. They have also noted that the transformation of plants with a gene encoding a PDH enzyme and a gene encoding an HPPD enzyme makes it possible to increase the tolerance of said plants to HPPD inhibitors.

In WO2009/144079, nucleic acid sequences encoding an hydroxyphenylpyruvate dioxygenase (HPPD) with specific mutations at position 336 of the *Pseudomonas fluorescens* HPPD protein and their use for obtaining plants which are tolerant to HPPD inhibitor herbicides was disclosed.

In WO2002/046387, several domains of HPPD proteins originating from plants have been identified that may be relevant to confer tolerance to various HPPD inhibitor herbicides but neither in planta nor biochemical data have been shown to confirm the impact of the as described domain functions.

In WO2008/150473, the combination of two distinct tolerance mechanisms—a modified *Avena sativa* gene coding for a mutant HPPD enzyme and a CYP450 Maize monooxygenase (nsf1 gene)—was exemplified in order to obtain an improved tolerance to HPPD inhibitor herbicides, but no data have been disclosed demonstrating the synergistic effects based on the combination of both proteins.

Further, in US2011/0173718, a method to generate plants tolerant to HPPD inhibitors by overexpressing not only a gene coding for a tolerant HPPD, as for example from *Avena sativa*, but also in combination with several plant genes coding for an HST (homogentisate solanesyltransferase) protein is disclosed. However, the level of tolerance to some selected HPPD inhibitor herbicides was rather limited.

In WO2011/094199 and US2011/0185444, the tolerance of several hundred of soybean wild type lines to the HPPD inhibitor isoxaflutole was evaluated. Very few lines displayed reasonable level of tolerance to the herbicides. The putative QTL (quantitative trait loci) responsible for the tolerance was identified. In this region of the genome, a gene coding for an ABC transporter was identified as being the main trait responsible for the improved tolerance to the HPPD inhibitor herbicide observed. However, transgenic plants expressing the identified genes did not display any improvement in tolerance to the tested HPPD inhibitor herbicides.

In WO2010/085705, several mutants of the *Avena sativa* HPPD were disclosed. It was shown that some of the variants displayed improved tolerance in vitro to the triketone "mesotrione", however, only very few mutants were expressed in tobacco plants. Additionally, none of the tobacco plants expressing these mutants displayed improved tolerance to mesotrione or isoxaflutole compared to tobacco plants expressing the wild type *Avena sativa* HPPD gene.

US 2012/0042413 describes polypeptides having HPPD activity but also showing a certain insensitivity to at least one HPPD inhibitor and further suggests a certain set of mutations at different positions of HPPD enzymes and finally discloses biochemical data as well as tolerance levels of plants containing few of such mutated HPPDs. In EP 2453012, several mutants of HPPD have been described; however, the improved tolerance of the described mutants was not demonstrated in planta against several HPPD inhibitor herbicides.

The currently described and partly commercialized HPPD inhibitor herbicides act as slow-binding or slow, tight-binding inhibitors (see Morrison (1982) Trends Biochem. Sci. 7, 102-105). These inhibitors bind slowly (i. e. they have slow rates of association, kon) but no covalently to the HPPD enzyme (i. e. they produce time-dependent inhibition), and are released very slowly (i. e. they have exceptionally slow rates of dissociation, koff) due to their exceedingly tight interaction with the enzyme.
These inhibitors bind so tightly that stoichiometric titrations with the enzyme are possible.

It has become increasingly recognized that the slow-binding or slow, tight-binding inhibitors are not only extraordinary potent HPPD-inhibitors, but, in addition, have features that make them attractive agrochemicals for weed control. The slow rate of dissociation enhances inhibitor effectiveness to such an extent that ideally only one inhibitor molecule per enzyme active site is sufficient to fully inhibit the enzyme's activity and to maintain this level of inhibition for a long time period even in the absence of free inhibitor molecules in the plant cell. This translates into low application rates of these inhibitors to control undesired weeds in crop growing areas.

The properties of slow-binding or slow, tight-binding inhibitors are advantageous when achieving HPPD inhibition and herbicidal activity is the goal. However, these properties are a major disadvantage when HPPD enzymes tolerant to these inhibitors are to be designed. Mutations in the HPPD enzyme that solely reduce the affinity of the inhibitor to the enzyme (pI50) do not fully overcome HPPD inhibition since binding of the inhibitor and inhibition of the HPPD enzyme can still take place and, therefore, the achieved level of inhibition will be maintained for a long time period even in the absence of free inhibitor in the plant cell.

Due to the above described kinetic properties of all the currently described and partly commercialized HPPD inhibitor herbicides, up to now, no HPPD-inhibitor tolerant plants with full tolerance against HPPD-inhibitor herbicides have been achieved, despite the many efforts to generate them.

SUMMARY OF INVENTION

In the present invention, HPPD enzymes and plants containing them showing a full tolerance against several classes of HPPD-inhibitors are described. It turned out that in order to generate such HPPD enzymes with maximized or full tolerance against HPPD-inhibitors it becomes more important to increase the rate of dissociation (koff) of a slow-binding or slow, tight-binding inhibitor than to decrease its affinity to the enzyme (pI50) if inhibitor tolerance is to be achieved. Ideally, reduction of the affinity of an inhibitor to the HPPD enzyme (pI50) and an increase of the rate of dissociation of the inhibitor off the HPPD enzyme (koff) should be achieved simultaneously in a mutant enzyme to obtain a high level of inhibitor tolerance.

In the present invention, this goal was achieved by designing a set of HPPD enzymes which have either no or only a significantly reduced affinity to HPPD inhibitors and, at the same time, the rate of dissociation of the HPPD inhibitors of the enzyme is increased to such an extent that the HPPD inhibitors no longer act as slow-binding or slow, tight-binding inhibitors but, instead of this, have become fully reversible inhibitors.

In the present invention compositions and methods for obtaining HPPD enzymes having the before mentioned characteristics (i.e no or only a significantly reduced affinity to HPPD inhibitors, increased rate of dissociation of the HPPD inhibitors of the enzyme; HPPD inhibitors no longer act as slow-binding or slow, tight-binding inhibitors but have become fully reversible inhibitors) are provided. Compositions include HPPD and isolated, recombinant or chimeric nucleic acid molecules encoding such polypeptides, vectors and host cells comprising those nucleic acid molecules. Compositions also include the antibodies to those polypeptides. The nucleotide sequences can be used in DNA constructs or expression cassettes for transformation and expression in organisms, including microorganisms and plants. The nucleotide sequences may be synthetic sequences that have been designed for expression in an organism including, but not limited to, a microorganism or a plant.

The compositions include nucleic acid molecules encoding herbicide tolerant polypeptides, including nucleic acid molecules encoding a *Pseudomonas fluorescens* HPPD protein having a proline at the amino acid position corresponding to amino acid position 335 of SEQ ID NO:1 and a phenylalanine or a tyrosine at the position corresponding to amino acid position 336 of SEQ ID NO:1 and, optionally, one or more amino acid substitutions at the positions corresponding to amino acid positions 188, 189, 200, 215, 226, 339, and 340 of SEQ ID NO:1, including the HPPD protein set forth in any of SEQ ID NO:7-33 as well as fragments thereof.

Compositions also comprise transformed plants, plant cells, tissues, and seeds that are tolerant to the HPPD inhibitor herbicides by the introduction of the nucleic acid sequence of the invention into the genome of the plants, plant cells, tissues, and seeds. The introduction of the sequence allows for HPPD inhibitor herbicides to be applied to plants to selectively kill HPPD inhibitor sensitive weeds or other untransformed plants, but not the transformed organism. The sequences can additionally be used as a marker for selection of plant cells growing in the presence of one or more HPPD inhibitor herbicides.

Methods for identifying an HPPD enzyme with HPPD inhibitor tolerance activity are additionally provided.

The compositions and methods of the invention are useful for the production of organisms with enhanced tolerance to HPPD inhibitor herbicides. These organisms and compositions comprising the organisms are desirable for agricultural purposes. Plants or seeds comprising the nucleic acid sequence encoding an HPPD according to the invention can be grown in a field and harvested to obtain a plant product. The compositions of the invention are also useful for detecting the presence of HPPD inhibitor herbicide tolerant proteins or nucleic acids in products or organisms.

BRIEF DESCRIPTION OF THE FIGURES

FIG. 1 shows an alignment of amino acid sequence of HPPDs from microbial and plant species, including *Pseudomonas fluorescens* (Pf, SEQ ID NO:1), *Avena sativa* (SEQ ID NO:38), a variant of the HPPD from *Avena sativa* (SEQ ID NO:39), *Zea mays* (SEQ ID NO:40), *Streptomyces avermitilis* (SEQ ID NO:44), *Arabidopsis thaliana* (SEQ ID NO:41), *Hordeum vulgare* (SEQ ID NO:42), *Daucus carota* (SEQ ID NO:43), *Mycosphaerella graminicola* (SEQ ID NO:45), and *Coccicoides immitis* (SEQ ID NO:46).

DETAILED DESCRIPTION OF THE INVENTION

Figure 2A:
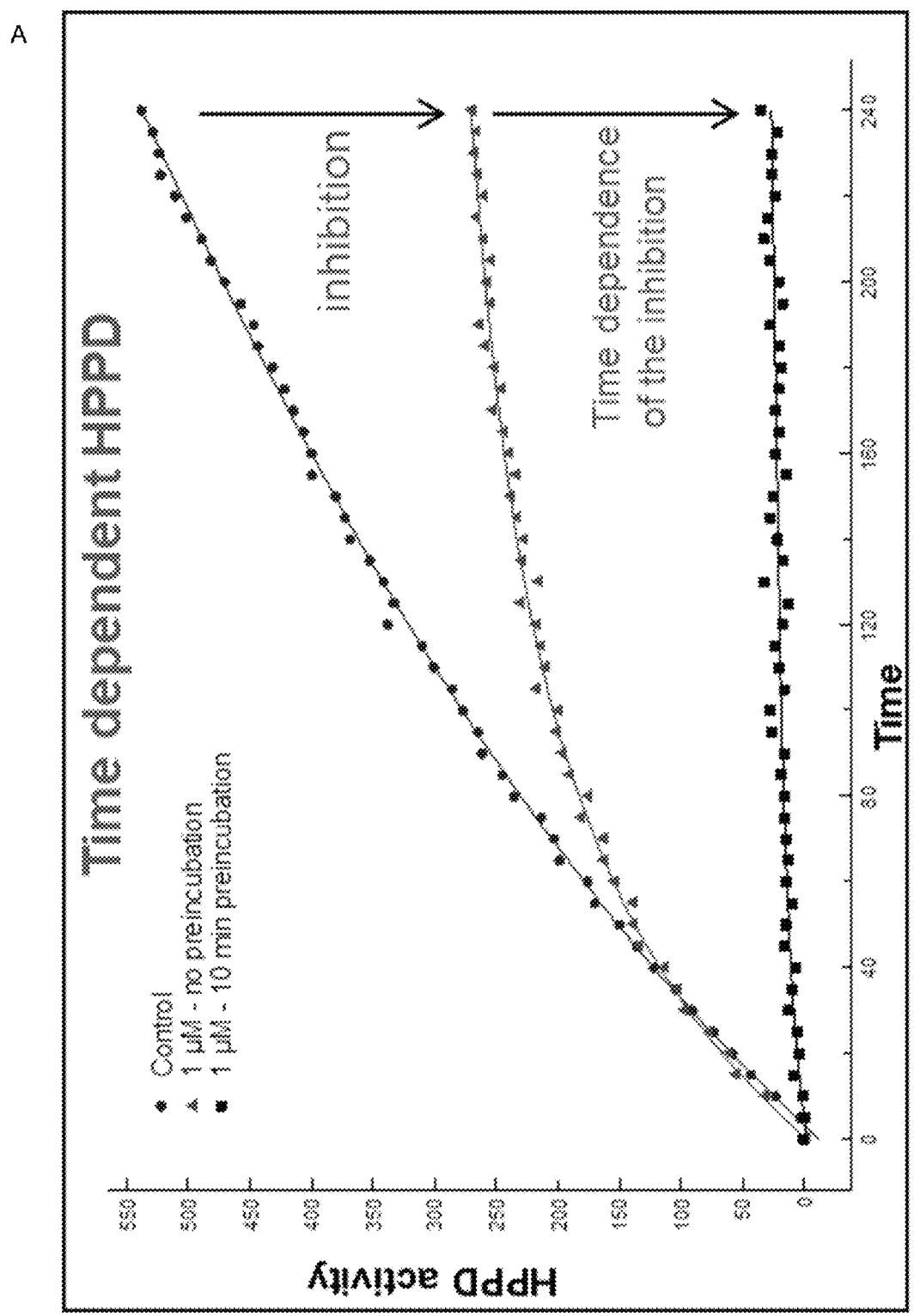
FIG. 2A shows an example of time dependent inhibition of a time dependent HPPD mutant enzyme, in presence of 1 µM HPPD inhibitor.
Figure 2B:
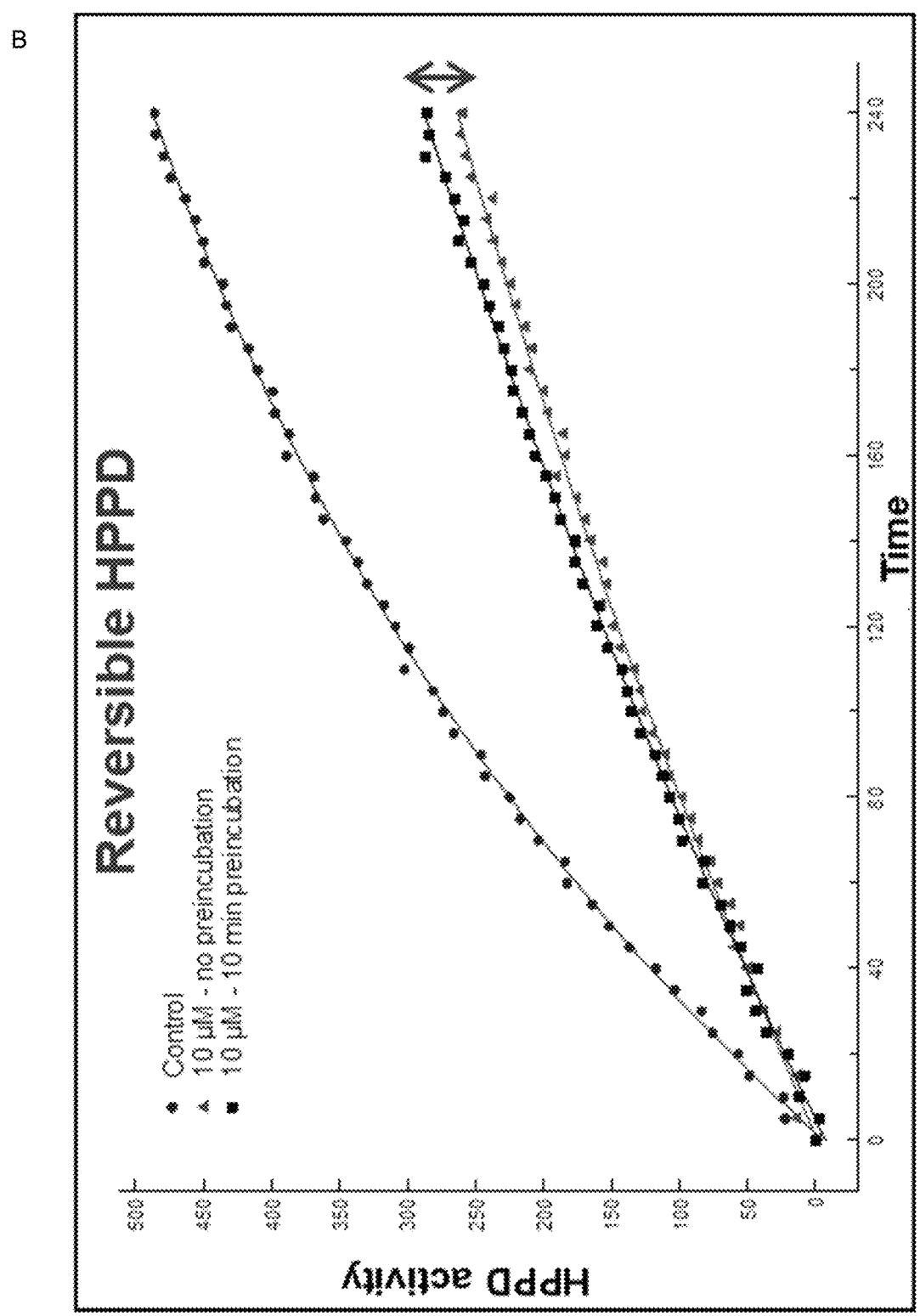
FIG. 2B shows an example of reversible inhibition of a reversible HPPD mutant enzyme in presence of 10 µM inhibitor.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Overview

Several efforts have been developed in order to confer to plants an agronomically-acceptable level of tolerance to a broad range of HPPD inhibitor herbicides, including bypassing HPPD-mediated production of homogentisate (U.S. Pat. No. 6,812,010), overexpressing the sensitive enzyme so as to produce quantities of the target enzyme in the plant which are sufficient in relation to the herbicide (WO96/38567), and mutating the HPPD in order to obtain a target enzyme which, while retaining its properties of catalyzing the transformation of HPP into homogentisate, is less sensitive to HPPD inhibitors than is the native HPPD before mutation.

Despite these successes obtained for the development of plants showing tolerance to several HPPD inhibitors herbicides described above, it is still necessary to develop and/or improve the tolerance of plants to newer or to several different HPPD inhibitors, particularly HPPD inhibitors belonging to the classes of the triketones (e.g. sulcotrione, mesotrione, tembotrione, benzobicyclon and bicyclopyrone), the pyrazolinates (e.g., topramezone and pyrasulfotole), N-(1,2,5-Oxadiazol-3-yl)benzamides (WO2011/035874), N-(tetrazol-4-yl)- or N-(triazol-3-yl) arylcarboxamides (WO2012/028579), pyridazinone derivatives (WO2013/050421 and WO2013/083774); substituted 1,2,5-oxadiazoles (WO2013/072300 and WO2013/072402); and oxoprazin derivatives (WO2013/054495).

Thus, the present invention provides improved compositions and methods for regulating HPPD inhibitor herbicide tolerance. HPPD inhibitor herbicides like those of the class of N (1,2,5-oxadiazol-3-yl)benzamides; N-(tetrazol-4-yl)- or N-(triazol-3-yl)arylcarboxamides, such as 2-chloro-3-ethoxy-4-(methylsulfonyl)-N-(1-methyl-1H-tetrazol-5-yl) benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, such as 2-chloro-3-ethoxy-4-(methylsulfonyl)-N-(1-methyl-1H-tetrazol-5-yl) benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, such as tembotrione, sulcotrione and mesotrione; the class of isoxazoles such as isoxaflutole; or of the class of pyrazolinates, such as pyrasulfotole and topramezone, have an outstanding herbicidal activity against a broad spectrum of economically important monocotyledonous and dicotyledonous annual harmful plants. The active substances also act efficiently on perennial harmful plants which produce shoots from rhizomes, wood stocks or other perennial organs and which are difficult to control. Within the meaning of the present invention, "herbicide" is understood as being a herbicidally active substance on its own or such a substance which is combined with an additive which alters its efficacy, such as, for example, an agent which increases its activity (a synergistic agent) or which limits its activity (a safener). The herbicide may further comprise solid or liquid adjuvants or carriers that are ordinarily employed in formulation technology (e.g. natural or regenerated mineral substances, solvents, dispersants, wetting agents, tackifiers, emulsifiers, growth promoting agents, and the like), as well as one or more additional herbicides and/or one or more pesticides (e.g., insecticides, virucides, microbicides, amoebicides, pesticides, fungicides, bactericides, nematicides, molluscicides, and the like).

The methods involve transforming organisms with nucleotide sequences encoding an HPPD inhibitor tolerance gene of the invention or otherwise introducing such HPPD inhibitor tolerance genes in organisms not containing them (e.g., by mating, cell fusion, or by crossing organisms containing an introduced HPPD inhibitor gene of the invention with organisms not containing it and obtaining progeny containing such gene). The nucleotide sequences of the invention are useful for preparing plants that show increased tolerance to HPPD inhibitor herbicides, particularly increased tolerance to HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone. The HPPD inhibitor herbicide tolerance gene of the invention may also show tolerance towards the "coumarone-derivative herbicides" (described in WO2009/090401, WO2009/090402, WO2008/071918, WO2008/009908). In this regard, any one of the HPPD inhibitor herbicide tolerance genes of the invention can also be expressed in a plant also expressing a chimeric homogentisate solanesyltransferase (HST) gene or a mutated HST gene as described in WO2011/145015, WO2013/064987, WO2013/064964, or WO2010/029311, to obtain plants tolerant to HST inhibitor herbicides. As used herein, a "coumarone-derivative herbicide" or "HST inhibitor herbicide" encompasses compounds which fall under the IUPAC nomenclature of 5H-thiopyrano [4,3-b]pyridin-8-ol, 5H-thiopyrano[3,4-b]pyrazin-8-ol, oxathiino[5,6-b]pyridin-4-ol, and oxathiino[5, 6-b]pyrazin-4-ol.

Thus, by "HPPD inhibitor herbicide tolerance" gene of the invention is intended a gene encoding a protein that confers upon a cell or organism the ability to tolerate a higher concentration of an HPPD inhibitor herbicide than such cell or organism that does not express the protein, or to tolerate a certain concentration of an HPPD inhibitor herbicide for a longer time than such cell or organism that does not express the protein, or that confers upon a cell or organism the ability to perform photosynthesis, grow, and/or reproduce with less damage or growth inhibition observed than such cell or organism not expressing such protein. An "HPPD inhibitor tolerance protein" includes a protein that confers upon a cell or organism the ability to tolerate a higher concentration of HPPD inhibitor herbicide than such cell or organism that does not express the protein, or to tolerate a certain concentration of HPPD inhibitor herbicide for a longer period of time than such cell or organism that does not express the protein, or that confers upon a cell or organism the ability to perform photosynthesis, grow, and/or reproduce with less damage or growth inhibition observed than such cell or organism not expressing such protein. By "tolerate" or "tolerance" is intended either to survive a particular HPPD inhibitor herbicide application, or the ability to carry out essential cellular functions such as photosynthesis, protein synthesis or respiration and reproduction in a manner that is not readily discernable from untreated cells or organisms, or the ability to have no significant difference in yield or even improved yield for plants treated with HPPD inhibitor herbicide compared to such plants not treated with such herbicide (but where weeds have been removed or prevented by a mechanism other than application of the HPPD inhibitor herbicide, such as the methods described in WO2011/100302, which is herein incorporated by reference in its entirety).

In addition to conferring upon a cell HPPD inhibitor tolerance, the HPPD nucleic acid sequences of the invention encode polypeptides having HPPD activity, i. e., catalyzing the reaction in which para-hydroxyphenylpyruvate (HPP) is transformed into homogentisate. The catalytic activity of an HPPD enzyme may be defined by various methods well-known in the art. WO2009/144079 describes various suitable screening methods.

The enzymatic activity of HPPD proteins can be measured by any method that makes it possible either to measure the decrease in the amount of the HPP or $O_2$ substrates, or to measure the accumulation of any of the products derived from the enzymatic reaction, i.e. homogentisate or $CO_2$. In particular, the HPPD activity can be measured by means of the method described in WO2009/144079; Garcia et al. (1997), Biochem. J. 325, 761-769; Garcia et al. (1999), Plant Physiol. 119, 1507-1516; or in WO2012/021785, which are incorporated herein by reference.

For the purposes of the present invention, a "reference" HPPD protein (or HPPD gene) is any HPPD protein or nucleic acid against which the HPPD protein or HPPD nucleic acid of the invention is being compared. For the purposes of describing the HPPD proteins of the present invention, the terms "protein" and "polypeptide" are used interchangeably. This reference HPPD can be a native plant, bacterial, or animal HPPD, or can be a mutated HPPD that is known in the art such as the PfP215L and PfG336F mutants described in International Patent Publication WO2009/144079 and set forth herein as SEQ ID NO:20 and 2, respectively, or can be either of the PfHPPDevo33, PfHPPDevo36, PfHPPDevo37, PfHPPDevo40, or PfHPPDevo41 proteins set forth herein as SEQ ID NO:6, and 34-37, respectively, which are also described in International Patent Application No, PCT/US2013/59598, filed Sep. 13, 2013, and which is herein incorporated by reference. Such reference HPPD can be used to determine whether the HPPD protein or nucleic acid of the invention has a particular property of interest (e.g., improved, comparable or decreased HPPD inhibitor herbicide tolerance or HPPD enzyme activity; improved, comparable or decreased expression in a host cell; improved, comparable or decreased protein stability, and the like).

In various embodiments herein, the HPPD inhibitor herbicide tolerant protein encoded by a nucleic acid (including isolated, recombinant and chimeric genes thereof, vectors, host cells, plants, plant parts, and seeds comprising the nucleic acid, HPPD polypeptides and compositions thereof encoded by the nucleic acid, as well as methods of using the protein encoded by the nucleic acid for increasing tolerance of a plant to HPPD inhibitor herbicides, particularly increased tolerance to HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone) has a proline at the amino acid position corresponding to amino acid position 335 of SEQ ID NO:1 and a phenylalanine or a tyrosine at the position corresponding to amino acid position 336 of SEQ ID NO:1 and, optionally, one or more amino acid substitutions at the positions corresponding to amino acid positions 188, 189, 200, 215, 226, 339, and 340 of SEQ ID NO:1, including the HPPD proteins set forth in any of SEQ ID NO:7-33. By "corresponding to" is intended the nucleotide or amino acid position relative to that position in SEQ ID NO:1 when two (or more) sequences are aligned using standard alignment algorithms described elsewhere herein. A representative alignment of SEQ ID NO:1 with HPPD amino acid sequences from various microbial and plant species is shown in FIG. 1. For example, amino acid positions 188, 215, 335, 336, 339, and 340 of SEQ ID NO:1 correspond to amino acid positions 241, 271, 412, 413, 416, and 417, respectively, of the HPPD from *Avena sativa* (SEQ ID NO:38); to amino acid positions 235, 265, 406, 407, 410, and 411, respectively, of the HPPD from *Hordeum vulgare* (SEQ ID NO:42) and to amino acid positions 242, 272, 413, 414, 417, and 418, respectively, of the HPPD from *Zea mays* (SEQ ID NO:40). An alignment of numerous HPPD amino acid sequences from various species is also found in Tables 2a and 2b of European Patent Publication No. EP2453012, which is herein incorporated by reference. Accordingly, depending on the length of the concerned HPPD amino acid sequence, having either additional or fewer residues than the sequence of SEQ ID NO:1, the corresponding position can be located at a position different from positions 188, 189, 200, 215, 226, 335, 336, 339, and 340 in such concerned HPPD protein.

In one embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising a proline at the amino acid position corresponding to amino acid position 335 of SEQ ID NO:1 and a phenylalanine or a tyrosine at the position corresponding to amino acid position 336 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and a phenylalanine or a tyrosine at the position corresponding to amino acid position 336 of SEQ ID NO:1 and
ii. an alanine, arginine, asparagine, aspartic acid, cysteine, glutamic acid, glutamine, glycine, histidine, isoleucine, leucine, lysine, methionine, phenylalanine, serine, threonine, tryptophan, tyrosine, or valine at the amino acid position corresponding to amino acid position 188 of SEQ ID, NO:1; and
iii. an alanine, arginine, asparagine, aspartic acid, cysteine, glutamic acid, glutamine, glycine, histidine, leucine, lysine, methionine, phenylalanine, serine, threonine, tryptophan, tyrosine, or valine at the amino acid position corresponding to amino acid position 189 of SEQ ID NO:1; and
iv. an isoleucine, leucine, or methionine at the amino acid position corresponding to amino acid position 200 of SEQ ID NO:1; and
v. an alanine, leucine, proline, or asparagine at the amino acid position corresponding to amino acid position 215 of SEQ ID NO:1; and
vi. a histidine or glutamine at the amino acid position corresponding to amino acid position 226 of SEQ ID NO:1; and
vii. a histidine, isoleucine, leucine, methionine, glutamine, arginine, alanine, lysine, serine, threonine, or valine at the amino acid position corresponding to amino acid position 339 of SEQ ID NO:1; and
viii. an alanine, arginine, asparagine, aspartic acid, cysteine, glutamic acid, glutamine, glycine, histidine, isoleucine, leucine, lysine, methionine, phenylalanine, serine, threonine, tryptophan, tyrosine, or valine at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and a phenylalanine or a tyrosine at the position corresponding to amino acid position 336 of SEQ ID NO:1 and
ii. an alanine, glycine, histidine, serine, or tryptophan at the amino acid position corresponding to amino acid position 188 of SEQ ID, NO:1; and
iii. an arginine, cysteine, glutamine, glutamic acid, aspartic acid, glycine, histidine, phenylalanine, or serine at the amino acid position corresponding to amino acid position 189 of SEQ ID NO:1; and
iv. an isoleucine, leucine, or methionine at the amino acid position corresponding to amino acid position 200 of SEQ ID NO:1; and
v. an alanine, leucine, proline, or asparagine at the amino acid position corresponding to amino acid position 215 of SEQ ID NO:1; and
vi. a histidine or glutamine at the amino acid position corresponding to amino acid position 226 of SEQ ID NO:1; and vii. a serine, alanine, threonine, glutamine or lysine at the amino acid position corresponding to amino acid position 339 of SEQ ID NO:1; and
viii. an alanine, arginine, aspartic acid, glutamic acid, glutamine, glycine, or leucine at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and a phenylalanine or a tyrosine at the position corresponding to amino acid position 336 of SEQ ID NO:1 and
ii. an alanine or glycine at the amino acid position corresponding to amino acid position 188 of SEQ ID. NO:1; and
iii. an arginine, cysteine, glutamic acid, aspartic acid, or glycine at the amino acid position corresponding to amino acid position 189 of SEQ ID NO:1; and
iv. an isoleucine, leucine, or methionine at the amino acid position corresponding to amino acid position 200 of SEQ ID NO:1; and
v. an alanine, leucine, proline, or asparagine at the amino acid position corresponding to amino acid position 215 of SEQ ID NO:1; and
vi. a histidine or glutamine at the amino acid position corresponding to amino acid position 226 of SEQ ID NO:1; and
vii. an alanine or lysine at the amino acid position corresponding to amino acid position 339 of SEQ ID NO:1; and
viii. an alanine, glutamic acid, glutamine, or glycine at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
  a. a phenylalanine at the position corresponding to amino acid position 336 of SEQ ID NO:1 or
  b. a tyrosine at the position corresponding to amino acid position 336 of SEQ ID NO:1 and
ii. an alanine at the amino acid position corresponding to amino acid position 339 of SEQ ID NO:1; and
iii. a glutamine at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising a proline at the amino acid position corresponding to amino acid position 335 of SEQ ID NO:1 and
  a. a phenylalanine at the position corresponding to amino acid position 336 of SEQ ID NO:1 or b. a tyrosine at the position corresponding to amino acid position 336 of SEQ ID NO:1 and a glutamic acid at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
  a. a phenylalanine at the position corresponding to amino acid position 336 of SEQ ID NO:1 or
  b. a tyrosine at the position corresponding to amino acid position 336 of SEQ ID NO:1 and
ii. a leucine at the amino acid position corresponding to amino acid position 215 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
  a. a phenylalanine at the position corresponding to amino acid position 336 of SEQ ID NO:1 or
  b. a tyrosine at the position corresponding to amino acid position 336 of SEQ ID NO:1 and
ii. a leucine at the amino acid position corresponding to amino acid position 215 of SEQ ID NO:1 and
iii. a glutamic acid at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
  a. a phenylalanine at the position corresponding to amino acid position 336 of SEQ ID NO:1 or
  b. a tyrosine at the position corresponding to amino acid position 336 of SEQ ID NO:1 and
ii. glycine at the amino acid position corresponding to amino acid position 188 of SEQ ID NO:1 and
iii. a cysteine at the amino acid position corresponding to amino acid position 189 of SEQ ID NO:1 and
iv. a leucine at the amino acid position corresponding to amino acid position 215 of SEQ ID NO:1 and
v. a glutamic acid at the amino acid position corresponding to amino acid position 340 of SEQ ID NO:1

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
  a. a phenylalanine at the position corresponding to amino acid position 336 of SEQ ID NO:1 or
  b. a tyrosine at the position corresponding to amino acid position 336 of SEQ ID NO:1 and
ii. glycine at the amino acid position corresponding to amino acid position 188 of SEQ ID NO:1 and
iii. a cysteine at the amino acid position corresponding to amino acid position 189 of SEQ ID NO:1 and
iv. a glutamic acid at the amino acid position corresponding to amino acid position 340 of SEQ ID NO:1

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
  a. a phenylalanine at the position corresponding to amino acid position 336 of SEQ ID NO:1 or
  b. a tyrosine at the position corresponding to amino acid position 336 of SEQ ID NO:1 and
ii. an asparagine at the amino acid position corresponding to amino acid position 215 of SEQ ID NO:1 and
iii. a glutamic acid at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
  a. a phenylalanine at the position corresponding to amino acid position 336 of SEQ ID NO:1 or
  b. a tyrosine at the position corresponding to amino acid position 336 of SEQ ID NO:1 and
ii. an alanine at the amino acid position corresponding to amino acid position 215 of SEQ ID NO:1 and
iii. a glutamic acid at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
  a. a phenylalanine at the position corresponding to amino acid position 336 of SEQ ID NO:1 or
  b. a tyrosine at the position corresponding to amino acid position 336 of SEQ ID NO:1 and
ii. a leucine at the amino acid position corresponding to amino acid position 215 of SEQ ID NO:1 and
iii. a glycine at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
   a. a phenylalanine at the position corresponding to amino acid position 336 of SEQ ID NO:1 or
   b. a tyrosine at the position corresponding to amino acid position 336 of SEQ ID NO:1 and
ii. an isoleucine at the amino acid position corresponding to amino acid position 200 of SEQ ID NO:1 and
iii. a leucine at the amino acid position corresponding to amino acid position 215 of SEQ ID NO:1 and
iv. a glutamic acid at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
   a. a phenylalanine at the position corresponding to amino acid position 336 of SEQ ID NO:1 or
   b. a tyrosine at the position corresponding to amino acid position 336 of SEQ ID NO:1 and
ii. an isoleucine at the amino acid position corresponding to amino acid position 200 of SEQ ID NO:1 and
iii. a glutamic acid at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
   a. a phenylalanine at the position corresponding to amino acid position 336 of SEQ ID NO:1 or
   b. a tyrosine at the position corresponding to amino acid position 336 of SEQ ID NO:1 and
ii. an methionine at the amino acid position corresponding to amino acid position 200 of SEQ ID NO:1 and
iii. a glutamic acid at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
   a. a phenylalanine at the position corresponding to amino acid position 336 of SEQ ID NO:1 or
   b. a tyrosine at the position corresponding to amino acid position 336 of SEQ ID NO:1 and
ii. a methionine at the amino acid position corresponding to amino acid position 200 of SEQ ID NO:1 and
iii. a leucine at the amino acid position corresponding to amino acid position 215 of SEQ ID NO:1 and
iv. a glutamic acid at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
   a. a phenylalanine at the position corresponding to amino acid position 336 of SEQ ID NO:1 or
   b. a tyrosine at the position corresponding to amino acid position 336 of SEQ ID NO:1 and
ii. a leucine at the amino acid position corresponding to amino acid position 215 of SEQ ID NO:1 and
iii. an histidine at the amino acid position corresponding to amino acid position 226 of SEQ ID NO:1 and
iv. a glutamic acid at the amino acid position corresponding to amino acid position 340 of SEQ ID NO:1.

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
   a. a phenylalanine at the position corresponding to amino acid position 336 of SEQ ID NO:1 or
   b. a tyrosine at the position corresponding to amino acid position 336 of SEQ ID NO:1 and
ii. glycine at the amino acid position corresponding to amino acid position 188 of SEQ ID NO:1 and
iii. a cysteine at the amino acid position corresponding to amino acid position 189 of SEQ ID NO:1 and
iv. a asparagine at the amino acid position corresponding to amino acid position 215 of SEQ ID NO:1 and
v. a glutamic acid at the amino acid position corresponding to amino acid position 340 of SEQ ID NO:1

In another embodiment, the HPPD of the present invention (including the nucleotide sequence encoding it and recombinant and chimeric genes thereof, vectors, host cells, plants, plant parts, and seeds comprising the nucleotide sequence encoding the HPPD of the invention) consists of an amino acid sequence comprising
i. a proline at the amino acid position corresponding to amino acid position 335 of SEQ ID NO:1 and
   a. a phenylalanine at the position corresponding to amino acid position 336 of SEQ ID NO:1 or
   b. a tyrosine at the position corresponding to amino acid position 336 of SEQ ID NO:1 and
ii. a histidine at the amino acid position corresponding to amino acid position 226 of SEQ ID NO:1 and
iii. a glutamic acid at the amino acid position corresponding to amino acid position 340 of SEQ ID NO:1.

The relevant amino acid position of the reference HPPD proteins and of the HPPD proteins according to the invention comprising one or more amino acid substitutions are summarized in Table 1.

TABLE 1

Amino acid substitutions of the reference HPPD proteins and the HPPD proteins according to the invention relative to SEQ ID NO: 1, also containing the clone identifier number column 1 and the respective SEQ ID NO according to the sequence protocol and the references in the description. In case of open boxes, the wild-type amino acid sequence (PfHPPD) is present at this position.

| Clone | SEQ ID NO: | 188 | 189 | 200 | 215 | 226 | 335 | 336 | 339 | 340 |
|---|---|---|---|---|---|---|---|---|---|---|
| PfHPPD | 1 | A | R | L | P | Q | E | G | K | A |
| PfG336F | 2 | | | | | | | F | | |
| PfG336Y | 3 | | | | | | | Y | | |
| PfG336W | 4 | | | | | | | W | | |
| C959 | 5 | | | | | | P | | | |
| PfEvo33 | 6 | | | | | | P | W | | |
| PfEvo43 | 7 | | | | | | P | F | | |
| PfEvo44 | 8 | | | | | | P | Y | | |
| FLP129 | 9 | | | | | | P | F | A | Q |
| FLP130 | 10 | | | | | | P | F | | E |
| FLP136 | 11 | | | | L | | P | F | | |
| FLP202 | 12 | | | | L | | P | F | | E |
| K131 | 13 | | | | | | P | Y | A | Q |
| K132 | 14 | | | | | | P | Y | | E |
| K137 | 15 | | | | L | | P | Y | | |
| K203 | 16 | | | | L | | P | Y | | E |
| K250 | 17 | G | C | | L | | P | F | | E |
| K255 | 18 | | | | A | | P | F | | E |
| K258 | 19 | | | | N | | P | F | | E |
| K299 | 20 | | | | L | | | | | |
| K300 | 21 | | | | L | | P | F | | G |
| K303 | 22 | | | I | L | | P | F | | E |
| K304 | 23 | | | M | L | | P | F | | E |
| K306 | 24 | | | | L | H | P | F | | E |
| K325 | 25 | G | C | | N | | P | F | | E |
| K357 | 26 | G | C | | | | P | F | | E |
| K360 | 27 | | | I | | | P | F | | E |
| K361 | 28 | | | M | | | P | F | | E |
| K363 | 29 | | | | | H | P | F | | E |
| K405 | 30 | G | C | | A | | P | F | | E |
| K406 | 31 | G | G | | N | | P | F | | E |
| K407 | 32 | G | E | | N | | P | F | | E |
| K408 | 33 | G | D | | N | | P | F | | E |

In another embodiment, HPPD proteins according to the invention has at least 53%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence set forth herein as SEQ ID NO:1.

Exemplary HPPD sequences that can be modified according to the present invention include those from bacteria, for example, of the *Pseudomonas* sp. type, or otherwise cyanobacteria, for example of the *Synechocystis* genus. The sequence can also be of plant origin, in particular derived from dicotyledonous plants or monocotyledonous plants. Advantageous examples which may be cited are plants such as tobacco, *Arabidopsis thaliana* (WO96/38567), *Daucus carota* (WO96/38567), *Zea mays* (corn, WO2012/021785), wheat (*Triticum aestivum*, WO2002/046387), barley (EP2453012), *Avena sativa* (WO2002/046387/WO2011/068567), *Brachiaria platyphylla* (WO2002/046387), *Cenchrus echinatus* (WO2002/046387), *Lolium rigidum* (WO2002/046387), *Festuca arundinacea* (WO2002/046387), *Setaria faberi* (WO2002/046387), *Eleusine indica* (WO2002/046387), or *Sorghum* (WO2002/046387, WO2012/021785). In a particular embodiment of the invention, the HPPD that can be modified according to the present invention is from a bacterial or protist origin, particularly from *Pseudomonas* sp., more particularly from *Pseudomonas fluorescens*, *Pseudomonas putida*, *Pseudomonas aeruginosa*, *Pseudomonas testosteroni* (*Comamonas testosteroni*), *Rhodococcus* sp. (WO2011/076892), *Blepharisma japonicum* (WO2011/076882), *Synechococcus* sp. (WO2011/076877), *Kordia algicida* (WO2011/076889), from the euryarchaeoate *Picrophilus torridus* (WO2011/076885), or from a plant origin, including from *Arabidopsis thaliana*, *Sorghum bicolor*, *Oryza sativa*, *Triticum aestivum*, *Hordeum vulgare*, *Lolium rigidum*, or *Avena sativa*.

For the purposes of the present invention, the HPPD of the invention may also comprise further modifications, for example, wherein some amino acids (e.g., 1 to 10 amino acids) have been replaced, added or deleted for cloning purposes, to make a transit peptide fusion, and the like, which retains HPPD activity, i.e. the property of catalyzing the conversion of para-hydroxyphenylpyruvate to homogentisate, or can be any HPPD that can be further improved. For example, the HPPD that can be further improved by the modifications described herein can be the variant HPPD derived from *Pseudomonas fluorescens* set forth herein as any of SEQ ID NO:34-37, the variant HPPD from *Avena sativa* set forth herein as SEQ ID NO:38, the variant HPPD sequences set forth in any of SEQ ID NO:3-326, 383-389, 393, 395, and 397-459 in WO2012/021785, which is herein incorporated by reference in its entirety; the HPPD sequences set forth in any of SEQ ID NO:2-14 and 20-50 of WO2011/068567, which is herein incorporated by reference in its entirety; the HPPD sequences set forth in any of SEQ ID NO:15-26 of WO2010/085705, which is herein incorporated by reference in its entirety; an HPPD having one or more of the substitutions described in WO2009/144079 or U.S. Pat. No. 6,245,968, each of which is herein incorporated by reference in its entirety; an HPPD having one or more of the substitutions described in Tables 1, 2, 5, or 6 of WO2010/085705; and/or an HPPD having one or more of the substitutions described in Table 1 of WO2011/068567.

In some embodiments, the nucleotide sequence of the invention (including isolated, recombinant and chimeric genes thereof, vectors, host cells, plants, plant parts, and seeds comprising the nucleic acid sequence, amino acid sequences and compositions thereof encoded by the nucleic acid sequence, as well as methods of using the nucleic acid sequence for increasing tolerance of a plant to HPPD inhibitor herbicides, particularly increased tolerance to HPPD inhibitor herbicides of the class of N (1,2,5-oxadiazol-3-yl)benzamides; N-(tetrazol-4-yl)- or N-(triazol-3-yl) arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl) benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4)t 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone) encodes the amino acid sequence set forth in any one of SEQ ID NO:7-33, and fragments and variants thereof that encode a HPPD inhibitor herbicide tolerance polypeptide.

A. Methods for Measuring HPPD Inhibitor Tolerance

Any suitable method for measuring tolerance to HPPD inhibitor herbicides can be used to evaluate the HPPD sequences of the invention. Tolerance can be measured by monitoring the ability of a cell or organism to survive a particular HPPD inhibitor herbicide application, or the ability to carry out essential cellular functions such as photosynthesis, protein synthesis or respiration and reproduction in a manner that is not readily discernable from untreated cells or organisms, or the ability to have no significant difference in yield or even improved yield for plants treated with HPPD inhibitor herbicide compared to such plants not treated with such herbicide (but where weeds have been removed or prevented by a mechanism other than application of the HPPD inhibitor herbicide). In some embodiments, tolerance can be measured according to a visible indicator phenotype of the cell or organism transformed with a nucleic acid comprising the gene coding for the respective HPPD protein, or in an in vitro assay of the HPPD protein, in the presence of different concentrations of the various HPPD inhibitors. Dose responses and relative shifts in dose responses associated with these indicator phenotypes (formation of brown color, growth inhibition, bleaching, herbicidal effect etc.) are conveniently expressed in terms, for example, of GR50 (concentration for 50% reduction of growth) or MIC (minimum inhibitory concentration) values where increases in values correspond to increases in inherent tolerance of the expressed HPPD, in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed HPPD. Herbicides can suitably be applied pre-emergence or post emergence.

In various embodiments, tolerance level of the nucleic acid or gene encoding an HPPD protein according to the invention, or the HPPD protein of the invention can be screened via transgenesis, regeneration, breeding and spray testing of a test plant such as tobacco, or a crop plant such as soybean, corn, or cotton. In line with the results obtained by such screening, such plants are more tolerant, desirably tolerant to at least 2 times the normal dose recommended for field applications, even more preferably tolerant up to 4 times the normal dose recommended for field applications, to HPPD inhibitor herbicides (e.g., HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone) than such plants that do not contain any exogenous gene encoding an HPPD protein, or than plants that contain a gene comprising a reference HPPD-encoding DNA, for example, a *Pseudomonas* fluorescens HPPD-encoding DNA, under control of the same promoter as the nucleic acid encoding the HPPD protein of the invention. Accordingly, the term "capable of increasing the tolerance of a plant to at least one herbicide acting on HPPD" denotes a tolerance by the plant expressing the HPPD of the invention to at least 1×, 2×, or 3×, or 4×, or greater, the normal field dose of the HPPD inhibitor herbicide as compared to a plant only expressing its endogenous HPPD or a plant expressing a reference HPPD enzyme. In this regard, the term "herbicide acting on HPPD" is not limited to substances which are known and/or used as herbicides but to any substances which inhibit the catalytic activity of HPPD proteins.

Alternatively, at the quantitative level data like $pI_{50}$ ($pI_{50}$-value means the log value of the concentration of inhibitor necessary to inhibit 50% of the enzyme activity in molar concentration) can be obtained for the HPPD protein of the invention and compared to a reference HPPD sequence in presence or absence of any respective HPPD inhibitor herbicide.

A specific, although non-limiting, type of assay that can be used to evaluate the HPPD sequences of the invention is a colorimetric assay. In this assay, a YT-broth-type culture medium with 1% agarose, 5 mM L-Tyrosine and 42 mM Succinate, which contains the selection agent for the vector pSE420 (Invitrogen, Karlsruhe, Germany) or a modified version of pSE420 (pSE420(RI)NX) is poured into deep well plates. E. coli culture in the exponential growth phase which contains the vector pSE420-HPPDx (HPPDx means any gene coding for a putative HPPD enzyme/protein) is applied to each well. After 16 hours at 37° C., the wells which do not contain the culture medium, those which have been seeded with an E. coli culture containing the empty vector pSE420 are transparent, or those which have been seeded with an E. coli culture containing a vector pSE420-HPPDx containing a gene coding for an inactive HPPD are transparent, while the wells seeded with an E. coli culture containing the vector pSE420-HPPDx coding for an active HPPD are brown. It has been previously demonstrated that this test reflects the HPPD activity, whatever the origin of this activity is, and allows the identification of HPPD activities (U.S. Pat. No. 6,768,044), i.e. at a qualitative level.

B. Methods of Introducing Mutations into HPPD Sequences

In the mutated HPPD protein encoded by the nucleic acid of the invention at least one amino acid has been replaced as defined above.

The replacement can be effected in the nucleic acid sequence which encodes the reference HPPD as defined above by any means which is appropriate for replacing, in the said sequence, the codon which encodes the amino acid to be replaced with the codon which corresponds to the amino acid which is to replace it, with the said codons being widely described in the literature and well known to the skilled person.

Several molecular biological methods can be used to achieve this replacement. A useful method for preparing a mutated nucleic acid sequence according to the invention and the corresponding protein comprises carrying out site-directed mutagenesis on codons encoding one or more amino acids which are selected in advance. The methods for obtaining these site-directed mutations are well known to the skilled person and widely described in the literature (in particular: Directed Mutagenesis: A Practical Approach, 1991, Edited by M. J. McPHERSON, IRL PRESS), or are methods for which it is possible to employ commercial kits (for example the QUIKCHANGE™ lightening mutagenesis kit from Qiagen or Stratagene). After the site-directed mutagenesis, it is useful to select the cells which contain a mutated HPPD which is less sensitive to an HPPD inhibitor by using an appropriate screening aid. Appropriate screening methods to achieve this have been described above.

Alternatively, a DNA sequence encoding the reference HPPD can be modified in silico to encode an HPPD protein having one or more of the substitutions recited herein, and then synthesized de novo. The nucleotide sequence encoding the mutated HPPD protein can be introduced into a host cell as described elsewhere herein.

C. Isolated Polynucleotides, and Variants and Fragments Thereof

In some embodiments, the present invention comprises isolated or recombinant, polynucleotides. A "recombinant" polynucleotide or polypeptide/protein, or biologically active portion thereof, as defined herein is no longer present in its original, native organism, such as when contained in a heterologous host cell or in a transgenic plant cell, seed or plant. In one embodiment, a recombinant polynucleotide is free of sequences (for example, protein encoding or regulatory sequences) that naturally flank the nucleic acid (i.e., sequences located at the 5' and 3' ends of the nucleic acid) in the genomic DNA of the organism from which the polynucleotide is derived. The term "recombinant" encompasses polynucleotides or polypeptides that have been manipulated with respect to the native polynucleotide or polypeptide, such that the polynucleotide or polypeptide differs (e.g., in chemical composition or structure) from what is occurring in nature. In another embodiment, a "recombinant" polynucleotide is free of internal sequences (i.e. introns) that naturally occur in the genomic DNA of the organism from which the polynucleotide is derived. A typical example of such polynucleotide is a so-called Complementary DNA (cDNA). For example, in various embodiments, the isolated HPPD inhibitor herbicide tolerance-encoding polynucleotide can contain less than about 5 kb, 4 kb, 3 kb, 2 kb, 1 kb, 0.5 kb, or 0.1 kb of nucleotide sequence that naturally flanks the polynucleotide in genomic DNA of the cell from which the polynucleotide is derived. Nucleic acid molecules of the invention include those that encode the HPPD of the invention. In some embodiments, the nucleic acid molecule of the invention is operably linked to a promoter capable of directing expression of the nucleic acid molecule in a host cell (e.g., a plant host cell or a bacterial host cell).

The present invention further contemplates variants and fragments of any nucleic acid sequence encoding the amino acid sequences set forth in any of SEQ ID NO:7-33. A "fragment" of a polynucleotide may encode a biologically active portion of a polypeptide, or it may be a fragment that can be used as a hybridization probe or PCR primer using methods disclosed elsewhere herein. Polynucleotides that are fragments of a polynucleotide comprise at least about 15, 20, 50, 75, 100, 200, 300, 350, 400, 450, 500, 550, 600, 650, 700, 750, 800, 850, 900, 950, 1000, 1050, 1100, 1150, contiguous nucleotides, or up to the number of nucleotides present in a full-length polynucleotide disclosed herein depending upon the intended use (e.g., an HPPD nucleic acid described herein). By "contiguous" nucleotides are intended nucleotide residues that are immediately adjacent to one another.

Fragments of the polynucleotides of the present invention generally will encode polypeptide fragments that retain the biological activity of the full-length HPPD inhibitor herbicide tolerance protein; i.e., herbicide-tolerance activity. By "retains herbicide tolerance activity" is intended that the fragment will have at least about 30%, at least about 50%, at least about 70%, at least about 80%, 85%, 90%, 95%, 100%, 110%, 125%, 150%, 175%, 200%, 250%, at least about 300% or greater of the herbicide tolerance activity of the full-length HPPD inhibitor herbicide tolerance protein disclosed herein as SEQ ID NO:7-33. Methods for measuring herbicide tolerance activity are well known in the art and exemplary methods are described herein. In a non-limiting example, a fragment of the invention will be tolerant to the same dose of an HPPD inhibitor herbicide, or tolerant to 1×, 2×, 3×, 4×, or higher dose of an HPPD inhibitor herbicide, or the fragments will be as or more tolerant based on pI50 or Ki between the fragment and SEQ ID NO:7-33.

A fragment of a polynucleotide that encodes a biologically active portion of a polypeptide of the invention will encode at least about 150, 175, 200, 250, 300, 350 contiguous amino acids, or up to the total number of amino acids present in a full-length polypeptide of the invention. In a non-limiting example, a fragment of a polynucleotide that encodes a biologically active portion of a HPPD protein having a proline at the amino acid position corresponding to amino acid position 335 of SEQ ID NO:1 and a phenylalanine or a tyrosine at the position corresponding to amino acid position 336 of SEQ ID NO:1 and, optionally, one or more amino acid substitutions at the positions corresponding to amino acid positions 188, 189, 200, 215, 226, 339, and 340 of SEQ ID NO:1, including the HPPD protein set forth in any of SEQ ID NO:7-33.

The invention also encompasses variant polynucleotides as described supra. "Variants" of the polynucleotide also include those sequences that encode the HPPD of the invention but that differ conservatively because of the degeneracy of the genetic code, as well as those that are sufficiently identical. Variants of the present invention will retain HPPD enzyme activity and HPPD herbicide inhibitor tolerance. The term "sufficiently identical" is intended a polypeptide or polynucleotide sequence that has at least about 53%, at least about 60% or 65% sequence identity, about 70% or 75% sequence identity, about 80% or 85% sequence identity, about 90%, 91%, 92%, 93%, 94%, 95%, 96%, 97%, 98% or 99% sequence identity compared to a reference sequence using one of the alignment programs using standard parameters. One of skill in the art will recognize that these values can be appropriately adjusted to determine corresponding identity of polypeptides encoded by two polynucleotides by taking into account codon degeneracy, amino acid similarity, reading frame positioning, and the like.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants that confer herbicide tolerance. These herbicide tolerance proteins are encompassed in the present invention and may be used in the methods of the present invention. Naturally occurring allelic variants can be identified with the use of well-known molecular biology techniques, such as polymerase chain reaction (PCR) and hybridization techniques as outlined below. Variant polynucleotides also include synthetically derived polynucleotides that have been generated, for example, by using site-directed or other mutagenesis strategies but which still encode the polypeptide having the desired biological activity.

The skilled artisan will further appreciate that changes can be introduced by further mutation of the polynucleotides of the invention thereby leading to further changes in the amino acid sequence of the encoded polypeptides, without altering the biological activity of the polypeptides. Thus, variant isolated polynucleotides can be created by introducing one or more additional nucleotide substitutions, additions, or deletions into the corresponding polynucleotide encoding the HPPD of the invention, such that 1-5, 1-10, or 1-15 amino acid substitutions, additions or deletions, or 1, 2, 3, 4, 5, 6, 7, 8, 9, 10, 11, 12, 13, 14, or 15 amino acid substitutions, additions or deletions, are introduced into the encoded polypeptide. Further mutations can be introduced by standard techniques, such as site-directed mutagenesis and PCR-mediated mutagenesis, or gene shuffling techniques. Such variant polynucleotides are also encompassed by the present invention.

Variant polynucleotides can be made by introducing mutations randomly along all or part of the coding sequence, such as by saturation mutagenesis or permutational mutagenesis, and the resultant mutants can be screened for the ability to confer herbicide tolerance activity to identify mutants that retain activity.

Additional methods for generating variants include subjecting a cell expressing a protein disclosed herein (or library thereof) to a specific condition that creates a stress to the activity of the protein. Specific conditions can include (but are not limited to) changes in temperature, changes in pH, and changes in the concentrations of substrates or inhibitors. The protein library can be subjected to these conditions during the time of protein expression (e.g., in *E. coli* or other host) or following creation of a protein extract, or following protein purification.

The functional or enzymatic activity of the protein library that has been subjected to a stress condition can then be compared to the reference protein to identify proteins with improved properties. This activity comparison can be carried out as part of a growth screen or alternatively as part of an enzymatic assay that quantifies the activity of the protein. The properties that can be identified as improved can include HPPD inhibitor herbicide tolerance, changes in kinetic constants (including Km, Ki, $k_{cat}$), protein stability, protein thermostability, or protein temperature and pH optimum.

D. Isolated Proteins and Variants and Fragments Thereof

Herbicide tolerance polypeptides are also encompassed within the present invention. A herbicide tolerance polypeptide includes preparations of polypeptides having less than about 30%, 20%, 10%, or 5% (by dry weight) of non-herbicide tolerance polypeptide (also referred to herein as a "contaminating protein"). In the present invention, "herbicide tolerance protein" is intended an HPPD polypeptide disclosed herein. Fragments, biologically active portions, and variants thereof are also provided, and may be used to practice the methods of the present invention.

"Fragments" or "biologically active portions" include polypeptide fragments comprising a portion of an amino acid sequence encoding an herbicide tolerance protein and that retains herbicide tolerance activity. A biologically active portion of an herbicide tolerance protein can be a polypeptide that is, for example, 10, 25, 50, 100 or more amino acids in length. Such biologically active portions can be prepared by recombinant techniques and evaluated for herbicide tolerance activity.

By "variants" is intended proteins or polypeptides having an amino acid sequence that is at least about 53%, 60%, 65%, about 70%, 75%, about 80%, 85%, 90%, 91%, 92%, 93%, 94%, 95%, 96%, 97%, 98% or 99% identical to any of SEQ ID NO:7-33, wherein said variant has HPPD enzyme activity and HPPD inhibitor herbicide tolerance One of skill in the art will recognize that these values can be appropriately adjusted to determine corresponding identity of polypeptides encoded by two polynucleotides by taking into account codon degeneracy, amino acid similarity, reading frame positioning, and the like.

For example, conservative amino acid substitutions may be made at one or more nonessential amino acid residues. A "nonessential" amino acid residue is a residue that can be altered from the reference sequence of a polypeptide without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in non-conserved regions that retain function. In general, such substitutions would not be made for conserved amino acid residues, or for amino acid residues residing within a conserved motif, where such residues are essential for polypeptide activity. However, one of skill in the art would understand that functional variants may have minor conserved or non-conserved alterations in the conserved residues.

Antibodies to the HPPD of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Thus, one aspect of the invention concerns antibodies, single-chain antigen binding molecules, or other proteins that specifically bind to one or more of the protein or peptide molecules of the invention and their homologs, fusions or fragments. In a particularly preferred embodiment, the antibody specifically binds to a protein having the amino acid sequence set forth in SEQ ID NO:7-33 or a fragment thereof. In another embodiment, the antibody specifically binds to a fusion protein comprising an amino acid sequence selected from the amino acid sequence set forth in SEQ ID NO:7-33, or a fragment thereof. In some embodiments, the antibody specifically binds to the region of the protein corresponding to amino acid positions 188 and 189 of SEQ ID NO:1, or the region of the protein corresponding to amino acid position 200 of SEQ ID NO:1, or the region of the protein corresponding to amino acid position 215 of SEQ ID NO:1, or the region of the protein corresponding to amino acid positions 335-340 of SEQ ID NO:1.

Antibodies of the invention may be used to quantitatively or qualitatively detect the protein or peptide molecules of the invention, or to detect post translational modifications of the proteins. As used herein, an antibody or peptide is said to "specifically bind" to a protein or peptide molecule of the invention if such binding is not competitively inhibited by the presence of non-related molecules.

E. Gene Stacking

In the commercial production of crops, it is desirable to eliminate under reliable pesticidal management unwanted plants (i.e.,"weeds") from a field of crop plants. An ideal treatment would be one which could be applied to an entire field but which would eliminate only the unwanted plants while leaving the crop plants unaffected. One such treatment system would involve the use of crop plants which are tolerant to an herbicide so that when the herbicide is sprayed on a field of herbicide-tolerant crop plants, the crop plants would continue to thrive while non-herbicide-tolerant weeds are killed or severely damaged. Ideally, such treatment systems would take advantage of varying herbicide properties so that weed control could provide the best possible combination of flexibility and economy. For example, individual herbicides have different longevities in the field, and some herbicides persist and are effective for a relatively long time after they are applied to a field while other herbicides are quickly broken down into other and/or non-active compounds. An ideal treatment system would allow the use of different herbicides so that growers could tailor the choice of herbicides for a particular situation.

While a number of herbicide-tolerant crop plants are presently commercially available, an issue that has arisen for many commercial herbicides and herbicide/crop combinations is that individual herbicides typically have incomplete spectrum of activity against common weed species. For most individual herbicides which have been in use for some time, populations of herbicide resistant weed species and biotypes have become more prevalent (see, e.g., Tranel and Wright (2002) *Weed Science* 50: 700-712; Owen and Zelaya (2005) *Pest Manag. Sci.* 61: 301-311). Transgenic plants which are tolerant to more than one herbicide have been described (see, e.g., WO2005/012515). However, improvements in every aspect of crop production, weed control options, extension of residual weed control, and improvement in crop yield are continuously in demand.

The HPPD protein or nucleotide sequence of the invention is advantageously combined in plants with other genes which encode proteins or RNAs that confer useful agronomic properties to such plants. Among the genes which encode proteins or RNAs that confer useful agronomic properties on the transformed plants, mention can be made of the DNA sequences encoding proteins which confer tolerance to one or more herbicides that, according to their chemical structure, differ from HPPD inhibitor herbicides, and others which confer tolerance to certain insects, those which confer tolerance to certain diseases, DNAs that encodes RNAs that provide nematode or insect control, and the like.

Such genes are in particular described in published PCT Patent Applications WO91/02071 and WO95/06128 and in U.S. Pat. No. 7,923,602 and US Patent Application Publication No. 20100166723, each of which is herein incorporated by reference in its entirety.

Among the DNA sequences encoding proteins which confer tolerance to certain herbicides on the transformed plant cells and plants, mention can be made of a bar or PAT gene or the *Streptomyces coelicolor* gene described in WO2009/152359 which confers tolerance to glufosinate herbicides, a gene encoding a suitable EPSPS which confers tolerance to herbicides having EPSPS as a target, such as glyphosate and its salts (U.S. Pat. Nos. 4,535,060, 4,769, 061, 5,094,945, 4,940,835, 5,188,642, 4,971,908, 5,145,783, 5,310,667, 5,312,910, 5,627,061, 5,633,435), a gene encoding glyphosate-n-acetyltransferase (for example, U.S. Pat. Nos. 8,222,489, 8,088,972, 8,044,261, 8,021,857, 8,008, 547, 7,999,152, 7,998,703, 7,863,503, 7,714,188, 7,709,702, 7,666,644, 7,666,643, 7,531,339, 7,527,955, and 7,405, 074), or a gene encoding glyphosate oxydoreductase (for example, U.S. Pat. No. 5,463,175).

Among the DNA sequences encoding a suitable EPSPS which confer tolerance to the herbicides which have EPSPS as a target, mention will more particularly be made of the gene which encodes a plant EPSPS, in particular maize EPSPS, particularly a maize EPSPS which comprises two mutations, particularly a mutation at amino acid position 102 and a mutation at amino acid position 106 (WO2004/074443), and which is described in patent Application U.S. Pat. No. 6,566,587, hereinafter named double mutant maize EPSPS or 2mEPSPS, or the gene which encodes an EPSPS isolated from *Agrobacterium* and which is described by sequence ID No. 2 and sequence ID No. 3 of U.S. Pat. No. 5,633,435, also named CP4.

Among the DNA sequences encoding a suitable EPSPS which confer tolerance to the herbicides which have EPSPS as a target, mention will more particularly be made of the gene which encodes an EPSPS GRG23 from *Arthrobacter globiformis*, but also the mutants GRG23 ACE1, GRG23 ACE2, or GRG23 ACE3, particularly the mutants or variants of GRG23 as described in WO2008/100353, such as GRG23 (ace3)R173K of SEQ ID No. 29 in WO2008/100353.

In the case of the DNA sequences encoding EPSPS, and more particularly encoding the above genes, the sequence encoding these enzymes is advantageously preceded by a sequence encoding a transit peptide, in particular the "optimized transit peptide" described in U.S. Pat. No. 5,510,471 or 5,633,448.

Exemplary herbicide tolerance traits that can be combined with the nucleic acid sequence of the invention further include at least one ALS (acetolactate synthase) inhibitor (WO2007/024782); a mutated *Arabidopsis* ALS/AHAS gene (U.S. Pat. No. 6,855,533); genes encoding 2,4-D-monooxygenases conferring tolerance to 2,4-D (2,4-dichlorophenoxyacetic acid) by metabolization (U.S. Pat. No. 6,153,401); and, genes encoding Dicamba monooxygenases conferring tolerance to dicamba (3,6-dichloro-2-methoxybenzoic acid) by metabolization (US 2008/0119361 and US 2008/0120739).

In various embodiments, the HPPD of the invention is stacked with one or more herbicide tolerant genes, including one or more additional HPPD inhibitor herbicide tolerant genes, and/or one or more genes tolerant to glyphosate and/or glufosinate. In one embodiment, the HPPD of the invention is combined with 2mEPSPS and bar.

Among the DNA sequences encoding proteins concerning properties of tolerance to insects, mention will more particularly be made of the Bt proteins widely described in the literature and well known to those skilled in the art. Mention will also be made of proteins extracted from bacteria such as *Photorhabdus* (WO97/17432 & WO98/08932).

Among such DNA sequences encoding proteins of interest which confer novel properties of tolerance to insects, mention will more particularly be made of the Bt Cry or VIP proteins widely described in the literature and well known to those skilled in the art. These include the Cry1F protein or hybrids derived from a Cry1F protein (e.g., the hybrid Cry1 A-Cry1F proteins described in U.S. Pat. Nos. 6,326,169; 6,281,016; 6,218,188, or toxic fragments thereof), the Cry1A-type proteins or toxic fragments thereof, preferably the Cry1Ac protein or hybrids derived from the Cry1Ac protein (e.g., the hybrid Cry1Ab-Cry1Ac protein described in U.S. Pat. No. 5,880,275) or the Cry1Ab or Bt2 protein or insecticidal fragments thereof as described in EP451878, the Cry2Ae, Cry2Af or Cry2Ag proteins as described in WO2002/057664 or toxic fragments thereof, the Cry1A.105 protein described in WO 2007/140256 (SEQ ID No. 7) or a toxic fragment thereof, the VIP3Aa19 protein of NCBI accession ABG20428, the VIP3Aa20 protein of NCBI accession ABG20429 (SEQ ID No. 2 in WO 2007/142840), the VIP3A proteins produced in the COT202 or COT203 cotton events (WO2005/054479 and WO2005/054480, respectively), the Cry proteins as described in WO2001/47952, the VIP3Aa protein or a toxic fragment thereof as described in Estruch et al. (1996), Proc Natl Acad Sci USA. 28; 93(11):5389-94 and U.S. Pat. No. 6,291,156, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932 (e.g., Waterfield et al., 2001, Appl Environ Microbiol. 67(11):5017-24; Ffrench-Constant and Bowen, 2000, Cell Mol Life Sci.; 57(5):828-33). Also any variants or mutants of any one of these proteins differing in some (1-10, preferably 1-5) amino acids from any of the above sequences, particularly the sequence of their toxic fragment, or which are fused to a transit peptide, such as a plastid transit peptide, or another protein or peptide, is included herein.

In various embodiments, the HPPD sequence of the invention can be combined in plants with one or more genes conferring a desirable trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like.

Particularly useful transgenic events which may be combined with the genes of the current invention in plants of the same species (e.g., by crossing or by re-transforming a plant containing another transgenic event with a chimeric gene of the invention), include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US-A 2005-216969); Event 3006-210-23 (cotton, insect control—herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control—herbicide tolerance, deposited as ATCC PTA-11508, described in WO 11/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480););

Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-1 (brinjal, insect control, not deposited, described in WO 07/091277); Event FI117 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait—herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control—herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHT0H2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control—herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control—herbicide tolerance, not deposited, described in US-A 2005-039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession N°

PTA-11041) optionally stacked with event EE-GM1/LL27 or event EE-GM2/LL55 (WO2011/063413A2), event DAS-68416-4 (soybean, herbicide tolerance, ATCC Accession N° PTA-10442, WO2011/066360A1), event DAS-68416-4 (soybean, herbicide tolerance, ATCC Accession N° PTA-10442, WO2011/066384A1), event DP-040416-8 (corn, insect control, ATCC Accession N° PTA-11508, WO2011/075593A1), event DP-043A47-3 (corn, insect control, ATCC Accession N° PTA-11509, WO2011/075595A1), event DP-004114-3 (corn, insect control, ATCC Accession N° PTA-11506, WO2011/084621A1), event DP-032316-8 (corn, insect control, ATCC Accession N° PTA-11507, WO2011/084632A1), event MON-88302-9 (oilseed rape, herbicide tolerance, ATCC Accession N° PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession N°. PTA-10296, WO2012/051199A2), event DAS-44406-6 (soybean, stacked herbicide tolerance, ATCC Accession N°. PTA-11336, WO2012/075426A1), event DAS-14536-7 (soybean, stacked herbicide tolerance, ATCC Accession N°. PTA-11335, WO2012/075429A1), event SYN-000H2-5 (soybean, herbicide tolerance, ATCC Accession N°. PTA-11226, WO2012/082548A2), event DP-061061-7 (oilseed rape, herbicide tolerance, no deposit N° available, WO2012071039A1), event DP-073496-4 (oilseed rape, herbicide tolerance, no deposit N° available, US2012131692), event 8264.44.06.1 (soybean, stacked herbicide tolerance, Accession N° PTA-11336, WO2012075426A2), event 8291.45.36.2 (soybean, stacked herbicide tolerance, Accession N°. PTA-11335, WO2012075429A2), event SYHT0H2 (soybean, ATCC Accession N°. PTA-11226, WO2012/082548A2), event MON88701 (cotton, ATCC Accession N° PTA-11754, WO2012/134808A1), event KK179-2 (alfalfa, ATCC Accession N° PTA-11833, WO2013/003558A1), event pDAB8264.42.32.1 (soybean, stacked herbicide tolerance, ATCC Accession N° PTA-11993, WO2013/010094A1), event MZDT09Y (corn, ATCC Accession N° PTA-13025, WO2013/012775A1).

F. Polynucleotide Constructs

The polynucleotides encoding the HPPD polypeptides of the present invention may be modified to obtain or enhance expression in plant cells. The polynucleotides encoding the polypeptides identified herein may be provided in expression cassettes for expression in the plant of interest. A "plant expression cassette" includes a DNA construct, including a recombinant DNA construct, that is capable of resulting in the expression of a polynucleotide in a plant cell. The cassette can include in the 5'-3' direction of transcription, a transcriptional initiation region (i.e., promoter, particularly a heterologous promoter) operably-linked to one or more polynucleotides of interest, and/or a translation and transcriptional termination region (i.e., termination region) functional in plants. The cassette may additionally contain at least one additional polynucleotide to be introduced into the organism, such as a selectable marker gene. Alternatively, the additional polynucleotide(s) can be provided on multiple expression cassettes. Such an expression cassette is provided with a plurality of restriction sites for insertion of the polynucleotide(s) to be under the transcriptional regulation of the regulatory regions.

In a further embodiment, the present invention relates to a chimeric gene comprising a coding sequence comprising heterologous the nucleic acid of the invention operably linked to a plant-expressible promoter and optionally a transcription termination and polyadenylation region. "Heterologous" generally refers to the polynucleotide or polypeptide that is not endogenous to the cell or is not endogenous to the location in the native genome in which it is present, and has been added to the cell by infection, transfection, microinjection, electroporation, microprojection, or the like. By "operably linked" is intended a functional linkage between two polynucleotides. For example, when a promoter is operably linked to a DNA sequence, the promoter sequence initiates and mediates transcription of the DNA sequence. It is recognized that operably linked polynucleotides may or may not be contiguous and, where used to reference the joining of two polypeptide coding regions, the polypeptides are expressed in the same reading frame.

The promoter may be any polynucleotide sequence which shows transcriptional activity in the chosen plant cells, plant parts, or plants. The promoter may be native or analogous, or foreign or heterologous, to the plant host and/or to the DNA sequence of the invention. Where the promoter is "native" or "analogous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds (1987) *Nucleic Acids Res.* 15:2343-2361. Also, the location of the promoter relative to the transcription start may be optimized. See, e.g., Roberts et al. (1979) *Proc. Natl. Acad. Sci. USA,* 76:760-764. Many suitable promoters for use in plants are well known in the art.

For instance, suitable constitutive promoters for use in plants include: the promoters from plant viruses, such as the peanut chlorotic streak caulimovirus (PClSV) promoter (U.S. Pat. No. 5,850,019); the 35S promoter from cauliflower mosaic virus (CaMV) (Odell et al. (1985) *Nature* 313:810-812); promoters of *Chlorella* virus methyltransferase genes (U.S. Pat. No. 5,563,328) and the full-length transcript promoter from figwort mosaic virus (FMV) (U.S. Pat. No. 5,378,619); the promoters from such genes as rice actin (McElroy et al. (1990) *Plant Cell* 2:163-171 and U.S. Pat. No. 5,641,876); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730 and U.S. Pat. No. 5,510,474); maize H3 histone (Lepetit et al. (1992) *Mol. Gen. Genet.* 231:276-285 and Atanassova et al. (1992) *Plant* 2(3):291-300); *Brassica napus* ALS3 (PCT application WO97/41228); a plant ribulose-biscarboxylase/oxygenase (RuBisCO) small subunit gene; the circovirus (AU 689 311) or the Cassava vein mosaic virus (CsVMV, U.S. Pat. No. 7,053,205); and promoters of various *Agrobacterium* genes (see U.S. Pat. Nos. 4,771,002; 5,102,796; 5,182,200; and 5,428,147).

Suitable inducible promoters for use in plants include: the promoter from the ACE1 system which responds to copper (Mett et al. (1993) PNAS 90:4567-4571); the promoter of the maize In2 gene which responds to benzenesulfonamide herbicide safeners (Hershey et al. (1991) *Mol. Gen. Genetics* 227:229-237 and Gatz et al. (1994) *Mol. Gen. Genetics* 243:32-38); and the promoter of the Tet repressor from Tn10 (Gatz et al. (1991) *Mol. Gen. Genet.* 227:229-237). Another inducible promoter for use in plants is one that responds to an inducing agent to which plants do not normally respond.

An exemplary inducible promoter of this type is the inducible promoter from a steroid hormone gene, the transcriptional activity of which is induced by a glucocorticosteroid hormone (Schena et al. (1991) *Proc. Natl. Acad. Sci. USA* 88:10421) or the recent application of a chimeric transcription activator, XVE, for use in an estrogen receptor-based inducible plant expression system activated by estradiol (Zuo et al. (2000) *Plant J.,* 24:265-273). Other inducible promoters for use in plants are described in EP 332104, PCT WO 93/21334 and PCT WO 97/06269 which are herein incorporated by reference in their entirety. Promoters composed of portions of other promoters and partially or totally synthetic promoters can also be used. See, e.g., Ni et al. (1995) *Plant J.* 7:661-676 and PCT WO 95/14098 describing such promoters for use in plants.

In one embodiment of this invention, a promoter sequence specific for particular regions or tissues of plants can be used to express the HPPD proteins of the invention, such as promoters specific for seeds (Datla, R. et al., 1997, Biotechnology Ann. Rev. 3, 269-296), especially the napin promoter (EP 255 378 A1), the phaseolin promoter, the glutenin promoter, the helianthinin promoter (WO92/17580), the albumin promoter (WO98/45460), the oleosin promoter (WO98/45461), the SAT1 promoter or the SAT3 promoter (PCT/US98/06978).

Use may also be made of an inducible promoter advantageously chosen from the phenylalanine ammonia lyase (PAL), HMG-CoA reductase (HMG), chitinase, glucanase, proteinase inhibitor (PI), PR1 family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO98/45445). Multiple promoters can be used in the constructs of the invention, including in succession.

The promoter may include, or be modified to include, one or more enhancer elements. In some embodiments, the promoter may include a plurality of enhancer elements. Promoters containing enhancer elements provide for higher levels of transcription as compared to promoters that do not include them. Suitable enhancer elements for use in plants include the PClSV enhancer element (U.S. Pat. No. 5,850,019), the CaMV 35S enhancer element (U.S. Pat. Nos. 5,106,739 and 5,164,316) and the FMV enhancer element (Maiti et al. (1997) *Transgenic Res.* 6:143-156); the translation activator of the tobacco mosaic virus (TMV) described in Application WO87/07644, or of the tobacco etch virus (TEV) described by Carrington & Freed 1990, J. Virol. 64: 1590-1597, for example, or introns such as the adh1 intron of maize or intron 1 of rice actin. See also PCT WO96/23898, WO2012/021794, WO2012/021797, WO2011/084370, and WO2011/028914.

Often, such constructs can contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the construct can be engineered to contain a signal peptide to facilitate transfer of the peptide to the endoplasmic reticulum. By "signal sequence" is intended a sequence that is known or suspected to result in co-translational or post-translational peptide transport across the cell membrane. In eukaryotes, this typically involves secretion into the Golgi apparatus, with some resulting glycosylation. By "leader sequence" is intended any sequence that, when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a polynucleotide located upstream of a coding sequence.

Other upstream or downstream untranslated elements include enhancers. Enhancers are polynucleotides that act to increase the expression of a promoter region. Enhancers are well known in the art and include, but are not limited to, the SV40 enhancer region and the 35S enhancer element.

The termination region may be native with the transcriptional initiation region, may be native with the sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; Joshi et al. (1987) *Nucleic Acid Res.* 15:9627-9639; and European Patent Application EP 0 633 317 A1.

In one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gown (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the polynucleotides of interest are targeted to the chloroplast for expression. In this manner, where the polynucleotide of interest is not directly inserted into the chloroplast, the expression cassette will additionally contain a polynucleotide encoding a transit peptide to direct the nucleotide of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The polynucleotides of interest to be targeted to the chloroplast may be optimized for expression in the chloroplast to account for differences in codon usage between the plant nucleus and this organelle. In this manner, the polynucleotides of interest may be synthesized using chloroplast-preferred codons. See, for example, U.S. Pat. No. 5,380,831, herein incorporated by reference.

This plant expression cassette can be inserted into a plant transformation vector. By "transformation vector" is intended a DNA molecule that allows for the transformation of a cell. Such a molecule may consist of one or more expression cassettes, and may be organized into more than one vector DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a polynucleotide construct designed for transfer between different host cells. "Expression vector" refers to a vector that has the ability to incorporate, integrate and express heterologous DNA sequences or fragments in a foreign cell.

The plant transformation vector comprises one or more DNA vectors for achieving plant transformation. For example, it is a common practice in the art to utilize plant transformation vectors that comprise more than one contiguous DNA segment. These vectors are often referred to in the art as binary vectors. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "polynucleotide of interest" (a polynucleotide engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker sequence and the sequence of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science,* 5:446-451). Several types of *Agrobacterium* strains (e.g., LBA4404, GV3101, EHA101, EHA105, etc.) can be used for plant transformation. The second plasmid vector is not necessary for introduction of polynucleotides into plants by other methods such as microprojection, microinjection, electroporation, polyethylene glycol, etc.

G. Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods. See, for example, the methods for transforming plant cells and regenerating plants described in: U.S. Pat. Nos. 4,459,355, 4,536,475, 5,464,763, 5,177,010, 5,187,073, EP 267,159 A1, EP 604 662 A1, EP 672 752 A1, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174 A1, EP 486 233 A1, EP 486 234 A1, EP 539 563 A1, EP 674 725 A1, WO91/02071, WO95/06128, and WO2011/095460, each of which is herein incorporated by reference, particularly with respect to the transformation methods described therein.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grow into mature plants and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997)*Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The plant cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome. In various embodiments, the seed can be coated with at least one fungicide and/or at least one insecticide, at least one herbicide, and/or at least one safener, or any combination thereof.

H Evaluation of Plant Transformation

Following introduction of heterologous foreign DNA into plant cells, the transformation or integration of the heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual* (Cold Spring Harbor Laboratory Press, Cold Spring Harbor, N.Y.)). PCR is carried out using oligonucleotide primers specific to the gene of interest or *Agrobacterium* vector background, etc.

Plant transformation may be confirmed by Southern blot analysis of genomic DNA (Sambrook and Russell (2001) supra). In general, total DNA is extracted from the transformant, digested with appropriate restriction enzymes, fractionated in an agarose gel and transferred to a nitrocellulose or nylon membrane. The membrane or "blot" can then be probed with, for example, radiolabeled $^{32}$P target DNA fragment to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, and blotted onto a nylon filter according to standard procedures that are routinely used in the art (Sambrook and Russell (2001) supra). Expression of RNA encoded by nucleotide sequences of the invention is then tested by hybridizing the filter to a radioactive probe derived from a GDC by methods known in the art (Sambrook and Russell (2001) supra). RNA can also be detected and/or quantified using reverse transcriptase PCR as known in the art (e.g., Green and Sambrook (2012) *Molecular Cloning: A Laboratory Manual*, 4$^{th}$ Edition, Cold Spring Harbor Laboratory Press, Woodbury, N.Y.).

Western blot, ELISA, lateral flow testing, and biochemical assays and the like may be carried out on the transgenic plants to determine the presence of protein encoded by the herbicide tolerance gene by standard procedures (Sambrook and Russell (2001) supra) using antibodies that bind to one or more epitopes present on the herbicide tolerance protein.

In one aspect of the invention, the HPPD genes described herein are useful as markers to assess transformation of bacterial or plant cells.

I. Use as a Marker for Transformation

The invention also relates to the use, in a method for transforming plants, of a nucleic acid which encodes an HPPD according to the invention as a marker gene or as a coding sequence which makes it possible to confer to the plant tolerance to herbicides which are HPPD inhibitors, and the use of one or more HPPD inhibitor(s) on plants comprising a nucleic acid sequence encoding a HPPD according to the invention. See, for example, U.S. Pat. No. 6,791,014, which is herein incorporated by reference in its entirety.

In this embodiment, an HPPD inhibitor can be introduced into the culture medium of the competent plant cells so as to bleach said cells before the transformation step. The bleached competent cells are then transformed with the gene for tolerance to HPPD inhibitors, as a selection marker, and the transformed cells which have integrated said selection marker into their genome become green, enabling them to be selected. Such a process makes it possible to decrease the time required for selecting the transformed cells.

Thus, one embodiment of the present invention consists of a method for transforming plant cells by introducing a heterologous gene into said plant cells with a gene for tolerance to HPPD inhibitors as selection markers, wherein the method comprises preparing and culturing competent plant cells capable of receiving the heterologous gene in a suitable medium and introducing a suitable amount of HPPD inhibitor into the suitable culture medium of the competent plant cells. The competent cells are then transformed with the heterologous gene and the selection marker, and the transformed cells comprising the heterologous gene are grown in a suitable medium and transformants selected therefrom. The transformed cells can then be regenerated into a fertile transformed plant.

J. Plants and Plant Parts

By "plant" is intended whole plants, plant organs (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, pollen). The present invention may be used for introduction of polynucleotides into any plant species, including, but not limited to, monocots and dicots. Examples of plants of interest include, but are not limited to, corn (maize), sorghum, wheat, sunflower, tomato, crucifers, peppers, potato, cotton, rice, soybean, sugar beet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, hydrangea, hibiscus, roses, tulips, daffodils, petunias, carnation, poinsettia, and chrysanthemum. Crop plants are also of interest, including, for example, maize, sorghum, wheat, sunflower, tomato, crucifers, peppers, potato, cotton, rice, soybean, sugar beet, sugarcane, tobacco, barley, oilseed rape, etc.

This invention is suitable for any member of the monocot plant family including, but not limited to, maize, rice, barley, oats, wheat, sorghum, rye, sugarcane, pineapple, yams, onion, banana, coconut, and dates.

K. Methods for Increasing Plant Yield

Methods for increasing plant yield are provided. The methods comprise providing a plant comprising, or introducing into a plant or plant cell, a polynucleotide comprising a nucleotide sequence encoding an HPPD of the invention, growing the plant or a seed thereof in a field, and producing a harvest from said plants or seeds. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant comprising an HPPD sequence of the invention is treated with an effective concentration of an HPPD inhibitor herbicide, such as one or more HPPD inhibitor herbicide(s) selected from the group consisting of HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, where the herbicide application results in enhanced plant yield.

Methods for conferring herbicide tolerance in a plant or plant part are also provided. In such methods, a nucleotide sequence encoding an HPPD of the invention is introduced into the plant, wherein expression of the polynucleotide results in HPPD inhibitor herbicide tolerance. Plants produced via this method can be treated with an effective concentration of an herbicide (such as one or more HPPD inhibitor herbicide(s) selected from the group consisting of HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone) and display an increased tolerance to the herbicide. An "effective concentration" of an herbicide in this application is an amount sufficient to slow or stop the growth of plants or plant parts that are not naturally tolerant or rendered tolerant to the herbicide.

L. Methods of Controlling Weeds in a Field

The present invention therefore also relates to a method of controlling undesired plants or for regulating the growth of plants in crops of plants comprising a nucleotide sequence encoding an HPPD according to the invention, where one or more HPPD inhibitor herbicides, for example, one or more HPPD inhibitor herbicides selected from the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, an effective concentration of one or more HPPD inhibitor herbicide(s), for example, one or more HPPD inhibitor herbicides selected from the group consisting of HPPD inhibitor herbicides of the class of N (1,2,5-oxadiazol-3-yl)benzamides; N-(tetrazol-4-yl)- or N-(triazol-3-yl)arylcarboxamides, preferably such as 2-chloro-3-ethoxy-4-(methylsulfonyl)-N-(1-methyl-1H-tetrazol-5-yl)benzamide and 2-Chloro-3-(methoxymethyl)-4-(methylsulfonyl)-N-(1-methyl-1H-tetrazol-5-yl)benzamide; N-(1,3,4-oxadiazol-2-yl) benzamides, preferably such as 2-methyl-N-(5-methyl-1,3,4-oxadiazol-2-yl)-3-(methylsulfonyl)-4-(trifluoromethyl) benzamide (Cmpd. 1); N-(tetrazol-5-yl)- or N-(triazol-3-yl) arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), and 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, the class of isoxazoles preferably such as isoxaflutole, or of the class of pyrazolinates, preferably such as pyrasulfotole and topramezone, particularly selected from tembotrione, sulcotrione, topramezone, bicyclopyrone, tefuryltrione, isoxaflutole, and mesotrione, can be applied for example pre-planting (if appropriate also by incorporation into the soil), pre-emergence or post-emergence, and may be combined with the application of other herbicides to which the crop is naturally tolerant, or to which it is resistant via expression of one or more other herbicide resistance transgenes. See, e.g., U.S. App. Pub. No. 2004/0058427 and PCT App. Pub. No. WO98/20144. By "effective concentration" is intended the concentration which controls the growth or spread of weeds or other untransformed plants without significantly affecting the HPPD inhibitor-tolerant plant or plant seed. Those of skill in the art understand that application of herbicides can take many different forms and can take place at many different times prior to and/or throughout the seed planting and growth process. "Pre-emergent" application refers to an herbicide which is applied to an area of interest (e.g., a field or area of cultivation) before a plant emerges visibly from the soil. "Post-emergent" application refers to an herbicide which is applied to an area after a plant emerges visibly from the soil. In some instances, the terms "pre-emergent" and "post-emergent" are used with reference to a weed in an area of interest, and in some instances these terms are used with reference to a crop plant in an area of interest. When used with reference to a weed, these terms may apply to a particular type of weed or species of weed that is present or believed to be present in the area of interest. "Pre-plant incorporation" of an herbicide involves the incorporation of compounds into the soil prior to planting.

Thus, the present invention comprises a method of controlling weeds in a field comprising planting in a field a plant or a seed thereof comprising an HPPD of the invention and applying to said plant or area surrounding said plant an effective concentration of one or more HPPD inhibitor herbicides.

In one embodiment of this invention, a field to be planted with plants (such as soybean, cotton, corn, or wheat plants, e.g.) containing an HPPD nucleotide sequence of the invention, can be treated with an HPPD inhibitor herbicide, such as isoxaflutole (IFT), before the plants are planted or the seeds are sown, which cleans the field of weeds that are killed by the HPPD inhibitor, allowing for no-till practices, followed by planting or sowing of the plants in that same pre-treated field later on (burndown application using an HPPD inhibitor herbicide). The residual activity of IFT will also protect the emerging and growing plants from competition by weeds in the early growth stages. Once the plants have a certain size, and weeds tend to re-appear, glufosinate or glyphosate, or an HPPD inhibitor or a mixture of an HPPD inhibitor with another herbicide such as glyphosate, can be applied as post-emergent herbicide over the top of the plants, when such plants are tolerant to said herbicides.

In another embodiment of this invention, a field in which seeds containing an HPPD nucleotide sequence of the invention were sown, can be treated with an HPPD inhibitor herbicide, such as IFT, before the plants emerge but after the seeds are sown (the field can be made weed-free before sowing using other means, typically conventional tillage practices such as ploughing, chissel ploughing, or seed bed preparation), where residual activity will keep the field free of weeds killed by the herbicide so that the emerging and growing plants have no competition by weeds (pre-emergence application of an HPPD inhibitor herbicide). Once the plants have a certain size, and weeds tend to re-appear, glufosinate or glyphosate, or an HPPD inhibitor or a mixture of an HPPD inhibitor with another herbicide such as glyphosate, can be applied as post-emergent herbicide over the top of the plants, when such plants are tolerant to said herbicides.

In another embodiment of this invention, plants containing an HPPD nucleotide sequence of the invention, can be treated with an HPPD inhibitor herbicide, over the top of the plants that have emerged from the seeds that were sown, which cleans the field of weeds killed by the HPPD inhibitor, which application can be together with (e.g., in a spray tank mix), followed by or preceded by a treatment with glyphosate or glufosinate as post-emergent herbicide over the top of the plants (post-emergence application of an HPPD inhibitor herbicide (with or without glyphosate)), when such plants are tolerant to such herbicides.

Examples of individual representatives of the monocotyledonous and dicotyledonous weeds which can be controlled with an HPPD inhibitor herbicide include:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

HPPD inhibitor herbicides useful in the present invention, including but not limited to HPPD inhibitor herbicides of the class of N (1,2,5-oxadiazol-3-yl)benzamides; N-(tetrazol-4-yl)- or N-(triazol-3-yl)arylcarboxamides, such as 2-chloro-3-ethoxy-4-(methylsulfonyl)-N-(1-methyl-1H-tetrazol-5-yl) benzamide and 2-Chloro-3-(methoxymethyl)-4-(methylsulfonyl)-N-(1-methyl-1H-tetrazol-5-yl)benzamide; N-(1,3,4-oxadiazol-2-yl)benzamides, preferably such as 2-methyl-N-(5-methyl-1,3,4-oxadiazol-2-yl)-3-(methylsulfonyl)-4-(trifluoromethyl)benzamide (Cmpd. 1); N-(tetrazol-5-yl)- or N-(triazol-3-yl)arylcarboxamides, preferably such as 2-chloro-3-ethoxy-4-(methylsulfonyl)-N-(1-methyl-1H-tetrazol-5-yl)benzamide (Cmpd.2), 4-(difluoromethyl)-2-methoxy-3-(methylsulfonyl)-N-(1-methyl-1H-tetrazol-5-yl)benzamide (Cmpd. 3), 2-chloro-3-(methylsulfanyl)-N-(1-methyl-1H-tetrazol-5-yl)-4-(trifluoromethyl)benzamide (Cmpd. 4), 2-(methoxymethyl)-3-(methylsulfinyl)-N-(1-methyl-1H-tetrazol-5-yl)-4-(trifluoromethyl)benzamide (Cmpd. 5); pyridazinone derivatives (WO2013/050421 and WO2013/083774); substituted 1,2,5-oxadiazoles (WO2013/072300 and WO2013/072402); and oxoprazin derivatives (WO2013/054495); triketones, preferably such as tembotrione, sulcotrione and mesotrione; the class of isoxazoles preferably such as isoxaflutole; or of the class of pyrazolinates, preferably such as pyrasulfotole and topramezone, can be formulated in various ways, depending on the prevailing biological and/or physico-chemical parameters. Examples of possible formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for application by broadcasting and on the soil, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical technology], volume 7, C. Hanser Verlag Munich, 4th Ed. 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents, Chem. Publ. Co. Inc., N.Y. 1964; Schönfeldt, Grenzflächenaktive Äthylenoxidaddukte" [Interface-active ethylene oxide adducts], Wiss. Verlagsgesell., Stuttgart 1976; Winnacker-Küchler, "Chemische Technologie" [Chemical technology], volume 7, C. Hanser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a ready mix or a tank mix.

M. Methods of Introducing Gene of the Invention into Another Plant

Also provided herein are methods of introducing the HPPD nucleotide sequence of the invention into another plant. The HPPD nucleotide sequence of the invention, or a fragment thereof, can be introduced into second plant by recurrent selection, backcrossing, pedigree breeding, line selection, mass selection, mutation breeding and/or genetic marker enhanced selection.

Thus, in one embodiment, the methods of the invention comprise crossing a first plant comprising an HPPD nucleotide sequence of the invention with a second plant to produce F1 progeny plants and selecting F1 progeny plants that are tolerant to an HPPD inhibitor herbicide or that comprise the HPPD nucleotide sequence of the invention. The methods may further comprise crossing the selected progeny plants with the first plant comprising the HPPD nucleotide sequence of the invention to produce backcross progeny plants and selecting backcross progeny plants that are tolerant to an HPPD inhibitor herbicide or that comprise the HPPD nucleotide sequence of the invention. Methods for evaluating HPPD inhibitor herbicide tolerance are provided elsewhere herein. The methods may further comprise repeating these steps one or more times in succession to produce selected second or higher backcross progeny plants that are tolerant to an HPPD inhibitor herbicide or that comprise the HPPD nucleotide sequence of the invention.

Any breeding method involving selection of plants for the desired phenotype can be used in the method of the present invention. In some embodiments, The F1 plants may be self-pollinated to produce a segregating F2 generation. Individual plants may then be selected which represent the desired phenotype (e.g., HPPD inhibitor herbicide tolerance) in each generation (F3, F4, F5, etc.) until the traits are homozygous or fixed within a breeding population.

The second plant can be a plant having a desired trait, such as herbicide tolerance, insect tolerance, drought tolerance, nematode control, water use efficiency, nitrogen use efficiency, improved nutritional value, disease resistance, improved photosynthesis, improved fiber quality, stress tolerance, improved reproduction, and the like. The second plant may be an elite event as described elsewhere herein In various embodiments, plant parts (whole plants, plant organs (e.g., leaves, stems, roots, etc.), seeds, plant cells, propagules, embryos, and the like) can be harvested from the resulting cross and either propagated or collected for downstream use (such as food, feed, biofuel, oil, flour, meal, etc).

N. Methods of Obtaining a Plant Product

The present invention also relates to a process for obtaining a commodity product, comprising harvesting and/or milling the grains from a crop comprising an HPPD sequence of the invention to obtain the commodity product. Agronomically and commercially important products and/or compositions of matter including but not limited to animal feed, commodities, and plant products and by-products that are intended for use as food for human consumption or for use in compositions and commodities that are intended for human consumption, particularly devitalized seed/grain products, including a (semi-)processed products produced from such grain/seeds, wherein said product is or comprises whole or processed seeds or grain, animal feed, corn or soy meal, corn or soy flour, corn, corn starch, soybean meal, soy flour, flakes, soy protein concentrate, soy protein isolates, texturized soy protein concentrate, cosmetics, hair care products, soy nut butter, natto, tempeh, hydrolyzed soy protein, whipped topping, shortening, lecithin, edible whole soybeans (raw, roasted, or as edamame), soy yogurt, soy cheese, tofu, yuba, as well as cooked, polished, steamed, baked or parboiled grain, and the like are intended to be within the scope of the present invention if these products and compositions of matter contain detectable amounts of the nucleotide and/or amino acid sequences set forth herein as being diagnostic for any plant containing such nucleotide sequences.

The following examples are offered by way of illustration and not by way of limitation.

EXPERIMENTAL

Example 1: First Generation Point Mutant Library

The HPPD PfEvo33 mutant (described in International Patent Application No PCT/US2013/59598 (filed on Sep. 13, 2013) and set forth herein as SEQ ID NO:5) was mutagenized at positions 334 and 336. Saturated mutagenesis of these positions was carried out using the QUIKCHANGE® lightning kit. Mutants were pooled and transformed into DH5alpha E. coli cells. Six hundred individual clones were screened for tolerance to the HPPD inhibitor tembotrione (TBT). The clones were grown in LB media plus kanamycin at 37 degrees C. in a shaker until an OD600 nm of 0.3 was reached. Cultures were then switched to 30 degrees C. and incubated for an additional 17 hours. Cultures were spun down and cell pellets resuspended in 10 mM Hepes/KOH pH 7.6, 4 mM MgCl2, 1 mM DTT. The cells were lysed by bead beating and soluble cell extracts were obtained after centrifugation.

The mutants were analyzed using a brown color assay. Specifically, the HPPD extracts were assayed in 96 well format for HPPD inhibitor tolerance by spotting on solid media containing LB-agar, kanamycin, 5 mM tyrosine, 42 mM succinate and an HPPD inhibitor. In the primary screen, 20 ul extract was spotted in triplicate on plates containing 250, 500, 1000, or 2000 uM tembotrione. Plates were covered with airpore tape and incubated at 37 degrees C. After 24 hours, brown pigment formation was visually compared to a sample containing PfHPPD and PfEvo33. Variants showing darker brown color formation than PfEvo33 in the presence of TBT were re-assayed on 0, 500, 1000, 2000 uM TBT, and 500, 1000, 2000 uM diketonitrile (DKN, the active compound of isoxaflutole (IFT)), and 500, 1000, 2000 uM Mesotrione. Those variants that again showed darker brown color were again expressed, and extract was titrated on all the tested HPPD inhibitors to determine the extent of improvement.

The two clones showing the darkest color were the double mutants PfE335P-G336F and PfE335P-G336Y (which are referred to herein as PfEvo43 (SEQ ID NO:7) and PfEvo44 (SEQ ID NO:8), respectively). These proteins were produced in E. coli, purified and their activity was tested using the HPPD assays described below.

Example 2: Production and Purification HPPD Proteins and Determination of HPPD Activity in Presence of HPPD Inhibitor Herbicides HPPD proteins were produced and purified as described in WO2011/076882. The activity of HPPD proteins in absence or presence of HPPD inhibitors was determined using either the so called OD assay or the HGD assay.

a) The OD assay: The HPPD activity was determined colourimetrically by measuring the amount of HPP remaining in the assay mixture at the end of the incubation period after derivatisation of HPP with 2,4-dinitrophenylhydrazine (DNP) to form an amber-brown colored 2,4-dinitrophenylhydrazone under alkaline conditions. The assay was carried out at room temperature in Greiner F-bottom 96 well microplates. The assay mixture contained 50 mM Tris-HCl pH 7.8, 0.5 mM HPP, 10 mM ascorbate, 650 units of catalase and appropriate amounts of purified HPPD enzyme in a total assay volume of 100 µl. The reaction was started by the addition of enzyme. After an incubation time of 24 minutes, the reaction was stopped by the addition of 50 µl of a solution of 0.04% DNP dissolved in 3.8 N HCl. After a further 15-minute incubation period 100 µl of a 5 N KOH solution was added to the reaction mixture and the amount of unconsumed HPP was measured photometrically at 405 nm. Enzyme activity was calculated as the difference in E405 between assays lacking enzyme (negative control) and the enzyme containing assays (ΔE405=E405(negative control)−E405). Enzyme activity (nmol substrate consumed per min) was calculated from a calibration curve generated from HPP. pI50-values (the negative log value of the concentration of inhibitor necessary to inhibit 50% of the enzyme activity in molar concentration were determined from dose-response plots of HPPD activity versus inhibitor concentration tested ($5.0 \times 10^{-6}$, $1.0 \times 10^{-5}$, $2.5 \times 10^{-5}$, $4.0 \times 10^{-5}$, $7.0 \times 10^{-5}$, $1.0 \times 10^{-4}$, $2.0 \times 10^{-4}$ and $5.0 \times 10^{-4}$M) using the 4 Parameter Logistic Model or Sigmoidal Dose-Response Model of the ID Business Solutions Ltd. XLfit software suite. The result ">5.6" means that the inhibition at the lowest inhibitor concentration tested was higher than 85% and the pI50-value could therefore not be precisely calculated within in the range of concentration of inhibitor tested. The result "<2.5" means that the inhibition at the highest inhibitor concentration tested was lower than 25% and the pI50-value could therefore not be precisely calculated within in the range of concentration of inhibitor tested. "n.d." means not determined.

b) The HGD assay: With the HGD assay HPPD activity was measured at room temperature by adding appropriate amounts of HPPD to a solution of 200 mM Tris-HCl pH 7.6, 10 mM ascorbate, 20 µM $FeSO_4$, 650 units of catalase, 8 µg HGA dioxygenase (HGA: homogentisate) and 600 µM HPP in a total volume of 1 ml. Initial reaction rates in the absence or presence of inhibitors were determined from the increase in absorbance at 318 nm due to the formation of maleylacetoacetate (ε318=11,900 M−1 cm-1). pI50-values (the negative log value of the concentration of inhibitor necessary to inhibit 50% of the enzyme activity in molar concentration were determined from dose-response plots of HPPD activity versus inhibitor concentration tested using the 4 Parameter Logistic Model or Sigmoidal Dose-Response Model of the ID Business Solutions Ltd. XLfit software suite. Due to the UV absorption of the HPPD inhibitors tested, inhibitor concentrations >100 µM could not be tested. The result "<4" means that the inhibition at 100 µM inhibitor concentration was lower than 25% and the pI50-value could therefore not be precisely calculated within in the range of concentration of inhibitor tested. "n.d." means not determined.

The HGD assay allowed to continuously follow HPPD-catalyzed HGA formation over time was therefore used to determine the inhibition type of the HPPD inhibitors tested. When in the presence of an inhibitor the HPPD activity was found to decrease in a time-dependent manner characteristic for slow-binding or slow, tight-binding inhibitors (for a definition see Morrison (1982) Trends Biochem. Sci. 7, 102-105), the inhibitor was called time-dependent (abbreviation "td"). When in the presence of an inhibitor the HPPD activity was inhibited but the inhibition was found not to decrease in a time-dependent manner, the inhibitor was called reversible (abbreviation "rev").

The abbreviation "no-in" means that the type of inhibition could not be determined due to the fact that no inhibition of the corresponding HPPD variant was observed at 100 µM inhibitor concentration.

When the tolerance of the HPPD proteins PfEvo43 and PfEvo44 against diketonitrile (DKN) and mesotrione (MST) was determined by using the OD assay, it became evident that their tolerance was improved compared to reference HPPD proteins PfHPPD, PfG336F, PfG336Y, PfG336W, C959, and PfEvo33 (see Table 2).

TABLE 2

Evaluation of tolerance (pI50) of first generation HPPD enzymes against diketonitrile (DKN) and mesotrione (MST) using the OD assay

| Clone | SEQ ID NO | Amino acid position in PfHPPD | | Activity DeltaE/ 24 min µg Protein | DKN | MST |
|---|---|---|---|---|---|---|
| | | 335 | 336 | | | |
| PfHPPD | 1 | E | G | 0.76 | >5.6 | >5.6 |
| PfG336F | 2 | E | F | 0.66 | 5.3 | 5.6 |
| PfG336Y | 3 | E | Y | 0.66 | 5.2 | 5.5 |
| PfG336W | 4 | E | W | 0.40 | 5.0 | 5.3 |
| C959 | 5 | P | G | 0.09 | 5.5 | >5.6 |
| PfEvo33 | 6 | P | W | 0.25 | 4.3 | 5.1 |
| PfEvo43 | 7 | P | F | 0.39 | 4.1 | 4.6 |
| PfEvo44 | 8 | P | Y | 0.41 | 4.0 | 4.6 |

When the tolerance of the HPPD proteins PfEvo43 and PfEvo44 against diketonitrile (DKN), tembotrione (TBT), and mesotrione (MST) was determined using the HGD assay, their tolerance was found to be significantly improved compared to reference HPPD proteins (for details, see Table 7, below). More importantly, analysis of the time-course of inhibition by diketonitrile (DKN), tembotrione (TBT), and mesotrione (MST) revealed, that the mechanism of inhibition of the HPPD proteins PfEvo43 and PfEvo44 significantly differed from the mechanism of inhibition of the reference HPPD proteins in such a way that it had changed from the time-dependent inhibition characteristic for slow-binding or slow, tight-binding inhibitors to fully reversible inhibition (for details, see Table 11, below).

Example 3: Second Generation Point Mutant Library

PfEvo43 and PfEvo44 obtained as described in Example 1 were used for creating HPPD proteins further containing amino acid exchanges at positions 339 and 340 using the QUIKCHANGE® lightning kit. Their tolerance towards HPPD inhibitors determined with the OD assay is summarized in Table 3.

TABLE 3

Evaluation of tolerance (pI50) of second generation HPPD enzymes to diketonitrile (DKN), tembotrione (TBT), mesotrione (MST), and Cmpd. 2 (2-chloro-3-ethoxy-4-(methylsulfonyl)-N-(1-methyl-1H-tetrazol-5-yl)benzamide) using the OD assay.

| Clone | SEQ ID NO | Amino acid position in PfHPPD | | | | Activity DeltaE/ 24 min µg Protein | HPPD inhibitors | | | |
|---|---|---|---|---|---|---|---|---|---|---|
| | | 335 | 336 | 339 | 340 | | DKN | TBT | MST | Cmpd. 2 |
| PfHPPD | 1 | E | G | K | A | 0.76 | >5.6 | >5.6 | >5.6 | >5.6 |
| PfEvo43 | 7 | P | F | K | A | 0.39 | 4.1 | >5.6 | 4.6 | >5.6 |
| FLP129 | 9 | P | F | A | Q | 0.36 | 3.3 | 4.8 | 3.7 | 5.4 |
| FLP130 | 10 | P | F | K | E | 0.39 | 3.2 | 4.8 | 3.7 | 5.5 |
| PfEvo44 | 8 | P | Y | K | A | 0.41 | 4.0 | >5.6 | 4.6 | n.d. |
| K131 | 13 | P | Y | A | Q | 0.50 | 3.3 | 4.8 | 3.7 | n.d. |
| K132 | 14 | P | Y | K | E | 0.50 | 3.1 | 4.8 | 3.7 | n.d. |

The tolerance of the HPPD proteins FLP129, FLP130, K131, and K132 against diketonitrile (DKN), and/or tembotrione (TBT), and/or mesotrione (MST) was significantly improved compared to the reference HPPD proteins PfHPPD, PfG336F, PfG336Y, PfG336W, C959, and PfEvo33. When the tolerance of the HPPD proteins FLP129 and FLP130 against diketonitrile (DKN), and/or tembotrione (TBT), and/or mesotrione (MST) was determined using the HGD assay, their tolerance was also found to be significantly improved compared to reference HPPD proteins PfHPPD, PfG336F, PfG336Y, PfG336W, C959, and PfEvo33 (for details, see Table 7, below). Analysis of the time-course of inhibition revealed, that diketonitrile (DKN), tembotrione (TBT), and mesotrione (MST) were fully reversible inhibitors of the HPPD proteins FLP129 and FLP130 (for details, see Table 11, below). Analysis of the time-course of inhibition of Cmpd. 2 against the HPPD proteins K131 and K132 revealed, that Cmpd. 2 was a fully reversible inhibitor of the HPPD proteins K131 and K132 (for details, see Table 12, below).

Example 4: Third Generation Point Mutant Library

The HPPD variants obtained as described in Example 3 were used for creating HPPD proteins further containing amino acid exchanges at position 215 using the QUIKCHANGE® lightning kit. Their tolerance towards HPPD inhibitors determined with the OD assay is summarized in Table 4. K299 carrying only the P215L mutation was used as a second reference in addition to PfHPPD.

TABLE 4

Evaluation of tolerance (pI50) of third generation HPPD enzymes to diketonitrile (DKN), tembotrione (TBT), mesotrione (MST), and Cmpd. 2 (2-chloro-3-ethoxy-4-(methylsulfonyl)-N-(1-methyl-1H-tetrazol-5-yl)benzamide) using the OD assay

| Clone | SEQ ID NO: | Amino acid position in PfHPPD | | | | | Activity Delta E/ 24 min μg protein | HPPD inhibitors | | | |
|---|---|---|---|---|---|---|---|---|---|---|---|
| | | 215 | 335 | 336 | 339 | 340 | | DKN | TBT | MST | Cmpd. 2 |
| PfHPPD | 1 | P | E | G | K | A | 0.76 | >5.6 | >5.6 | >5.6 | >5.6 |
| K299 | 20 | L | E | G | K | A | 0.17 | 5.1 | >5.6 | 5.5 | >5.6 |
| PfEvo43 | 7 | P | P | F | K | A | 0.39 | 4.1 | >5.6. | 4.6 | >5.6 |
| FLP202 | 12 | L | P | F | K | E | 0.09 | <2.5 | 3.6 | <2.5 | 4.5 |
| FLP136 | 11 | L | P | F | K | A | 0.09 | 2.6 | 4.7 | 3.3 | 4.8 |
| FLP129 | 9 | P | P | F | A | Q | 0.36 | 3.3 | 4.8 | 3.7 | 5.4 |
| FLP130 | 10 | P | P | F | K | E | 0.39 | 3.2 | 4.8 | 3.7 | 5.5 |
| PfEvo44 | 8 | P | P | Y | K | A | 0.41 | 4.0 | >5.6 | 4.6 | n.d. |
| K203 | 16 | L | P | Y | K | E | 0.08 | <2.5 | 3.9 | 3.0 | n.d. |
| K137 | 15 | L | P | Y | K | A | 0.12 | 2.8 | 4.7 | 3.4 | n.d. |
| K131 | 13 | P | P | Y | A | Q | 0.50 | 3.3 | 4.8 | 3.7 | n.d. |
| K132 | 14 | P | P | Y | K | E | 0.50 | 3.1 | 4.8 | 3.7 | n.d. |

The tolerance of the HPPD proteins carrying the P215L mutation against diketonitrile (DKN), tembotrione (TBT), and mesotrione (MST) was significantly improved compared to the reference HPPD proteins. When the tolerance of the HPPD proteins FLP136 and FLP202 against diketonitrile (DKN), tembotrione (TBT), and mesotrione (MST) was determined using the HGD assay, their tolerance was also found to be significantly improved compared to the reference HPPD proteins (for details, see Table 7, below). Analysis of the time-course of inhibition revealed, that diketonitrile (DKN), tembotrione (TBT), and mesotrione (MST) were fully reversible inhibitors of the HPPD proteins FLP136 and FLP202 (for details, see Table 11, below). Analysis of the time-course of inhibition of Cmpd. 2 against the HPPD proteins K137 and K203 revealed, that Cmpd. 2 was a fully reversible inhibitor of the HPPD proteins K137 and K203 (for details, see Table 12, below).

Example 5: Fourth Generation Point Mutant Library

The HPPD variant FLP202 obtained as described in Example 4 was used for creating HPPD proteins containing further amino acid exchanges at position 215 using the QUIKCHANGE® lightning kit. Their tolerance towards HPPD inhibitors determined with the OD assay is summarized in Table 5.

TABLE 5

Evaluation of tolerance (pI50) of fourth generation HPPD enzymes to diketonitrile (DKN), tembotrione (TBT), mesotrione (MST), and Cmpd. 2 (2-chloro-3-ethoxy-4-(methylsulfonyl)-N-(1-methyl-1H-tetrazol-5-yl)benzamide) using the OD assay

| Clone | SEQ ID NO | Amino acid positions | | | | Activity DeltaE/ 24 min μg Protein | HPPD inhibitors | | | |
|---|---|---|---|---|---|---|---|---|---|---|
| | | 215 | 335 | 336 | 340 | | DKN | TBT | MST | Cmpd. 2 |
| FLP130 | 10 | P | P | F | E | 0.39 | 3.2 | 4.8 | 3.7 | 5.5 |
| FLP202 | 12 | L | P | F | E | 0.09 | <2.5 | 3.6 | <2.5 | 4.5 |
| K255 | 18 | A | P | F | E | 0.09 | 3.0 | 4.5 | 3.7 | 5.0 |
| K258 | 19 | N | P | F | E | 0.15 | <2.5 | 4.4 | 3.4 | 5.4 |

The tolerance of the HPPD proteins K255 and K258 against diketonitrile (DKN), tembotrione (TBT), and mesotrione (MST) was significantly improved compared to the reference HPPD proteins. Analysis of the time-course of inhibition of Cmpd. 2 against the HPPD proteins K255 and K258 revealed, that Cmpd. 2 was a fully reversible inhibitor of the HPPD proteins K255 and K258 (for details, see Table 12, below).

Example 6: Fifth Generation Point Mutant Library

The HPPD variants FLP130 obtained as described in Example 3 and FLP202 obtained as described in Example 4 were used for creating HPPD proteins containing further amino acid exchanges at positions 226 and 340 using the QUIKCHANGE® lightning kit. Their tolerance towards HPPD inhibitors determined with the OD assay is summarized in Table 6.

TABLE 6

Evaluation of tolerance (pI50) of fourth generation of HPPD enzymes to diketonitrile (DKN), tembotrione (TBT), mesotrione (MST), and Cmpd. 2 (2-chloro-3-ethoxy-4-(methyl-sulfonyl)-N-(1-methyl-1H-tetrazol-5-yl)benzamide) using the OD assay

| Clone | SEQ ID NO: | Amino acid position in PfHPPD | | | | | Activity DeltaE/ 24 min µg Protein | HPPD inhibitors | | | |
|---|---|---|---|---|---|---|---|---|---|---|---|
| | | 215 | 226 | 335 | 336 | 339 | 340 | | DKN | TBT | MST | Cmpd. 2 |

| Clone | SEQ ID NO: | 215 | 226 | 335 | 336 | 339 | 340 | Activity | DKN | TBT | MST | Cmpd. 2 |
|---|---|---|---|---|---|---|---|---|---|---|---|---|
| FLP202 | 12 | L | Q | P | F | K | E | 0.09 | <2.5 | 3.6 | <2.5 | 4.5 |
| K300 | 21 | L | Q | P | F | K | G | 0.01 | <2.5 | 3.1 | <2.5 | 3.8 |
| K306 | 24 | L | H | P | F | K | E | 0.01 | <2.5 | 4.8 | 3.7 | 5.1 |
| K363 | 29 | P | H | P | F | K | E | 0.20 | 3.8 | 5.5 | 4.3 | 5.4 |

The tolerance of the HPPD proteins K300 and K306 against diketonitrile (DKN), tembotrione (TBT), and mesotrione (MST) was improved compared to the reference HPPD proteins. Analysis of the time-course of inhibition of Cmpd. 2 against the HPPD proteins K300, K306, and K363 revealed, that Cmpd. 2 was a fully reversible inhibitor of the HPPD proteins K300, K306, and K363 (for details, see Table 12, below).

Example 7: Tolerance of HPPD Variants Created as Described in Examples 1 to 6 to HPPD Inhibitors Determined with the HGD Assay The tolerance of the HPPD variants created in Examples 1 to 6 against diketonitrile (DKN), tembotrione (TBT), and mesotrione (MST) determined with the HGD assay is summarized in Table 7.

TABLE 7

Evaluation of tolerance (pI50) of the HPPD variants created in Examples 1 to 6 to diketonitrile (DKN), tembotrione (TBT), and mesotrione (MST) using the HGD assay

| Clone | SEQ ID NO | Position of the mutations in PfHPPD | | | | | HPPD inhibitor DKN | HPPD inhibitor TBT | HPPD inhibitor MST |
|---|---|---|---|---|---|---|---|---|---|
| | | 215 | 335 | 336 | 339 | 340 | | | |
| PfHPPD | 1 | P | E | G | K | A | 5.8 | 6.4 | 5.8 |
| PfG336W | 4 | P | E | W | K | A | 5.3 | 6.1 | 5.5 |
| PfG336F | 2 | P | E | F | K | A | 5.1 | 5.9 | 5.1 |
| PfG336Y | 3 | P | E | Y | K | A | 4.9 | 5.5 | 5.0 |
| PfEvo33 | 6 | P | P | W | K | A | 4.6 | 6.2 | 5.5 |
| PfEvo43 | 7 | P | P | F | K | A | 4.0 | 6.0 | 5.1 |
| PfEvo44 | 8 | P | P | Y | K | A | 4.1 | 5.9 | 5.2 |
| FLP129 | 9 | P | P | F | A | Q | 4.6 | 6.2 | 5.0 |
| FLP130 | 10 | P | P | F | K | E | 4.3 | 6.2 | 5.3 |
| FLP136 | 11 | L | P | E | K | A | 4.0 | 5.3 | 4.5 |
| FLP202 | 12 | L | P | F | K | E | <4 | 4.2 | <4 |

The tolerance of the HPPD variants created in Examples 1 to 6 against Cmpd. 1 (2-methyl-N-(5-methyl-1,3,4-oxadiazol-2-yl)-3-(methylsulfonyl)-4-(trifluoromethyl)benzamide), Cmpd. 2 (2-chloro-3-ethoxy-4-(methylsulfonyl)-N-(1-methyl-1H-tetrazol-5-yl)benzamide), Cmpd. 3 (4-(difluoromethyl)-2-methoxy-3-(methylsulfonyl)-N-(1-methyl-1H-tetrazol-5-yl)benzamide), Cmpd. 4 (2-chloro-3-(methylsulfanyl)-N-(1-methyl-1H-tetrazol-5-yl)-4-(trifluoromethyl)benzamide), and Cmpd. 5 (2-(methoxymethyl)-3-(methylsulfinyl)-N-(1-methyl-1H-tetrazol-5-yl)-4-(trifluoromethyl)benzamide) determined with the HGD assay is summarized in Table 8.

The combination of mutations at the positions 188 and 189 with mutations at the positions 215, 335, 336 and 340 influence positively the level of activity of the enzymes, which still display very high level of tolerance to the inhibitors. Analysis of the time-course of inhibition of Cmpd. 2 against the HPPD proteins K250, K325, and K357 revealed, that Cmpd. 2 was a fully reversible inhibitor of the HPPD proteins K250, K325, and K357. The pI50-values of Cmpd. 2 against the HPPD proteins K250, K325, and K357 were determined as <4, 5.5, and 5.1, respectively.

TABLE 8

Evaluation of tolerance (pI50) of the HPPD variants created in Examples 1 to 6 using the HGD assay

| Clone | SEQ ID NO | Position of the mutations in PfHPPD | | | | | | HPPD inhibitor herbicides | | | | |
|---|---|---|---|---|---|---|---|---|---|---|---|---|
| | | 215 | 226 | 335 | 336 | 339 | 340 | Cmpd. 2 | Cmpd. 1 | Cmpd. 3 | Cmpd. 4 | Cmpd. 5 |
| PfHPPD | 1 | P | Q | E | G | K | A | 6.7 | 6.3 | 6.6 | 7.0 | 6.1 |
| PfG336W | 4 | P | Q | E | W | K | A | 6.8 | 6.2 | 6.4 | 6.7 | 6.1 |
| FLP129 | 9 | P | Q | P | F | A | Q | 5.8 | 6.1 | 5.9 | 6.6 | 6.1 |
| FLP130 | 10 | P | Q | P | F | K | E | 6.2 | 6.2 | 6.4 | 6.6 | 6.0 |
| K131 | 13 | P | Q | P | Y | A | Q | 6.2 | n.d. | n.d. | n.d. | n.d. |
| K132 | 14 | P | Q | P | Y | K | E | 5.9 | 5.5 | n.d. | 6.9 | n.d. |
| K137 | 15 | L | Q | P | Y | K | A | 5.5 | n.d. | n.d. | n.d. | n.d. |
| K203 | 16 | L | Q | P | Y | K | E | 5.3 | n.d. | n.d. | n.d. | n.d. |
| FLP136 | 11 | L | Q | P | E | K | A | 5.9 | 5.6 | 5.6 | 6.0 | 5.6 |
| FLP202 | 12 | L | Q | P | F | K | E | 4.7 | 4.1 | 4.3 | 5.7 | 4.3 |
| K255 | 18 | A | Q | P | F | K | E | 4.5 | n.d. | n.d. | n.d. | n.d. |
| K258 | 19 | N | Q | P | F | K | E | 5.4 | n.d. | n.d. | n.d. | n.d. |
| K300 | 21 | L | Q | P | F | K | G | 4.3 | n.d. | n.d. | n.d. | n.d. |
| K306 | 24 | L | H | P | F | K | E | 4.9 | n.d. | n.d. | n.d. | n.d. |
| K363 | 29 | P | H | P | F | K | E | 5.5 | n.d. | n.d. | n.d. | n.d. |

Example 8: Sixth Generation Point Mutant Library

The HPPD variants FLP130 obtained as described in Example 3, FLP202 obtained as described in Example 4 and K255 and K258 obtained as described in Example 5 were used for creating HPPD proteins containing further amino acid exchanges at positions 188 and 189 using the QUIKCHANGE® lightning kit. Their tolerance towards HPPD inhibitors determined with the OD assay is summarized in Table 9.

Example 9: Seventh Generation Point Mutant Library

The HPPD variants FLP130 obtained as described in Example 3 and FLP202 obtained as described in Example 4 were used for creating HPPD proteins containing further amino acid exchanges at position 200 using the QUIKCHANGE® lightning kit. The tolerance towards HPPD inhibitors determined with the OD assay is summarized in Table 10.

TABLE 9

Evaluation of tolerance (pI50) of sixth generation HPPD enzymes to diketonitrile (DKN), tembotrione (TBT), mesotrione (MST), and Cmpd. 2 (2-chloro-3-ethoxy-4-(methylsulfonyl)-N-(1-methyl-1H-tetrazol-5-yl)benzamide) using the OD assay

| Clone | SEQ ID NO: | Amino acid position in PfHPPD 188 | 189 | 215 | 335 | 336 | 340 | Activity DeltaE/ 24 min µg Protein | HPPD inhibitors DKN | TBT | MST | Cmpd. 2 |
|---|---|---|---|---|---|---|---|---|---|---|---|---|
| FLP202 | 12 | A | R | L | P | F | E | 0.09 | <2.5 | 3.6 | 2.5 | 4.5 |
| K258 | 19 | A | R | N | P | F | E | 0.15 | <2.5 | 4.4 | 3.4 | 5.4 |
| K357 | 26 | G | C | P | P | F | E | 0.47 | 3.5 | 5.3 | 4.1 | 5.4 |
| K250 | 17 | G | C | L | P | F | E | 0.07 | <2.5 | 3.8 | 3.0 | 4.6 |
| K325 | 25 | G | C | N | P | F | E | 0.41 | <2.5 | 4.6 | 3.6 | 5.6 |
| K405 | 30 | G | C | A | P | F | E | 0.16 | 3.3 | 4.8 | 3.7 | 4.9 |
| K406 | 31 | G | G | N | P | F | E | 0.52 | <2.5 | 4.5 | 3.5 | 5.6 |
| K407 | 32 | G | E | N | P | F | E | 0.41 | <2.5 | 4.6 | 3.6 | 5.7 |
| K408 | 33 | G | D | N | P | F | E | 0.56 | <2.5 | 4.6 | 3.6 | 5.7 |

TABLE 10

Evaluation of tolerance (pI50) of seventh generation of HPPD enzymes to diketonitrile (DKN), tembotrione (TBT), mesotrione (MST), and Cmpd. 2 (2-chloro-3-ethoxy-4-(methylsulfonyl)-N-(1-methyl-1H-tetrazol-5-yl)benzamide) using the OD assay.

| Clone | SEQ ID NO | Amino acid position in PfHPPD | | | | | Activity DeltaE/ 24 min µg Protein | HPPD inhibitors | | | |
|---|---|---|---|---|---|---|---|---|---|---|---|
| | | 200 | 215 | 335 | 336 | 340 | | DKN | TBT | MST | Cmpd. 2 |
| FLP202 | 12 | L | L | P | F | E | 0.09 | 2.5 | 3.6 | 2.5 | 4.5 |
| K303 | 22 | I | L | P | F | E | 0.008 | 2.5 | 4.2 | 3.2 | 4.6 |
| K304 | 23 | M | L | P | F | E | 0.011 | 2.5 | 4.2 | 3.2 | 4.6 |
| K360 | 27 | I | P | P | F | E | 0.28 | 3.6 | 5.3 | 4.3 | 5.3 |
| K361 | 28 | M | P | P | F | E | 0.21 | 3.4 | 5.1 | 4.0 | 5.2 |

The combination of mutations at the position 200 with mutations at the positions 215, 335, 336 and 340 results in HPPD variants which still display high level of tolerance to HPPD inhibitors. Analysis of the time-course of inhibition of Cmpd. 2 against the HPPD proteins K303, K304, K360 and K361 revealed, that Cmpd. 2 was a fully reversible inhibitor of the HPPD proteins K303, K304, K360 and K361 (see Table 12 below). The pI50-values of Cmpd. 2 against the HPPD proteins K303, K304, K360, and K361 were determined as 5.0, 4.7, 5.5, and 5.3, respectively.

Example 10: Analysis of the Type of Inhibition of HPPD Variants by HPPD Inhibitors The type of inhibition by various HPPD inhibitors of the HPPD variants obtained as described in Examples 1 to 9, determined using the HGD-assay described above, is summarized in Table 11 and Table 12.

TABLE 11

Type of inhibition of HPPD variants by DKN (diketonitrile), TBT (tembotrione), and MST (mesotrione) determined using the HGD-assay.

| Clone | SEQ ID NO | Position of the mutations in PfHPPD | | | | | HPPD inhibitor herbicides | | |
|---|---|---|---|---|---|---|---|---|---|
| | | 215 | 335 | 336 | 339 | 340 | DKN | TBT | MST |
| PfHPPD | 1 | P | E | G | K | A | td | td | td |
| PfG336W | 4 | P | E | W | K | A | td | td | td |
| PfG336F | 2 | P | E | F | K | A | td | td | td |
| PfG336Y | 3 | P | E | Y | K | A | td | td | td |
| PfEvo33 | 6 | P | P | W | K | A | td | td | td |
| PfEvo43 | 7 | P | P | F | K | A | rev | rev | rev |
| PfEvo44 | 8 | P | P | Y | K | A | rev | rev | rev |
| FLP129 | 9 | P | P | F | A | Q | rev | rev | rev |
| FLP130 | 10 | P | P | F | K | E | rev | rev | rev |
| FLP136 | 11 | L | P | F | K | A | rev | rev | rev |
| FLP202 | 12 | L | P | F | K | E | no-in | rev | no-in |

TABLE 12

Type of inhibition of HPPD variants by Cmpd. 1 (2-methyl-N-(5-methyl-1,3,4-oxadiazol-2-yl)-3-(methylsulfonyl)-4-(trifluoromethyl)benzamide), Cmpd. 2 (2-chloro-3-ethoxy-4-(methylsulfonyl)-N-(1-methyl-1H-tetrazol-5-yl)benzamide), Cmpd. 3 (4-(difluoromethyl)-2-methoxy-3-(methylsulfonyl)-N-(1-methyl-1H-tetrazol-5-yl)benzamide), Cmpd. 4 (2-chloro-3-(methylsulfanyl)-N-(1-methyl-1H-tetrazol-5-yl)-4-(trifluoromethyl)benzamide), and Cmpd. 5 (2-(methoxymethyl)-3-(methylsulfinyl)-N-(1-methyl-1H-tetrazol-5-yl)-4 (trifluoromethyl)benzamide)determined using the HGD-assay.

| Clone | SEQ ID NO | Position of the mutations in PfHPPD | | | | | | | HPPD inhibitor herbicides | | | | |
|---|---|---|---|---|---|---|---|---|---|---|---|---|---|
| | | 200 | 215 | 226 | 335 | 336 | 339 | 340 | Cmpd. 2 | Cmpd. 1 | Cmpd. 3 | Cmpd. 4 | Cmpd. 5 |
| PfHPPD | 1 | L | P | Q | E | G | K | A | td | td | td | td | td |
| PfG336W | 4 | L | P | Q | E | W | K | A | td | td | td | td | td |
| FLP129 | 9 | L | P | Q | P | F | A | Q | rev | rev | rev | rev | rev |
| FLP130 | 10 | L | P | Q | P | F | K | E | rev | rev | rev | rev | rev |
| K131 | 13 | L | P | Q | P | Y | A | Q | rev | n.d. | n.d. | n.d. | n.d. |
| K132 | 14 | L | P | Q | P | Y | K | E | rev | rev | n.d. | rev | n.d. |

TABLE 12-continued

Type of inhibition of HPPD variants by Cmpd. 1 (2-methyl-N-(5-methyl-1,3,4-oxadiazol-2-yl)-3-(methylsulfonyl)-4-(trifluoromethyl)benzamide), Cmpd. 2 (2-chloro-3-ethoxy-4-(methylsulfonyl)-N-(1-methyl-1H-tetrazol-5-yl)benzamide), Cmpd. 3 (4-(difluoromethyl)-2-methoxy-3-(methylsulfonyl)-N-(1-methyl-1H-tetrazol-5-yl)benzamide), Cmpd. 4 (2-chloro-3-(methylsulfanyl)-N-(1-methyl-1H-tetrazol-5-yl)-4-(trifluoromethyl)benzamide), and Cmpd. 5 (2-(methoxymethyl)-3-(methylsulfinyl)-N-(1-methyl-1H-tetrazol-5-yl)-4 (trifluoromethyl)benzamide)determined using the HGD-assay.

| Clone | SEQ ID NO | 200 | 215 | Position of the mutations in PfHPPD | | | | | HPPD inhibitor herbicides | | | | |
|---|---|---|---|---|---|---|---|---|---|---|---|---|---|
| | | | | 226 | 335 | 336 | 339 | 340 | Cmpd. 2 | Cmpd. 1 | Cmpd. 3 | Cmpd. 4 | Cmpd. 5 |
| K137 | 15 | L | L | Q | P | Y | K | A | rev | n.d. | n.d. | n.d. | n.d. |
| K203 | 16 | L | L | Q | P | Y | K | E | rev | n.d. | n.d. | n.d. | n.d. |
| FLP136 | 11 | L | L | Q | P | F | K | A | rev | rev | rev | rev | rev |
| FLP202 | 12 | L | L | Q | P | F | K | E | rev | rev | rev | rev | rev |
| K255 | 18 | L | A | Q | P | F | K | E | rev | n.d. | n.d. | n.d. | n.d. |
| K258 | 19 | L | N | Q | P | F | K | E | rev | n.d. | n.d. | n.d. | n.d. |
| K300 | 21 | L | L | Q | P | F | K | G | rev | n.d. | n.d. | n.d. | n.d. |
| K363 | 29 | L | P | H | P | F | K | E | rev | n.d. | n.d. | n.d. | n.d. |
| K306 | 24 | L | L | H | P | F | K | E | rev | n.d. | n.d. | n.d. | n.d. |
| K303 | 22 | I | L | Q | P | F | K | E | rev | n.d. | n.d. | n.d. | n.d. |
| K304 | 23 | M | L | Q | P | F | K | E | rev | n.d. | n.d. | n.d. | n.d. |
| K360 | 27 | I | P | Q | P | F | K | E | rev | n.d. | n.d. | n.d. | n.d. |
| K361 | 28 | M | P | Q | P | F | K | E | rev | n.d. | n.d. | n.d. | n.d. |

All of the HPPD variants obtained as described in Examples 1 to 9 have either no or only a significantly reduced affinity to HPPD inhibitors and at the same time the rate of dissociation of the respective inhibitor off these HPPD enzymes is increased to such an extent that the HPPD inhibitors no longer act as slow-binding or slow, tight-binding inhibitors but have become fully reversible inhibitors.

Example 11: Soybean Transformation

Soybean transformation is achieved using methods well known in the art, such as the one described using the *Agrobacterium tumefaciens* mediated transformation soybean half-seed explants using essentially the method described by Paz et al. (2006), Plant cell Rep. 25:206. Transformants were identified using tembotrione or isoxaflutole as selection marker. The appearance of green shoots was observed, and documented as an indicator of tolerance to the herbicide isoxaflutole or tembotrione. The tolerant transgenic shoots showed normal greening comparable to wild-type soybean shoots not treated with isoxaflutole or tembotrione, whereas wild-type soybean shoots treated with the same amount of isoxaflutole or tembotrione were entirely bleached. This indicated that the presence of the HPPD protein enables the tolerance to HPPD inhibitor herbicides, like isoxaflutole or tembotrione.

Tolerant green shoots were transferred to rooting media or grafted. Rooted plantlets were placed into soil and transferred to the greenhouse after an acclimation period. Plants containing the transgene were then sprayed with HPPD inhibitor herbicides, as for example with tembotrione at a rate of 100 g AI/ha or with mesotrione at a rate of 300 g AI/ha supplemented with ammonium sulfate methyl ester rapeseed oil. Ten days after the application the symptoms due to the application of the herbicide were evaluated and compared to the symptoms observed on wild type plants under the same conditions.

Example 12: Tolerance of Soybean Plants to Mesotrione

T0 soybean plants expressing an HPPD inhibitor tolerant enzyme of the present invention, along with a gene conferring tolerance to glyphosate and a gene conferring tolerance to glufosinate or having a "plant expression cassette", which includes only an HPPD inhibitor tolerant enzyme of the present invention, were tested for tolerance to mesotrione. Prior greenhouse trials with the transgenic plants, soy transformants were routinely analyzed for the expression and presence of the transgenes using the ELISA protein detection method (see detailed description under item D and H). Only plants recovering in the selection media and having a detectable HPPD transgene protein expression were used for the herbicide tolerance analysis. A DeVries Tracker Sprayer was calibrated prior to each spraying. The chemical formulation used for mesotrione (MST) testing was Callisto® 4 SC formulation supplemented with ammonium sulfate and methylated rape seed oil (Actirob). Spray tests were conducted using 3× the field rate (equivalent to 9 fluid ounce per acre of the same herbicide formulation that containing 40% the active ingredient (AI), mesotrione), which equals 316 grams AI per hectare. Tolerance was evaluated one week after spraying. Wild type soybean plants sprayed with the same herbicide formulation were totally bleached and exhibited 100% leaf damage. A tolerance rating of "0" was assigned to plants that their shoot apexes, newly emerged trifoliates and some axillary buds were completely bleached. A rating of "1" was assigned to plants having slight tolerance, i.e., the newest plant shoot tissues had some green leaves and are not bleached completely. A rating of "2" was assigned to plants showing moderate tolerance, i.e., more than 50% of the leaf area of the top three trifoliates showing no chlorosis or bleaching damage. A rating of "3" was assigned to plants showing nearly perfect tolerance, i.e., less than 10% of the leaf area showing chlorosis or very slight bleaching. The results are shown in Table 13.

TABLE 13

Evaluation of leaf area damage from transgenic T0 soybean events expressing different HPPD variants after seven days of treatment with mesotrione with a 3X field rate equivalent to 316 grams AI per hectare. A rating of "1" was assigned to plants having a slight tolerance, i.e., the newest plant shoot tissues had some green leaves and are not bleached completely. A rating of "2" was assigned to plants showing moderate tolerance, i.e., more than 50% of the leaf area of the top three trifoliates showing no chlorosis or bleaching damage. A rating of "3" was assigned to plants showing nearly perfect tolerance, i.e., less than 10% of the leaf area showing chlorosis or very slight bleaching. Different plant expression cassettes have been designed with either enzyme(s) conferring herbicide tolerance to HPPD inhibitors alone (HT-single) or tolerance to three different mode of action herbicide classes (HT-triple), i.e. HPPD inhibitors, glyphosate, and glufosinate.

| Clone HPPD variants | SEQ ID NO: | Plant expression cassette | Herbicide tolerance rating | | | | Total # of Plants |
|---|---|---|---|---|---|---|---|
| | | | 0 | 1 | 2 | 3 | |
| PfEvo43 | 7 | HT-triple | 6 | 18 | 26 | 20 | 70 |
| PfEvo43 | 7 | HT-single | 1 | 13 | 25 | 34 | 73 |
| PfEvo44 | 8 | HT-triple | 4 | 22 | 19 | 26 | 71 |
| PfEvo44 | 8 | HT-single | 7 | 14 | 43 | 21 | 85 |
| FLP136 | 11 | HT-triple | 4 | 17 | 33 | 19 | 73 |
| FLP136 | 11 | HT-single | 4 | 10 | 41 | 20 | 75 |
| FLP129 | 9 | HT-triple | 13 | 18 | 35 | 12 | 78 |
| FLP130 | 10 | HT-triple | 3 | 18 | 39 | 11 | 71 |
| FLP202 | 12 | HT-triple | 7 | 8 | 10 | 14 | 39 |
| FLP202 | 12 | HT-single | 2 | 21 | 37 | 18 | 78 |

Out of the 713 regenerated and selected transgenic transformants, more than 25% showed a high tolerance level with less than 10% damage of the total leaf area. Overall ~70% of the tested transgenic plants were visually ranked with a moderate to high tolerance rating.

In addition, expressing three different enzymes, which confer tolerance to three different modes of action classes (HPPD inhibitor compounds, glyphosate and glufosinate), did not interfere with the tolerance performance towards the HPPD inhibitor. Transgenic plants, which were only transformed with the HPPD inhibitor tolerant enzyme variant of the present invention, showed similar distribution of the ratings compared to the stacked events.

Example 13: Cotton T0 Plant Establishment and Selection

Cotton transformation was achieved using methods well known in the art, especially preferred method in the one described in the PCT patent publication WO 00/71733. Regenerated plants were transferred to the greenhouse. Following an acclimation period, sufficiently grown plants are sprayed with HPPD inhibitor herbicides as for example tembotrione equivalent to 100 or 200 gAI/ha supplemented with ammonium sulfate and methyl ester rapeseed oil. Seven days after the spray application, the symptoms due to the treatment with the herbicide were evaluated and compared to the symptoms observed on wild type cotton plants subjected to the same treatment under the same conditions.

Example 14: Transformation of Maize Plant Cells by *Agrobacterium*-Mediated Transformation Constructing the plant expression cassette for stable expression in the maize plant and maize transformation are well known in the art and in this particular example the methods were described and used from the PCT patent publication WO2014/043435 and WO2008/100353. The polynucleotide sequences encoding the HPPD variants in this application have been stacked with a DNA sequence encoding an EPSPS protein variant to confer tolerance to herbicides, which target the EPSPS. The EPSPS gene was isolated and mutated from *Arthrobacter globiformis* (WO2008/100353) and joined in-frame to a transit peptide sequence to guide translocation of the translated protein to the chloroplast. Stable expression was achieved with a ubiquitous promoter (Ubiquitin 4 promoter from sugarcane, U.S. Pat. No. 6,638,766), and a 35S terminator sequence from Cauliflower Mosaic Virus, which was cloned upstream and downstream of the EPSPS gene, respectively.

The corresponding HPPD variants were cloned with the same promoter, chloroplast transit peptide, and terminator sequence as described for the EPSPS gene expression cassette. The coding sequences for both genes have been codon optimized for maize expression. For the maize transformation ears are best collected 8-12 days after pollination. Embryos were isolated from the ears, and those embryos 0.8-1.5 mm in size were preferred for use in transformation. Embryos were plated scutellum side-up on a suitable incubation media, and incubated overnight at 25° C. in the dark.

However, it was not necessary per se to incubate the embryos overnight. Embryos are contacted with an *Agrobacterium* strain containing the appropriate vectors having a nucleotide sequence of the present invention for Ti plasmid mediated transfer for about 5-10 min, and then plated onto co-cultivation media for about 3 days (25° C. in the dark). After co-cultivation, explants were transferred to recovery period media for about five days (at 25° C. in the dark). Explants were incubated in selection media with glyphosate for up to eight weeks, depending on the nature and characteristics of the particular selection utilized. After the selection period, the resulting callus were transferred to embryo maturation media, until the formation of mature somatic embryos is observed. The resulting mature somatic embryos were then placed under low light, and the process of regeneration was initiated as known in the art. The resulting shoots were allowed to root on rooting media, and the resulting plants were transferred to nursery pots and propagated as transgenic plants. Plants were routinely analyzed for the expression and presence of the transgenes using the ELISA protein detection method. Only plants recovering in the selection media and having a detectable HPPD transgene protein expression were used for the herbicide tolerance analysis.

Example 15: Tolerance of Maize T0 Plants to HPPD Herbicides in Greenhouse Studies Regenerated T0 events from tissue culture were transplanted into two inch square pots with synthetic soil (Fafard® Mix) and controlled-released fertilizer (Haifa Multicote™; polymer-coated controlled-release fertilizer, NPK Pro 18-6-12+ Micronutrients) and cultivated in the greenhouse (GH) under supplementary high pressure sodium light for 12 days at a maximum of 30° C. during the day and a minimum of 22° C. at night. Fully recovered plants were transferred into five inch square pots filled with synthetic soil and control released fertilizer under the same environmental conditions. After seven days the T0 plants have been sprayed with 2-chloro-3-(methylsulfanyl)-N-(1-methyl-1H-tetrazol-5-yl)-4-(trifluoromethyl)benzamide (Cmpd. 4); at agronomic relevant concentration of 100 g AI/ha (with "g AI/ha" meaning "gram of active ingredient per hectare") prepared from a WP20 (wettable powder 20%) formulation supplemented with esterified vegetable oil mixture (Hasten™ spray adjuvants, 0.578% v/v) and ammonium sulphate (AMS, 0.97% w/v). The herbicide treatment was conducted in a DeVries Tracker Sprayer system with standard application protocols, which are well known in the art. As a spray control T0 events have been sprayed with the adjuvant mixture lacking the herbicide. All T0 events sprayed with this mixture did not show bleached leaves. If not stated otherwise, six days after treatment (DAT) of 2-chloro-3-(methylsulfanyl)-N-(1-methyl-1H-tetrazol-5-yl)-4-(trifluoromethyl)benzamide the damage of transgenic T0 events were evaluated.

T0 events, which express the EPSPS selectable marker gene and do not possess a HPPD variant type, were used as control maize plants and exhibited 100% leaf damage already at 25 g AI/ha of 2-chloro-3-(methylsulfanyl)-N-(1-methyl-1H-tetrazol-5-yl)-4-(trifluoromethyl)benzamide. Non-transformed maize plants also exhibited 100% leaf damage already at 25 g AI/ha of 2-chloro-3-(methylsulfanyl)-N-(1-methyl-1H-tetrazol-5-yl)-4-(trifluoromethyl)benzamide.

Table 14 summarizes the results of transgenic maize plants expressing the mutants FLP202 and FLP136 of the *Pseudomonas fluorescens* HPPD protein obtained as described in Example 14. Plants classified with a rating of "0" showed severe bleaching of the leaf at a range of 41% to 100% damage of the total leaf area. A rating of "1" was assigned to plants having a moderate tolerance with 16% to 40% damage of total leaf area. A rating of "2" was assigned to plants with good tolerance within the range of 6% to 15% damage of total leaf area. Plants with a rating of "3" showed almost no bleaching with 5% or less of the leaf area damaged by the herbicide treatment.

The results in Table 14 show that a significant portion of independent maize T0 events are tolerant to the HPPD herbicide 2-chloro-3-(methylsulfanyl)-N-(1-methyl-1H-tetrazol-5-yl)-4-(trifluoromethyl)benzamide at an agronomically relevant doses of 100 g AI/ha compared to control plants.

Approximately 40% of tested events expressing FLP136 (n=84) showed a good to high tolerance with 15% or less bleached leaf area after treatment with a 100 g AI/ha herbicide concentration of Cmpd. 4. Out of all tested FLP136 expressing maize plants, ~15% show less than 5% or no visual leaf damage.

A similar picture holds true for T0 maize plants expressing FLP202. More than 30% of the total tested events (n=89) showed also a good to high tolerance with 15% or less bleached leaf area after treatment with a 100 g AI/ha herbicide and ~13% show less than 5% or no visual leaf damage.

TABLE 14

Evaluation of leaf area damage from transgenic maize T0 events six days after the application of 2-chloro-3-(methylsulfanyl)-N-(1-methyl-1H-tetrazol-5-yl)-4-(trifluoromethyl)benzamide (Cmpd. 4); at a rate of 100 g AI/ha. The transgenic maize plants expressing the variants FLP202 or FLP136 of the *Pseudomonas fluorescens* HPPD protein have been obtained as described in Example 4. Following herbicide tolerance classes have been defined: "0" = marginal tolerance; 41%-100% damaged leaf area; "1" = moderate tolerance; 16%-41% damaged leaf area; "2" = good tolerance; 6%-15% damaged leaf area; "3" = high tolerance; 0%-5% damaged leaf area.

| Maize Events with | Herbicide tolerance classes | | | | Total number |
|---|---|---|---|---|---|
| HPPD variant | 0 | 1 | 2 | 3 | events |
| FLP136 | 13 | 37 | 21 | 13 | 84 |
| FLP202 | 12 | 49 | 16 | 12 | 89 |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A recombinant nucleic acid molecule encoding a 4-hydroxyphenylpyruvate dioxygenase (HPPD) protein consisting of an amino acid sequence having at least 95% sequence identity to SEQ ID NO:1, wherein said amino acid sequence comprises a substitution of a proline at the amino acid position corresponding to amino acid position 335 of SEQ ID NO:1 and a phenylalanine at the position corresponding to amino acid position 336 of SEQ ID NO:1, and wherein said HPPD protein is tolerant to an HPPD inhibitor herbicide.

2. The recombinant nucleic acid molecule of claim 1, wherein said encoded HPPD protein further comprises a substitution of a glutamic acid at the amino acid position corresponding to amino acid position 340 of SEQ ID NO:1.

3. The recombinant nucleic acid molecule of claim 2, wherein said encoded HPPD protein further comprises a substitution of leucine at the amino acid position corresponding to amino acid position 215 of SEQ ID NO:1.

4. The recombinant nucleic acid molecule of claim 1, wherein its nucleotide sequence is a synthetic sequence that has been designed for expression in a plant.

5. The recombinant nucleic acid molecule of claim 1, wherein its nucleotide sequence is operably linked to a promoter capable of directing expression of the nucleotide sequence in a plant cell.

6. The recombinant nucleic acid molecule of claim 1, wherein said HPPD inhibitor herbicide is a triketone herbicide.

7. The recombinant nucleic acid molecule of claim 6, wherein said HPPD inhibitor herbicide is mesotrione.

8. A host cell that contains the recombinant nucleic acid molecule of claim 1.

9. The host cell of claim 8 that is a bacterial host cell.

10. The host cell of claim 8 that is a plant cell.

11. A transgenic plant comprising the recombinant nucleic acid molecule of claim 1.

12. The plant of claim 11, wherein said plant is selected from the group consisting of maize, sorghum, wheat, sunflower, tomato, crucifers, peppers, potato, cotton, rice, soybean, sugar beet, sugarcane, tobacco, barley, and oilseed rape.

13. A transgenic seed comprising the recombinant nucleic acid molecule of claim 1.

14. A recombinant polypeptide comprising an HPPD protein, wherein said HPPD protein is tolerant to an HPPD inhibitor herbicide, and wherein said HPPD protein has at least 95% sequence identity to SEQ ID NO:1 and comprises a proline at the amino acid position corresponding to amino acid position 335 of SEQ ID NO:1 and a phenylalanine at the position corresponding to amino acid position 336 of SEQ ID NO:1.

15. The recombinant polypeptide of claim 14, wherein said HPPD protein further comprises a glutamic acid at the amino acid position corresponding to amino acid position 340 of SEQ ID NO:1.

16. The recombinant polypeptide of claim 14, wherein said HPPD protein further comprises a leucine at the amino acid position corresponding to amino acid position 215 of SEQ ID NO:1.

17. The recombinant polypeptide of claim 14, wherein said HPPD inhibitor herbicide is a triketone herbicide.

18. The recombinant polypeptide of claim 17, wherein said HPPD inhibitor herbicide is mesotrione.

19. A plant or a plant cell having stably incorporated into its genome a DNA construct, said construct comprising a promoter operably linked with the nucleic acid molecule of claim 1.

20. The plant or plant cell of claim 19, wherein said plant or plant cell is selected from the group consisting of maize, sorghum, wheat, sunflower, tomato, crucifers, peppers, potato, cotton, rice, soybean, sugar beet, sugarcane, tobacco, barley, and oilseed rape.

* * * * *

SEQUENCE LISTING

```
<160> NUMBER OF SEQ ID NOS: 46

<210> SEQ ID NO 1
<211> LENGTH: 358
<212> TYPE: PRT
<213> ORGANISM: Pseudomonas Fluorescens

<400> SEQUENCE: 1

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Thr Ala Asp
        355
```

<210> SEQ ID NO 2
<211> LENGTH: 358
<212> TYPE: PRT
<213> ORGANISM: Artificial Sequence
<220> FEATURE:
<223> OTHER INFORMATION: HPPD variant - Pf336F

<400> SEQUENCE: 2

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Phe
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 3
<211> LENGTH: 358
<212> TYPE: PRT
<213> ORGANISM: Artificial Sequence
<220> FEATURE:
<223> OTHER INFORMATION: HPPD variant - Pf336Y

<400> SEQUENCE: 3

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Tyr
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 4
<211> LENGTH: 358
<212> TYPE: PRT
<213> ORGANISM: Artificial Sequence
<220> FEATURE:
<223> OTHER INFORMATION: HPPD variant - Pf336W

<400> SEQUENCE: 4

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 5
<211> LENGTH: 358
<212> TYPE: PRT
<213> ORGANISM: Artificial Sequence
<220> FEATURE:
<223> OTHER INFORMATION: HPPD variant - C959

<400> SEQUENCE: 5

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Gly
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 6
<211> LENGTH: 358
<212> TYPE: PRT
<213> ORGANISM: Artificial Sequence
<220> FEATURE:
<223> OTHER INFORMATION: HPPD variant - PfEvo33

<400> SEQUENCE: 6

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

-continued

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Lys Ala Leu Phe Glu Ser Ile Glu Arg Asp Gln Val Arg Arg
            340                 345                 350

Gly Val Leu Thr Ala Asp
            355

<210> SEQ ID NO 7
<211> LENGTH: 358
<212> TYPE: PRT
<213> ORGANISM: Artificial Sequence
<220> FEATURE:
<223> OTHER INFORMATION: HPPD variant - PfEvo43

<400> SEQUENCE: 7

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 8
<211> LENGTH: 358
<212> TYPE: PRT
<213> ORGANISM: Artificial Sequence
<220> FEATURE:
<223> OTHER INFORMATION: HPPD variant - PfEvo44

<400> SEQUENCE: 8

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80
```

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Tyr
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 9
<211> LENGTH: 358
<212> TYPE: PRT
<213> ORGANISM: Artificial Sequence
<220> FEATURE:
<223> OTHER INFORMATION: HPPD variant - FLP129

<400> SEQUENCE: 9

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Ala Gln Leu Phe Glu Ser Ile Glu Arg Asp Gln Val Arg Arg
            340                 345                 350

Gly Val Leu Thr Ala Asp
        355

<210> SEQ ID NO 10
<211> LENGTH: 358
<212> TYPE: PRT
<213> ORGANISM: Artificial Sequence
<220> FEATURE:
<223> OTHER INFORMATION: HPPD variant - FLP130

<400> SEQUENCE: 10

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 11
<211> LENGTH: 358
<212> TYPE: PRT
<213> ORGANISM: Artificial Sequence
<220> FEATURE:
<223> OTHER INFORMATION: HPPD variant - FLP136

<400> SEQUENCE: 11

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Leu Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 12
<211> LENGTH: 358
<212> TYPE: PRT
<213> ORGANISM: Artificial Sequence
<220> FEATURE:
<223> OTHER INFORMATION: HPPD variant - FLP202

<400> SEQUENCE: 12

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Leu Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 13
<211> LENGTH: 358
<212> TYPE: PRT
<213> ORGANISM: Artificial Sequence
<220> FEATURE:
<223> OTHER INFORMATION: HPPD variant - K131

<400> SEQUENCE: 13

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Tyr
                325                 330                 335

Asn Phe Ala Gln Leu Phe Glu Ser Ile Glu Arg Asp Gln Val Arg Arg
            340                 345                 350

Gly Val Leu Thr Ala Asp
        355

<210> SEQ ID NO 14
<211> LENGTH: 358
<212> TYPE: PRT
<213> ORGANISM: Artificial Sequence
<220> FEATURE:
<223> OTHER INFORMATION: HPPD variant - K132

<400> SEQUENCE: 14

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
            115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Tyr
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 15
<211> LENGTH: 358
<212> TYPE: PRT
<213> ORGANISM: Artificial Sequence
<220> FEATURE:
<223> OTHER INFORMATION: HPPD variant - K137

<400> SEQUENCE: 15

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Leu Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Tyr
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 16
<211> LENGTH: 358
<212> TYPE: PRT
<213> ORGANISM: Artificial Sequence
<220> FEATURE:
<223> OTHER INFORMATION: HPPD variant - K203

<400> SEQUENCE: 16

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80
```

Met Ala Phe Arg Val Lys Asp Ser Gln Lys Ala Tyr Asn Arg Ala Leu
            85                  90                  95

Glu Leu Gly Ala Gln Pro Ile His Ile Asp Thr Gly Pro Met Glu Leu
        100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Leu Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Tyr
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 17
<211> LENGTH: 358
<212> TYPE: PRT
<213> ORGANISM: Artificial Sequence
<220> FEATURE:
<223> OTHER INFORMATION: HPPD variant - K250

<400> SEQUENCE: 17

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Cys Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Leu Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355
```

<210> SEQ ID NO 18
<211> LENGTH: 358
<212> TYPE: PRT
<213> ORGANISM: Artificial Sequence
<220> FEATURE:
<223> OTHER INFORMATION: HPPD variant - K255

<400> SEQUENCE: 18

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Ala Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 19
<211> LENGTH: 358
<212> TYPE: PRT
<213> ORGANISM: Artificial Sequence
<220> FEATURE:
<223> OTHER INFORMATION: HPPD variant - K258

<400> SEQUENCE: 19

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Asn Leu Asn Glu Glu Ser Ser Lys Gly Ala
        210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 20
<211> LENGTH: 358
<212> TYPE: PRT
<213> ORGANISM: Artificial Sequence
<220> FEATURE:
<223> OTHER INFORMATION: HPPD variant - K299

<400> SEQUENCE: 20

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
            115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Leu Leu Asn Glu Glu Ser Ser Lys Gly Ala
        210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Thr Ala Asp
        355

<210> SEQ ID NO 21
<211> LENGTH: 358
<212> TYPE: PRT
<213> ORGANISM: Artificial Sequence
<220> FEATURE:
<223> OTHER INFORMATION: HPPD variant - K300

<400> SEQUENCE: 21

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Leu Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Gly Leu Phe Glu Ser Ile Glu Arg Asp Gln Val Arg Arg
            340                 345                 350

Gly Val Leu Thr Ala Asp
        355

<210> SEQ ID NO 22
<211> LENGTH: 358
<212> TYPE: PRT
<213> ORGANISM: Artificial Sequence
<220> FEATURE:
<223> OTHER INFORMATION: HPPD variant - K303

<400> SEQUENCE: 22

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                 85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
            115                 120                 125

Asp Arg Phe Gly Glu Gly Ser Ser Ile Tyr Asp Ile Asp Phe Val Tyr
            130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Ile Thr Ser Lys Ala Met Ser Ala Pro
            195                 200                 205

Asp Gly Met Ile Arg Ile Leu Leu Asn Glu Glu Ser Ser Lys Gly Ala
            210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
            290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
            355

<210> SEQ ID NO 23
<211> LENGTH: 358
<212> TYPE: PRT
<213> ORGANISM: Artificial Sequence
<220> FEATURE:
<223> OTHER INFORMATION: HPPD variant - K304

<400> SEQUENCE: 23

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Met Thr Ser Lys Ala Met Ser Ala Pro
        195                 200                 205

Asp Gly Met Ile Arg Ile Leu Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 24
<211> LENGTH: 358
<212> TYPE: PRT
<213> ORGANISM: Artificial Sequence
<220> FEATURE:
<223> OTHER INFORMATION: HPPD variant - K306

<400> SEQUENCE: 24

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65              70                  75                  80
```

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Leu Leu Asn Glu Glu Ser Ser Lys Gly Ala
    210                 215                 220

Gly His Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 25
<211> LENGTH: 358
<212> TYPE: PRT
<213> ORGANISM: Artificial Sequence
<220> FEATURE:
<223> OTHER INFORMATION: HPPD variant - K325

<400> SEQUENCE: 25

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Cys Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Asn Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 26
<211> LENGTH: 358
<212> TYPE: PRT
<213> ORGANISM: Artificial Sequence
<220> FEATURE:
<223> OTHER INFORMATION: HPPD variant - K357

<400> SEQUENCE: 26

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80
```

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Cys Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 27
<211> LENGTH: 358
<212> TYPE: PRT
<213> ORGANISM: Artificial Sequence
<220> FEATURE:
<223> OTHER INFORMATION: HPPD variant - K360

<400> SEQUENCE: 27

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Ile Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 28
<211> LENGTH: 358
<212> TYPE: PRT
<213> ORGANISM: Artificial Sequence
<220> FEATURE:
<223> OTHER INFORMATION: HPPD variant - K361

<400> SEQUENCE: 28

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
            115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Met Thr Ser Lys Ala Met Ser Ala Pro
            195                 200                 205

Asp Gly Met Ile Arg Ile Pro Leu Asn Glu Glu Ser Ser Lys Gly Ala
        210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
            275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 29
<211> LENGTH: 358
<212> TYPE: PRT
<213> ORGANISM: Artificial Sequence
<220> FEATURE:
<223> OTHER INFORMATION: HPPD variant - K363

<400> SEQUENCE: 29

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly His Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 30
<211> LENGTH: 358
<212> TYPE: PRT
<213> ORGANISM: Artificial Sequence
<220> FEATURE:
<223> OTHER INFORMATION: HPPD variant - K405

<400> SEQUENCE: 30

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
            100                 105                 110
Asn Leu Pro Ala Ile Lys Gly Ile Gly Ala Pro Leu Tyr Leu Ile
        115                 120                 125
Asp Arg Phe Gly Glu Gly Ser Ser Ile Tyr Asp Ile Asp Phe Val Tyr
        130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Gly Cys Tyr Phe Asp
                180                 185                 190
Ile Lys Gly Glu Tyr Thr Gly Leu Thr Ser Lys Ala Met Ser Ala Pro
            195                 200                 205
Asp Gly Met Ile Arg Ile Ala Leu Asn Glu Glu Ser Ser Lys Gly Ala
        210                 215                 220
Gly Gln Ile Glu Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
                260                 265                 270
Glu Met Leu Glu Gly Arg Leu Pro Asp His Gly Glu Pro Val Asp Gln
            275                 280                 285
Leu Gln Ala Arg Gly Ile Leu Leu Asp Gly Ser Ser Val Glu Gly Asp
        290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Pro Phe
                325                 330                 335
Asn Phe Lys Glu Leu Phe Glu Ser Ile Glu Arg Asp Gln Val Arg Arg
                340                 345                 350
Gly Val Leu Thr Ala Asp
        355

<210> SEQ ID NO 31
<211> LENGTH: 358
<212> TYPE: PRT
<213> ORGANISM: Artificial Sequence
<220> FEATURE:
<223> OTHER INFORMATION: HPPD variant - K406

<400> SEQUENCE: 31

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
                20                  25                  30
Ile Met Gly Phe Thr Lys Val Ala Thr His Arg Ser Lys Asn Val His
            35                  40                  45
Leu Tyr Arg Gln Gly Glu Ile Asn Leu Ile Leu Asn Asn Glu Pro Asn
        50                  55                  60
Ser Ile Ala Ser Tyr Phe Ala Ala Glu His Gly Pro Ser Val Cys Gly
65                  70                  75                  80
```

-continued

```
Met Ala Phe Arg Val Lys Asp Ser Gln Lys Ala Tyr Asn Arg Ala Leu
                85                  90                  95
Glu Leu Gly Ala Gln Pro Ile His Ile Asp Thr Gly Pro Met Glu Leu
            100                 105                 110
Asn Leu Pro Ala Ile Lys Gly Ile Gly Ala Pro Leu Tyr Leu Ile
        115                 120                 125
Asp Arg Phe Gly Glu Gly Ser Ser Ile Tyr Asp Ile Asp Phe Val Tyr
    130                 135                 140
Leu Glu Gly Val Glu Arg Asn Pro Val Gly Ala Gly Leu Lys Val Ile
145                 150                 155                 160
Asp His Leu Thr His Asn Val Tyr Arg Gly Arg Met Val Tyr Trp Ala
                165                 170                 175
Asn Phe Tyr Glu Lys Leu Phe Asn Phe Arg Glu Gly Gly Tyr Phe Asp
                180                 185                 190
Ile Lys Gly Glu Tyr Thr Gly Leu Thr Ser Lys Ala Met Ser Ala Pro
            195                 200                 205
Asp Gly Met Ile Arg Ile Asn Leu Asn Glu Glu Ser Ser Lys Gly Ala
        210                 215                 220
Gly Gln Ile Glu Glu Phe Leu Met Gln Phe Asn Gly Glu Gly Ile Gln
225                 230                 235                 240
His Val Ala Phe Leu Thr Asp Asp Leu Val Lys Thr Trp Asp Ala Leu
                245                 250                 255
Lys Lys Ile Gly Met Arg Phe Met Thr Ala Pro Pro Asp Thr Tyr Tyr
                260                 265                 270
Glu Met Leu Glu Gly Arg Leu Pro Asp His Gly Glu Pro Val Asp Gln
            275                 280                 285
Leu Gln Ala Arg Gly Ile Leu Leu Asp Gly Ser Ser Val Glu Gly Asp
        290                 295                 300
Lys Arg Leu Leu Leu Gln Ile Phe Ser Glu Thr Leu Met Gly Pro Val
305                 310                 315                 320
Phe Phe Glu Phe Ile Gln Arg Lys Gly Asp Asp Gly Phe Gly Pro Phe
                325                 330                 335
Asn Phe Lys Glu Leu Phe Glu Ser Ile Glu Arg Asp Gln Val Arg Arg
                340                 345                 350
Gly Val Leu Thr Ala Asp
            355

<210> SEQ ID NO 32
<211> LENGTH: 358
<212> TYPE: PRT
<213> ORGANISM: Artificial Sequence
<220> FEATURE:
<223> OTHER INFORMATION: HPPD variant - K407

<400> SEQUENCE: 32

Met Ala Asp Leu Tyr Glu Asn Pro Met Gly Leu Met Gly Phe Glu Phe
1               5                   10                  15
Ile Glu Phe Ala Ser Pro Thr Pro Gly Thr Leu Glu Pro Ile Phe Glu
            20                  25                  30
Ile Met Gly Phe Thr Lys Val Ala Thr His Arg Ser Lys Asn Val His
        35                  40                  45
Leu Tyr Arg Gln Gly Glu Ile Asn Leu Ile Leu Asn Asn Glu Pro Asn
    50                  55                  60
Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Glu Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Asn Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 33
<211> LENGTH: 358
<212> TYPE: PRT
<213> ORGANISM: Artificial Sequence
<220> FEATURE:
<223> OTHER INFORMATION: HPPD variant - K408

<400> SEQUENCE: 33

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Gly Asp Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Asn Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Phe
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 34
<211> LENGTH: 358
<212> TYPE: PRT
<213> ORGANISM: Artificial Sequence
<220> FEATURE:
<223> OTHER INFORMATION: HPPD variant - PfEvo36

<400> SEQUENCE: 34

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80

Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Ser Ser
                325                 330                 335

Asn Phe Thr Gln Leu Phe Glu Ser Ile Glu Arg Asp Gln Val Arg Arg
            340                 345                 350

Gly Val Leu Thr Ala Asp
        355

<210> SEQ ID NO 35
<211> LENGTH: 358
<212> TYPE: PRT
<213> ORGANISM: Artificial Sequence
<220> FEATURE:
<223> OTHER INFORMATION: HPPD variant - PfEvo37

<400> SEQUENCE: 35

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
                20                  25                  30

Ile Met Gly Phe Thr Lys Val Ala Thr His Arg Ser Lys Asn Val His
            35                  40                  45

Leu Tyr Arg Gln Gly Glu Ile Asn Leu Ile Leu Asn Asn Glu Pro Asn
        50                  55                  60

Ser Ile Ala Ser Tyr Phe Ala Ala Glu His Gly Pro Ser Val Cys Gly
65                  70                  75                  80

-continued

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Trp Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Trp
                325                 330                 335

Asn Phe Lys Ala Leu Phe Glu Ser Ile Glu Arg Asp Gln Val Arg Arg
            340                 345                 350

Gly Val Leu Thr Ala Asp
        355
```

<210> SEQ ID NO 36
<211> LENGTH: 358
<212> TYPE: PRT
<213> ORGANISM: Artificial Sequence
<220> FEATURE:
<223> OTHER INFORMATION: HPPD variant - PfEvo40

<400> SEQUENCE: 36

```
Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Ser
                325                 330                 335

Asn Phe Lys Glu Leu Phe Glu Ser Ile Glu Arg Asp Gln Val Arg Arg
            340                 345                 350

Gly Val Leu Thr Ala Asp
        355

<210> SEQ ID NO 37
<211> LENGTH: 358
<212> TYPE: PRT
<213> ORGANISM: Artificial Sequence
<220> FEATURE:
<223> OTHER INFORMATION: HPPD variant - PfEvo41

<400> SEQUENCE: 37

Met Ala Asp Leu Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Glu Pro Asn
    50                  55                  60

Ser Ile Ala Ser Tyr Phe Ala Ala Glu His Gly Pro Ser Val Cys Gly
65                  70                  75                  80
```

```
Met Ala Phe Arg Val Lys Asp Ser Gln Lys Ala Tyr Asn Arg Ala Leu
                 85                  90                  95

Glu Leu Gly Ala Gln Pro Ile His Ile Asp Thr Gly Pro Met Glu Leu
            100                 105                 110

Asn Leu Pro Ala Ile Lys Gly Ile Gly Gly Ala Pro Leu Tyr Leu Ile
            115                 120                 125

Asp Arg Phe Gly Glu Gly Ser Ser Ile Tyr Asp Ile Asp Phe Val Tyr
        130                 135                 140

Leu Glu Gly Val Glu Arg Asn Pro Val Gly Ala Gly Leu Lys Val Ile
145                 150                 155                 160

Asp His Leu Thr His Asn Val Tyr Arg Gly Arg Met Val Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
        210                 215                 220

Gly Gln Ile Glu Glu Phe Leu Met Gln Phe Asn Gly Glu Gly Ile Gln
225                 230                 235                 240

His Val Ala Phe Leu Thr Asp Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asp His Gly Glu Pro Val Asp Gln
        275                 280                 285

Leu Gln Ala Arg Gly Ile Leu Leu Asp Gly Ser Ser Val Glu Gly Asp
        290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Pro Trp
                325                 330                 335

Asn Phe Ala Gln Leu Phe Glu Ser Ile Glu Arg Asp Gln Val Arg Arg
            340                 345                 350

Gly Val Leu Thr Ala Asp
            355

<210> SEQ ID NO 38
<211> LENGTH: 440
<212> TYPE: PRT
<213> ORGANISM: Avena sativa

<400> SEQUENCE: 38

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
```

```
                    85                  90                  95
Ala Pro Tyr Ala Pro Pro Gln Glu Ala Thr Ala Ala Thr
            100                 105                 110
Ala Ser Ile Pro Ser Phe Ser Ala Asp Ala Arg Thr Phe Ala Ala
            115                 120                 125
Ala His Gly Leu Ala Val Arg Ser Val Gly Val Arg Val Ala Asp Ala
130                 135                 140
Ala Glu Ala Phe Arg Val Ser Val Ala Gly Ala Arg Pro Ala Phe
145                 150                 155                 160
Ala Pro Ala Asp Leu Gly His Gly Phe Gly Leu Ala Glu Val Glu Leu
                165                 170                 175
Tyr Gly Asp Val Val Leu Arg Phe Val Ser Tyr Pro Asp Glu Thr Asp
                180                 185                 190
Leu Pro Phe Leu Pro Gly Phe Glu Arg Val Ser Ser Pro Gly Ala Val
                195                 200                 205
Asp Tyr Gly Leu Thr Arg Phe Asp His Val Val Gly Asn Val Pro Glu
                210                 215                 220
Met Ala Pro Val Ile Asp Tyr Met Lys Gly Phe Leu Gly Phe His Glu
225                 230                 235                 240
Phe Ala Glu Phe Thr Ala Glu Asp Val Gly Thr Thr Glu Ser Gly Leu
                245                 250                 255
Asn Ser Val Val Leu Ala Asn Asn Ser Glu Ala Val Leu Leu Pro Leu
                260                 265                 270
Asn Glu Pro Val His Gly Thr Lys Arg Arg Ser Gln Ile Gln Thr Tyr
                275                 280                 285
Leu Glu Tyr His Gly Gly Pro Gly Val Gln His Ile Ala Leu Ala Ser
                290                 295                 300
Asn Asp Val Leu Arg Thr Leu Arg Glu Met Arg Ala Arg Thr Pro Met
305                 310                 315                 320
Gly Gly Phe Glu Phe Met Ala Pro Pro Gln Ala Lys Tyr Tyr Glu Gly
                325                 330                 335
Val Arg Arg Ile Ala Gly Asp Val Leu Ser Glu Glu Gln Ile Lys Glu
                340                 345                 350
Cys Gln Glu Leu Gly Val Leu Val Asp Arg Asp Asp Gln Gly Val Leu
                355                 360                 365
Leu Gln Ile Phe Thr Lys Pro Val Gly Asp Arg Pro Thr Phe Phe Leu
                370                 375                 380
Glu Met Ile Gln Arg Ile Gly Cys Met Glu Lys Asp Glu Val Gly Gln
385                 390                 395                 400
Glu Tyr Gln Lys Gly Gly Cys Gly Gly Phe Gly Lys Gly Asn Phe Ser
                405                 410                 415
Glu Leu Phe Lys Ser Ile Glu Asp Tyr Glu Lys Ser Leu Glu Val Lys
                420                 425                 430
Gln Ser Val Val Ala Gln Lys Ser
                435                 440

<210> SEQ ID NO 39
<211> LENGTH: 439
<212> TYPE: PRT
<213> ORGANISM: Artificial Sequence
<220> FEATURE:
<223> OTHER INFORMATION: HPPD variant - Avena sativa(del)

<400> SEQUENCE: 39

Met Pro Pro Thr Pro Ala Thr Ala Thr Gly Ala Ala Ala Ala Ala Val
```

-continued

```
1               5                   10                  15
Thr Pro Glu His Ala Arg Ser Phe Pro Arg Val Val Arg Val Asn
                20                  25                  30
Pro Arg Ser Asp Arg Phe Pro Val Leu Ser Phe His His Val Glu Leu
                35                  40                  45
Trp Cys Ala Asp Ala Ala Ser Ala Ala Gly Arg Phe Ser Phe Ala Leu
                50                  55                  60
Gly Ala Pro Leu Ala Ala Arg Ser Asp Leu Ser Thr Gly Asn Ser Ala
65                  70                  75                  80
His Ala Ser Leu Leu Leu Arg Ser Gly Ala Leu Ala Phe Leu Phe Thr
                85                  90                  95
Ala Pro Tyr Ala Pro Pro Gln Glu Ala Thr Ala Ala Thr Ala
                100                 105                 110
Ser Ile Pro Ser Phe Ser Ala Asp Ala Ala Arg Thr Phe Ala Ala Ala
                115                 120                 125
His Gly Leu Ala Val Arg Ser Val Gly Val Arg Val Ala Asp Ala Ala
                130                 135                 140
Glu Ala Phe Arg Val Ser Val Ala Gly Gly Ala Arg Pro Ala Phe Ala
145                 150                 155                 160
Pro Ala Asp Leu Gly His Gly Phe Gly Leu Ala Glu Val Glu Leu Tyr
                165                 170                 175
Gly Asp Val Val Leu Arg Phe Val Ser Tyr Pro Asp Glu Thr Asp Leu
                180                 185                 190
Pro Phe Leu Pro Gly Phe Glu Arg Val Ser Ser Pro Gly Ala Val Asp
                195                 200                 205
Tyr Gly Leu Thr Arg Phe Asp His Val Val Gly Asn Val Pro Glu Met
                210                 215                 220
Ala Pro Val Ile Asp Tyr Met Lys Gly Phe Leu Gly Phe His Glu Phe
225                 230                 235                 240
Ala Glu Phe Thr Ala Glu Asp Val Gly Thr Thr Glu Ser Gly Leu Asn
                245                 250                 255
Ser Val Val Leu Ala Asn Asn Ser Glu Ala Val Leu Leu Pro Leu Asn
                260                 265                 270
Glu Pro Val His Gly Thr Lys Arg Ser Gln Ile Gln Thr Tyr Leu
                275                 280                 285
Glu Tyr His Gly Gly Pro Gly Val Gln His Ile Ala Leu Ala Ser Asn
                290                 295                 300
Asp Val Leu Arg Thr Leu Arg Glu Met Arg Ala Arg Thr Pro Met Gly
305                 310                 315                 320
Gly Phe Glu Phe Met Ala Pro Pro Gln Ala Lys Tyr Tyr Glu Gly Val
                325                 330                 335
Arg Arg Ile Ala Gly Asp Val Leu Ser Glu Glu Ile Lys Glu Cys
                340                 345                 350
Gln Glu Leu Gly Val Leu Val Asp Arg Asp Asp Gln Gly Val Leu Leu
                355                 360                 365
Gln Ile Phe Thr Lys Pro Val Gly Asp Arg Pro Thr Phe Phe Leu Glu
                370                 375                 380
Met Ile Gln Arg Ile Gly Cys Met Glu Lys Asp Glu Val Gly Gln Glu
385                 390                 395                 400
Tyr Gln Lys Gly Gly Cys Gly Gly Phe Gly Lys Gly Asn Phe Ser Glu
                405                 410                 415
Leu Phe Lys Ser Ile Glu Asp Tyr Glu Lys Ser Leu Glu Val Lys Gln
                420                 425                 430
```

Ser Val Val Ala Gln Lys Ser
        435

<210> SEQ ID NO 40
<211> LENGTH: 444
<212> TYPE: PRT
<213> ORGANISM: Zea mays

<400> SEQUENCE: 40

Met Gly Pro Thr Pro Thr Ala Ala Ala Gly Ala Ala Val Ala Ala
1               5                   10                  15

Ala Ser Ala Ala Glu Gln Ala Ala Phe Arg Leu Val Gly His Arg Asn
            20                  25                  30

Phe Val Arg Phe Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Ser Ala His Ala Ser Leu Leu Arg Ser Gly Ser Leu
                85                  90                  95

Ser Phe Leu Phe Thr Ala Pro Tyr Ala His Gly Ala Asp Ala Ala Thr
            100                 105                 110

Ala Ala Leu Pro Ser Phe Ser Ala Ala Ala Arg Arg Phe Ala Ala
        115                 120                 125

Asp His Gly Leu Ala Val Arg Ala Val Ala Leu Arg Val Ala Asp Ala
130                 135                 140

Glu Asp Ala Phe Arg Ala Ser Val Ala Ala Gly Ala Arg Pro Ala Phe
145                 150                 155                 160

Gly Pro Val Asp Leu Gly Arg Gly Phe Arg Leu Ala Glu Val Glu Leu
                165                 170                 175

Tyr Gly Asp Val Val Leu Arg Tyr Val Ser Tyr Pro Asp Gly Ala Ala
            180                 185                 190

Gly Glu Pro Phe Leu Pro Gly Phe Glu Gly Val Ala Ser Pro Gly Ala
        195                 200                 205

Ala Asp Tyr Gly Leu Ser Arg Phe Asp His Ile Val Gly Asn Val Pro
    210                 215                 220

Glu Leu Ala Pro Ala Ala Tyr Phe Ala Gly Phe Thr Gly Phe His
225                 230                 235                 240

Glu Phe Ala Glu Phe Thr Thr Glu Asp Val Gly Thr Ala Glu Ser Gly
                245                 250                 255

Leu Asn Ser Met Val Leu Ala Asn Asn Ser Glu Asn Val Leu Leu Pro
            260                 265                 270

Leu Asn Glu Pro Val His Gly Thr Lys Arg Arg Ser Gln Ile Gln Thr
        275                 280                 285

Phe Leu Asp His His Gly Gly Pro Gly Val Gln His Met Ala Leu Ala
    290                 295                 300

Ser Asp Asp Val Leu Arg Thr Leu Arg Glu Met Gln Ala Arg Ser Ala
305                 310                 315                 320

Met Gly Gly Phe Glu Phe Met Ala Pro Pro Thr Ser Asp Tyr Tyr Asp
                325                 330                 335

Gly Val Arg Arg Arg Ala Gly Asp Val Leu Thr Glu Ala Gln Ile Lys
            340                 345                 350

Glu Cys Gln Glu Leu Gly Val Leu Val Asp Arg Asp Asp Gln Gly Val

-continued

```
           355                 360                 365
Leu Leu Gln Ile Phe Thr Lys Pro Val Gly Asp Arg Pro Thr Leu Phe
    370                 375                 380

Leu Glu Ile Ile Gln Arg Ile Gly Cys Met Glu Lys Asp Glu Lys Gly
385                 390                 395                 400

Gln Glu Tyr Gln Lys Gly Gly Cys Gly Gly Phe Gly Lys Gly Asn Phe
                405                 410                 415

Ser Gln Leu Phe Lys Ser Ile Glu Asp Tyr Glu Lys Ser Leu Glu Ala
                420                 425                 430

Lys Gln Ala Ala Ala Ala Ala Ala Gln Gly Ser
            435                 440

<210> SEQ ID NO 41
<211> LENGTH: 445
<212> TYPE: PRT
<213> ORGANISM: Arabidopsis thaliana

<400> SEQUENCE: 41

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
                20                  25                  30

Val Arg Lys Asn Pro Lys Ser Asp Lys Phe Lys Val Lys Arg Phe His
            35                  40                  45

His Ile Glu Phe Trp Cys Gly Asp Ala Thr Asn Val Ala Arg Arg Phe
        50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
                100                 105                 110

Lys Pro Thr Thr Thr Ala Ser Ile Pro Ser Phe Asp His Gly Ser Cys
            115                 120                 125

Arg Ser Phe Phe Ser Ser His Gly Leu Gly Val Arg Ala Val Ala Ile
        130                 135                 140

Glu Val Glu Asp Ala Glu Ser Ala Phe Ser Ile Ser Val Ala Asn Gly
145                 150                 155                 160

Ala Ile Pro Ser Ser Pro Ile Val Leu Asn Glu Ala Val Thr Ile
                165                 170                 175

Ala Glu Val Lys Leu Tyr Gly Asp Val Val Leu Arg Tyr Val Ser Tyr
                180                 185                 190

Lys Ala Glu Asp Thr Glu Lys Ser Glu Phe Leu Pro Gly Phe Glu Arg
            195                 200                 205

Val Glu Asp Ala Ser Ser Phe Pro Leu Asp Tyr Gly Ile Arg Arg Leu
        210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255

Asp Val Gly Thr Ala Glu Ser Gly Leu Asn Ser Ala Val Leu Ala Ser
                260                 265                 270

Asn Asp Glu Met Val Leu Leu Pro Ile Asn Glu Pro Val His Gly Thr
            275                 280                 285
```

```
Lys Arg Lys Ser Gln Ile Gln Thr Tyr Leu Glu His Asn Glu Gly Ala
    290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Thr Tyr Tyr Gln Asn Leu Lys Lys Arg Val Gly Asp
            340                 345                 350

Val Leu Ser Asp Asp Gln Ile Lys Glu Cys Glu Leu Gly Ile Leu
        355                 360                 365

Val Asp Arg Asp Asp Gln Gly Thr Leu Leu Gln Ile Phe Thr Lys Pro
370                 375                 380

Leu Gly Asp Arg Pro Thr Ile Phe Ile Glu Ile Ile Gln Arg Val Gly
385                 390                 395                 400

Cys Met Met Lys Asp Glu Gly Lys Ala Tyr Gln Ser Gly Cys
                405                 410                 415

Gly Gly Phe Gly Lys Gly Asn Phe Ser Glu Leu Phe Lys Ser Ile Glu
            420                 425                 430

Glu Tyr Glu Lys Thr Leu Glu Ala Lys Gln Leu Val Gly
        435                 440                 445

<210> SEQ ID NO 42
<211> LENGTH: 434
<212> TYPE: PRT
<213> ORGANISM: Hordeum vulgare

<400> SEQUENCE: 42

Met Pro Pro Thr Pro Thr Thr Pro Ala Ala Thr Gly Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His His Val Glu Phe Trp
        35                  40                  45

Cys Ala Asp Ala Ala Ser Ala Ala Gly Arg Phe Ala Phe Ala Leu Gly
    50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Ala Thr Ala Ser Leu Pro Ser Phe
            100                 105                 110

Ser Ala Asp Ala Ala Arg Arg Phe Ser Ala Asp His Gly Ile Ala Val
        115                 120                 125

Arg Ser Val Ala Leu Arg Val Ala Asp Ala Ala Glu Ala Phe Arg Ala
    130                 135                 140

Ser Arg Arg Arg Gly Ala Arg Pro Ala Phe Ala Pro Val Asp Leu Gly
145                 150                 155                 160

Arg Gly Phe Ala Phe Ala Glu Val Glu Leu Tyr Gly Asp Val Val Leu
                165                 170                 175

Arg Phe Val Ser His Pro Asp Gly Thr Asp Val Pro Phe Leu Pro Gly
            180                 185                 190

Phe Glu Gly Val Thr Asn Pro Asp Ala Val Asp Tyr Gly Leu Thr Arg
        195                 200                 205

Phe Asp His Val Val Gly Asn Val Pro Glu Leu Ala Pro Ala Ala Ala
    210                 215                 220
```

```
Tyr Ile Ala Gly Phe Thr Gly Phe His Glu Phe Ala Glu Phe Thr Ala
225                 230                 235                 240

Glu Asp Val Gly Thr Thr Glu Ser Gly Leu Asn Ser Val Val Leu Ala
            245                 250                 255

Asn Asn Ser Glu Gly Val Leu Leu Pro Leu Asn Glu Pro Val His Gly
        260                 265                 270

Thr Lys Arg Arg Ser Gln Ile Gln Thr Phe Leu Glu His His Gly Gly
            275                 280                 285

Pro Gly Val Gln His Ile Ala Val Ala Ser Ser Asp Val Leu Arg Thr
        290                 295                 300

Leu Arg Lys Met Arg Ala Arg Ser Ala Met Gly Gly Phe Asp Phe Leu
305                 310                 315                 320

Pro Pro Pro Leu Pro Lys Tyr Tyr Glu Gly Val Arg Arg Leu Ala Gly
            325                 330                 335

Asp Val Leu Ser Glu Ala Gln Ile Lys Glu Cys Gln Glu Leu Gly Val
        340                 345                 350

Leu Val Asp Arg Asp Asp Gln Gly Val Leu Leu Gln Ile Phe Thr Lys
            355                 360                 365

Pro Val Gly Asp Arg Pro Thr Leu Phe Leu Glu Met Ile Gln Arg Ile
370                 375                 380

Gly Cys Met Glu Lys Asp Glu Arg Gly Glu Tyr Gln Lys Gly Gly
385                 390                 395                 400

Cys Gly Gly Phe Gly Lys Gly Asn Phe Ser Glu Leu Phe Lys Ser Ile
            405                 410                 415

Glu Asp Tyr Glu Lys Ser Leu Glu Ala Lys Gln Ser Ala Ala Val Gln
            420                 425                 430

Gly Ser

<210> SEQ ID NO 43
<211> LENGTH: 442
<212> TYPE: PRT
<213> ORGANISM: Daucus carota

<400> SEQUENCE: 43

Met Gly Lys Lys Gln Ser Glu Ala Glu Ile Leu Ser Ser Asn Ser Ser
1               5                   10                  15

Asn Thr Ser Pro Ala Thr Phe Lys Leu Val Gly Phe Asn Asn Phe Val
            20                  25                  30

Arg Ala Asn Pro Lys Ser Asp His Phe Ala Val Lys Arg Phe His His
        35                  40                  45

Ile Glu Phe Trp Cys Gly Asp Ala Thr Asn Thr Ser Arg Arg Phe Ser
50                  55                  60

Trp Gly Leu Gly Met Pro Leu Val Ala Lys Ser Asp Leu Ser Thr Gly
65                  70                  75                  80

Asn Ser Val His Ala Ser Tyr Leu Val Arg Ser Ala Asn Leu Ser Phe
                85                  90                  95

Val Phe Thr Ala Pro Tyr Ser Pro Ser Thr Thr Thr Ser Ser Gly Ser
            100                 105                 110

Ala Ala Ile Pro Ser Phe Ser Ala Ser Gly Phe His Ser Phe Ala Ala
        115                 120                 125

Lys His Gly Leu Ala Val Arg Ala Ile Ala Leu Glu Val Ala Asp Val
    130                 135                 140

Ala Ala Ala Phe Glu Ala Ser Val Ala Arg Gly Ala Arg Pro Ala Ser
145                 150                 155                 160
```

```
Ala Pro Val Glu Leu Asp Asp Gln Ala Trp Leu Ala Glu Val Glu Leu
            165                 170                 175

Tyr Gly Asp Val Val Leu Arg Phe Val Ser Phe Gly Arg Glu Glu Gly
                180                 185                 190

Leu Phe Leu Pro Gly Phe Glu Ala Val Glu Gly Thr Ala Ser Phe Pro
            195                 200                 205

Asp Leu Asp Tyr Gly Ile Arg Arg Leu Asp His Ala Val Gly Asn Val
            210                 215                 220

Thr Glu Leu Gly Pro Val Val Glu Tyr Ile Lys Gly Phe Thr Gly Phe
225                 230                 235                 240

His Glu Phe Ala Glu Phe Thr Ala Glu Asp Val Gly Thr Leu Glu Ser
            245                 250                 255

Gly Leu Asn Ser Val Val Leu Ala Asn Asn Glu Glu Met Val Leu Leu
            260                 265                 270

Pro Leu Asn Glu Pro Val Tyr Gly Thr Lys Arg Lys Ser Gln Ile Gln
            275                 280                 285

Thr Tyr Leu Glu His Asn Glu Gly Ala Gly Val Gln His Leu Ala Leu
            290                 295                 300

Val Ser Glu Asp Ile Phe Arg Thr Leu Arg Glu Met Arg Lys Arg Ser
305                 310                 315                 320

Cys Leu Gly Gly Phe Glu Phe Met Pro Ser Pro Pro Thr Tyr Tyr
            325                 330                 335

Lys Asn Leu Lys Asn Arg Val Gly Asp Val Leu Ser Asp Glu Gln Ile
            340                 345                 350

Lys Glu Cys Glu Asp Leu Gly Ile Leu Val Asp Arg Asp Asp Gln Gly
            355                 360                 365

Thr Leu Leu Gln Ile Phe Thr Lys Pro Val Gly Asp Arg Pro Thr Leu
            370                 375                 380

Phe Ile Glu Ile Ile Gln Arg Val Gly Cys Met Leu Lys Asp Asp Ala
385                 390                 395                 400

Gly Gln Met Tyr Gln Lys Gly Gly Cys Gly Gly Phe Gly Lys Gly Asn
            405                 410                 415

Phe Ser Glu Leu Phe Lys Ser Ile Glu Glu Tyr Glu Lys Thr Leu Glu
            420                 425                 430

Ala Lys Gln Ile Thr Gly Ser Ala Ala Ala
            435                 440

<210> SEQ ID NO 44
<211> LENGTH: 380
<212> TYPE: PRT
<213> ORGANISM: Streptomyces avermitilis

<400> SEQUENCE: 44

Met Thr Gln Thr Thr His His Thr Pro Asp Thr Ala Arg Gln Ala Asp
1               5                   10                  15

Pro Phe Pro Val Lys Gly Met Asp Ala Val Phe Ala Val Gly Asn
            20                  25                  30

Ala Lys Gln Ala Ala His Tyr Ser Thr Ala Phe Gly Met Gln Leu Val
            35                  40                  45

Ala Tyr Ser Gly Pro Glu Asn Gly Ser Arg Glu Thr Ala Ser Tyr Val
            50                  55                  60

Leu Thr Asn Gly Ser Ala Arg Phe Val Leu Thr Ser Val Ile Lys Pro
65                  70                  75                  80

Ala Thr Pro Trp Gly His Phe Leu Ala Asp His Val Ala Glu His Gly
```

```
                    85                  90                  95
Asp Gly Val Val Asp Leu Ala Ile Glu Val Pro Asp Ala Arg Ala Ala
            100                 105                 110

His Ala Tyr Ala Ile Glu His Gly Ala Arg Ser Val Ala Glu Pro Tyr
            115                 120                 125

Glu Leu Lys Asp Glu His Gly Thr Val Val Leu Ala Ala Ile Ala Thr
            130                 135                 140

Tyr Gly Lys Thr Arg His Thr Leu Val Asp Arg Thr Gly Tyr Asp Gly
145                 150                 155                 160

Pro Tyr Leu Pro Gly Tyr Val Ala Ala Pro Ile Val Glu Pro Pro
            165                 170                 175

Ala His Arg Thr Phe Gln Ala Ile Asp His Cys Val Gly Asn Val Glu
            180                 185                 190

Leu Gly Arg Met Asn Glu Trp Val Gly Phe Tyr Asn Lys Val Met Gly
            195                 200                 205

Phe Thr Asn Met Lys Glu Phe Val Gly Asp Asp Ile Ala Thr Glu Tyr
            210                 215                 220

Ser Ala Leu Met Ser Lys Val Val Ala Asp Gly Thr Leu Lys Val Lys
225                 230                 235                 240

Phe Pro Ile Asn Glu Pro Ala Leu Ala Lys Lys Ser Gln Ile Asp
            245                 250                 255

Glu Tyr Leu Glu Phe Tyr Gly Gly Ala Gly Val Gln His Ile Ala Leu
            260                 265                 270

Asn Thr Gly Asp Ile Val Glu Thr Val Arg Thr Met Arg Ala Ala Gly
            275                 280                 285

Val Gln Phe Leu Asp Thr Pro Asp Ser Tyr Tyr Asp Thr Leu Gly Glu
            290                 295                 300

Trp Val Gly Asp Thr Arg Val Pro Val Asp Thr Leu Arg Glu Leu Lys
305                 310                 315                 320

Ile Leu Ala Asp Arg Asp Glu Asp Gly Tyr Leu Leu Gln Ile Phe Thr
            325                 330                 335

Lys Pro Val Gln Asp Arg Pro Thr Val Phe Phe Glu Ile Ile Glu Arg
            340                 345                 350

His Gly Ser Met Gly Phe Gly Lys Gly Asn Phe Lys Ala Leu Phe Glu
            355                 360                 365

Ala Ile Glu Arg Glu Gln Glu Lys Arg Gly Asn Leu
            370                 375                 380

<210> SEQ ID NO 45
<211> LENGTH: 419
<212> TYPE: PRT
<213> ORGANISM: Mycosphaerella graminicola

<400> SEQUENCE: 45

Met Ala Pro Gly Ala Leu Leu Val Thr Ser Gln Asn Gly Arg Thr Ser
1               5                   10                  15

Pro Leu Tyr Asp Ser Asp Gly Tyr Val Pro Ala Pro Ala Ala Leu Val
            20                  25                  30

Val Gly Gly Glu Val Asn Tyr Arg Gly Tyr His His Ala Glu Trp Trp
            35                  40                  45

Val Gly Asn Ala Lys Gln Val Ala Gln Phe Tyr Ile Thr Arg Met Gly
            50                  55                  60

Phe Glu Pro Val Ala His Lys Gly Leu Glu Thr Gly Ser Arg Phe Phe
65              70                  75                  80
```

-continued

```
Ala Ser His Val Val Gln Asn Asn Gly Val Arg Phe Val Phe Thr Ser
                85                  90                  95

Pro Val Arg Ser Ser Ala Arg Gln Thr Leu Lys Ala Ala Pro Leu Ala
            100                 105                 110

Asp Gln Ala Arg Leu Asp Glu Met Tyr Asp His Leu Asp Lys His Gly
        115                 120                 125

Asp Gly Val Lys Asp Val Ala Phe Glu Val Asp Asp Val Leu Ala Val
    130                 135                 140

Tyr Glu Asn Ala Val Ala Asn Gly Ala Glu Ser Val Ser Ser Pro His
145                 150                 155                 160

Thr Asp Ser Cys Asp Glu Gly Asp Val Ile Ser Ala Ala Ile Lys Thr
                165                 170                 175

Tyr Gly Asp Thr Thr His Thr Phe Ile Gln Arg Thr Thr Tyr Thr Gly
            180                 185                 190

Pro Phe Leu Pro Gly Tyr Arg Ser Cys Thr Thr Val Asp Ser Ala Asn
        195                 200                 205

Lys Phe Leu Pro Pro Val Asn Leu Glu Ala Ile Asp His Cys Val Gly
    210                 215                 220

Asn Gln Asp Trp Asp Glu Met Ser Asp Ala Cys Asp Phe Tyr Glu Arg
225                 230                 235                 240

Cys Leu Gly Phe His Arg Phe Trp Ser Val Asp Asp Lys Asp Ile Cys
                245                 250                 255

Thr Glu Phe Ser Ala Leu Lys Ser Ile Val Met Ser Ser Pro Asn Gln
            260                 265                 270

Val Val Lys Met Pro Ile Asn Glu Pro Ala His Gly Lys Lys Lys Ser
        275                 280                 285

Gln Ile Glu Glu Tyr Val Asp Phe Tyr Asn Gly Pro Gly Val Gln His
    290                 295                 300

Ile Ala Leu Arg Thr Pro Asn Ile Ile Glu Ala Val Ser Asn Leu Arg
305                 310                 315                 320

Ser Arg Gly Val Glu Phe Ile Ser Val Pro Asp Thr Tyr Tyr Glu Asn
                325                 330                 335

Met Arg Leu Arg Leu Lys Ala Ala Gly Met Lys Leu Glu Glu Ser Phe
            340                 345                 350

Asp Ile Ile Gln Lys Leu Asn Ile Leu Ile Asp Phe Asp Glu Gly Gly
        355                 360                 365

Tyr Leu Leu Gln Leu Phe Thr Lys Pro Leu Met Asp Arg Pro Thr Val
    370                 375                 380

Phe Ile Glu Ile Ile Gln Arg Asn Asn Phe Asp Gly Phe Gly Ala Gly
385                 390                 395                 400

Asn Phe Lys Ser Leu Phe Glu Ala Ile Glu Arg Glu Gln Asp Leu Arg
                405                 410                 415

Gly Asn Leu

<210> SEQ ID NO 46
<211> LENGTH: 399
<212> TYPE: PRT
<213> ORGANISM: Coccicoides immitis

<400> SEQUENCE: 46

Met Ala Pro Ala Ala Asp Ser Pro Thr Leu Gln Pro Ala Gln Pro Ser
1               5                   10                  15

Asp Leu Asn Gln Tyr Arg Gly Tyr Asp His Val His Trp Tyr Val Gly
            20                  25                  30
```

-continued

```
Asn Ala Lys Gln Ala Ala Thr Tyr Tyr Val Thr Arg Met Gly Phe Glu
         35                  40                  45
Arg Val Ala Tyr Arg Gly Leu Glu Thr Gly Ser Lys Ala Val Ala Ser
 50                  55                  60
His Val Arg Asn Gly Asn Ile Thr Phe Ile Leu Thr Ser Pro Leu
 65                  70                  75                  80
Arg Ser Val Glu Gln Ala Ser Arg Phe Pro Glu Asp Glu Ala Leu Leu
                 85                  90                  95
Lys Glu Ile His Ala His Leu Glu Arg His Gly Asp Gly Val Lys Asp
             100                 105                 110
Val Ala Phe Glu Val Asp Cys Val Glu Ser Val Phe Ser Ala Ala Val
             115                 120                 125
Arg Asn Gly Ala Glu Val Val Ser Asp Val Arg Thr Val Glu Asp Glu
 130                 135                 140
Asp Gly Gln Ile Lys Met Ala Thr Ile Arg Thr Tyr Gly Glu Thr Thr
 145                 150                 155                 160
His Thr Leu Ile Glu Arg Ser Gly Tyr Arg Gly Gly Phe Met Pro Gly
                 165                 170                 175
Tyr Arg Met Glu Ser Asn Ala Asp Ala Thr Ser Lys Phe Leu Pro Lys
                 180                 185                 190
Val Val Leu Glu Arg Ile Asp His Cys Val Gly Asn Gln Asp Trp Asp
             195                 200                 205
Glu Met Glu Arg Val Cys Asp Tyr Tyr Glu Lys Ile Leu Gly Phe His
             210                 215                 220
Arg Phe Trp Ser Val Asp Asp Lys Asp Ile Cys Thr Glu Phe Ser Ala
 225                 230                 235                 240
Leu Lys Ser Ile Val Met Ala Ser Pro Asn Asp Ile Val Lys Met Pro
                 245                 250                 255
Ile Asn Glu Pro Ala Lys Gly Lys Lys Gln Ser Gln Ile Glu Glu Tyr
                 260                 265                 270
Val Asp Phe Tyr Asn Gly Ala Gly Val Gln His Ile Ala Leu Arg Thr
             275                 280                 285
Asn Asn Ile Ile Asp Ala Ile Thr Asn Leu Lys Ala Arg Gly Thr Glu
 290                 295                 300
Phe Ile Lys Val Pro Glu Thr Tyr Tyr Glu Asp Met Lys Ile Arg Leu
 305                 310                 315                 320
Lys Arg Gln Gly Leu Val Leu Asp Glu Asp Phe Glu Thr Leu Lys Ser
                 325                 330                 335
Leu Asp Ile Leu Ile Asp Phe Asp Glu Asn Gly Tyr Leu Leu Gln Leu
             340                 345                 350
Phe Thr Lys His Leu Met Asp Arg Pro Thr Val Phe Ile Glu Ile Ile
             355                 360                 365
Gln Arg Asn Asn Phe Ser Gly Phe Gly Ala Gly Asn Phe Arg Ala Leu
             370                 375                 380
Phe Glu Ala Ile Glu Arg Glu Gln Ala Leu Arg Gly Thr Leu Ile
 385                 390                 395
```